US007740850B2

(12) United States Patent
Zhu et al.

(10) Patent No.: US 7,740,850 B2
(45) Date of Patent: Jun. 22, 2010

(54) PDGFRβ-SPECIFIC ANTIBODIES

(75) Inventors: Zhenping Zhu, Oakland, NJ (US); Juqun Shen, Flushing, NY (US)

(73) Assignee: ImClone, LLC, New York, NY (US)

( * ) Notice: Subject to any disclaimer, the term of this patent is extended or adjusted under 35 U.S.C. 154(b) by 26 days.

(21) Appl. No.: 12/148,482

(22) Filed: Apr. 17, 2008

(65) Prior Publication Data
US 2009/0053241 A1 Feb. 26, 2009

Related U.S. Application Data

(60) Provisional application No. 60/923,979, filed on Apr. 17, 2007.

(51) Int. Cl.
*A61K 39/395* (2006.01)
*C07K 16/28* (2006.01)
(52) U.S. Cl. .............................. 424/143.1; 530/388.22
(58) Field of Classification Search ...................... None
See application file for complete search history.

(56) References Cited

U.S. PATENT DOCUMENTS

| 5,530,101 | A | 6/1996 | Queen et al. |
| 5,620,687 | A | 5/1997 | Hart et al. |
| 5,686,572 | A | 11/1997 | Wolf et al. |
| 5,817,310 | A | 10/1998 | Ramakrishnan et al. |
| 5,840,299 | A | 11/1998 | Bendig et al. |
| 5,872,218 | A | 2/1999 | Wolf et al. |
| 5,882,644 | A | 3/1999 | Chang et al. |
| 5,976,534 | A | 11/1999 | Hart et al. |
| 7,060,271 | B2 | 6/2006 | Ramakrishnan et al. |
| 2003/0228307 | A1 | 12/2003 | Ramakrishnan et al. |

FOREIGN PATENT DOCUMENTS

| WO | WO 93/11236 | 6/1993 |
| WO | 0154723 | 8/2001 |
| WO | 0190192 | 11/2001 |
| WO | 02070008 | 9/2002 |
| WO | 2005046602 | 5/2005 |
| WO | 2006020258 | 2/2006 |
| WO | WO 2008/011216 | 1/2008 |

OTHER PUBLICATIONS

Batelyet al., Life Science 62:143-50 (1998).
Board et al, Drug Resistance Updates 8:75-83 (2005).
Giese et al., Arterioscler Thromb Vasc Biol.19:900-909 (1999).
Griffiths et al., Embo J. 13:3245-3260 (1994).
Hall, Toxicologic Pathology 34:763-775 (2006).
Hawkins, et al., J. Mol. Bio. 226:889-96 (1992).
Hoffmann et al., Anticancer Res. 17:4419 (1997).
Jayson et al., J. Clinical Oncology 23(5):973-981 (2005).
Jo, et al., Amer. J. Path. 168(6):2036-2053 (2006).
Jones Genetics 85:12 (1977).
Kingsmann et al., Gene. 7:141 (1979).
Loizos et al., Molec. Can. Therap. 4(3):369-377(2005).
Lokker et al., J. Biol. Chem. 272(52):33037-33044 (1997).
Low, et al., Journal of Molecular Biology 250:359-68 (1996).
Lu et al., Int. J. Cancer 97:393-399 (2002).
Maeda,et al., Hum. Antibod. Hybridomas 2:124-34 (1991).
Panek et al., J. Pharmacol. and Exp. Therapeutics 283:1433-44 (1997).
Pearson et al., Proc. Natl. Acad. Sci. 85:2444-48 (1998).
Petrides et al., CancerRes. 50:3934-39 (1990).
Prewett, et al., Cancer Research 59:5209-18 (1999).
Queen et al., PNAS 86:10029-10033 (1989).
Radinsky et al., Clin. Cancer Res. 1:19-31 (1995).
Roguska et al., PNAS 91:969-973 (1994).
Sambrook et al., Molecular Cloning: A Laboratory Manual, 2nd Ed, Cold Spring Harbor Laboratory Press (1989).
Sauter et al., Am. J Path. 148:1047-53 (1996).
Scahill et al., PNAS 80:4654-4659 (1983).
Li et al., BMC Cancer 6(79):1-20 (2006).
Li et al., Journal of Biochemistry 327:709-716 (1997).
Lin and Sessa Cancer Cell 6:529-531 (2004).
Lin et al., Journal of American Heart Association 44:42-47 (2004).
Lindblom et al., Genes & Dev. 17:1835-1840 (2003).
Mancuso et al., J of Clin. Investigation, 116(10):2585-2620 (2006).
Mathew et al., Seminars in Oncology 31(2)(6):24-29(2004).
McDonald and Baluk Cancer Research 62:5381-5385 (2002).
Mendel et al., Clinical Cancer Research 9:327-337 (2003).
Miyamoto and Fox, Journal of Biol. Chem. 275(4):2825-2830(2000).
Morikawa et al., Am J Pathol. 160(3):985-1000 (2002).
Motzer et al., J. of Clin. Oncol. 24(1):16-24 (2006).
Mulvihill et al., Journal of Amer. Heart Assoc. 24:1283-89 (2004).
Nam et al., Cancer Research 65(20):9185-9189 (2005).
Ostman, Cytokine Growth Factor Rev.15:275-286 (2004).
Owens et al., Physiol. Rev. 84:767-801 (2004).
Pietras, Journal of Clinical Oncology 23(5)11-14 (2005).
Potapova et al., Mol. Cancer Thera. 5(5):1280-9 (2006).
Reigstad, FEBS Journal 272:5723-5741 (2005).
Roberts et al., Cancer Research 65(3):957-966 (2005).
Rolny et al., Blood 108(6):1877-1886 (2006).
Salnikov et al., The FASEB Journal, Express Article10.1096/fj.02-1201fje. (Published online 2003).
Schittenhelm et al., Cancer Rearch 66(1):473-81 (2006).
Singer et al., Endocrine-Related Cancer 11:861-69 (2004).
Slater et al., Journal of American Heart Association 24:1204-1210 (2004).
Song et al., Nat. Cell Biol., 7:870-879 ( 2005).
Stefansson et al., Cancer Research 66(6):3303-09 (2006).
Stegemann et al., J. Appl. Physiol. 98:2321-2327 (2005).
Tong et al., Cancer Research 64:3731-36 (2004).
Uehara, Journal of the National Cancer Institute 95(6):458-470 (2003).

(Continued)

Primary Examiner—Christine J Saoud
(74) Attorney, Agent, or Firm—Nicole S. Woods

(57) ABSTRACT

The invention is directed to novel PDGFRβ-specific antagonists. The antagonists include antibodies, which can be bispecific. The antibodies are used to reduce or inhibit tumor growth and or to treat an angiogenic disease. The invention also includes combinations of PDGFRβ-specific antagonists with VEGFR antagonists for such treatments. The antagonists can further be administered in combination with other anti-angiogenic or anti-neoplastic drugs.

6 Claims, 23 Drawing Sheets

OTHER PUBLICATIONS

Uutela et al., Blood 104(10):3198-3204 (2004).
Vosseler et al., Cancer Research 65(4):1294-1305 (2005).
Wexberg, J. Am. Coll. Cardiol. 39:400-407 (2002).
Wilhelm et al., Nature Reviews 5:835-844(2006).
Wolff et al., Clinical Cancer Research 10:3528-34 (2004).
Yao et al., Cancer Research 66(5):2639-2649 (2006).
Yokoi et al., Cancer Research 65(22):10371-10380 (2005).
Zalewski et al., Circ. Res. 91:652-655 (2002).
Zaslavsky et al., FEBS Letters 579:3899-3906 (2005).
Zhang et al., Journal of American Heart Association 25:533-38 (2005).
Zhang, Xu, Chinese Journal of Cancer 25(1):92-95 (2006).
Zhang and Meier, Molecular Pharmacology Fast Forward 10.1124/mol.106023721 (2006).
Abrams et al., Mol. Cancer Thera.2:1011-21 (2003).
Abramsson et al., Circulation 105:112-117 (2002).
Abramsson et al., J. Clin. Invest. 112:1142-1151 (2003).
Armulik et al., Circ. Res. 97:512-523 (2005).
Avramis et al Cancer Chemother. Pharmacol. 52:307-18 (2003).
Bagley et al., Cancer Research 65(21):9741-9750 (2005).
Ball et al., J. of Cell Biol. 177(3)489-500 (2007).
Baluk et al., American Journal of Pathology 163(5):1801-1815 (2003).
Banfi, et al., Vascular Biology 7:227-234 (2005).
Baranowska-Kortylewicz et al., Cancer Res. 65(17):7824-7831 (2005).
Barst, Journal of Clinical Investigation 115(10)2691-2694 (2005).
Baudhuin et al., FASEB Journal Article 10.1096/fj.03-0302fje. (Published online 2003).
Berger et al., Blood 105:1094-1101 (2005).
Bergers and Song, Neuro-Oncol. 7:452-464 ( 2005).
Bergers and Benjamin, Nature 3:401-410 (2003).
Bergers et al., J. Clin. Invest. 111(8):1287-1295 (2003).
Berk, Physiological Reviews 81(3):999-1030 (2001).
Burgess et al., PNAS 102(9):3395-3400 (2005).
Carmeliet, Nature Medicine 6(3):389-395 (2000).
Cartel et al., Am. J. Physiol. Lung Cell Mol. Physiol. 281:786-798 (2001).
Carter et al., PNAS 102(31):11011-11016 (2005).
Chantrain et al., European J of Cancer 42:310-318 (2006).
Chelouche-Lev et al., Clin. Cancer Research 11:306-314 (2005).
Chen et al., Cancer Letters XX:1-10 (2005).
Chen et al., Mol. Pharmacol. Fast Forward 10.1124/mol105.020172(2006).
Choi et al., Nature Letters 435(14): 347-353 (2005).
Erber et al., The FASEB Journal Express Article 10.1096/fj.03-0271fje. (Published online 2003).
Furuhashi et al., Cancer Research 64:2725-33 (2004).
Gee et al., American Journal of Pathology 162(1):183-193(2003).
Gerhardt and Betsholtz, Cerll Tissue Res. 314:15-23 (2003).
Goparaju et al., Molecular and Cellular Biology25(10)4237-4249 (2005).
Griffin, et al., Cancer Research 62:1702-1706 (2002).
Guo et al., American Journal of Pathology162(4):1083-1093 (2003).
Heinrich et al., Blood 96(3):925-932 (2000).
Heldin et al., Nature 4:806-13 (2004).
Hellstrom, et al., Journal of Cell Biology 153(3):543-553 (2001).
Heuchel et al., PNAS 96:11410-11415(1999).
Holdhoff et al., Blood Cells Molecules & Diseases 34:181-185(2005).
Homsi and Daud, Journal of Moffat Cancer Center 14(3):285-294 (2007).
Jain and Booth, Journal of Clin. Invest. 112:1134-36(2003).
Jain, Science 307:58-62 (2005).
Jechlinger et al., J of Clin Investig., 116(6):1561-1570 (2006).
Joyce, Johanna, Cancer Cell 7:513-520 (2005).
Kaminski et al., Blood 97(7):1990-1998 (2001).
Kano et al., Journal of Cell Science 118:3759-3768 (2005).
Kaplan-Albuquerque, J. of Biol. Chem. 280(20):19966-19976 (2005).
Kim et al., Cancer Research 64:4201-4208 (2004).
Laird et al., Cancer Research 60:4152-4160 (2000).
Laird et al., The FASEB Journal, 16:681-690 (2002).
Larochelle et al., Nature Cell Biology 3:517-521 (2001).
Aujame, et al., Human Antibodies 8:155-68 (1997).
Betsholtz, et al., Bioessays 23:494-507 (2001).
Binz, et al, Nat. Biotech. 23:1257-68, (2005).
Bruggemann, et al. Curr. Opin. Biotechnol. 8:455-458 (1997).
Coligan, et al., Current Protocols and Immunology (1994).
Collins, Glia 15:289-96 (1995).
de Haard, et al., J. Biol. Chem. 274:18218-18230 (1999).
Elbashir, et al., Nature 411:494-498 (2001).
Grandis, et al., Cancer 78:1284-92 (1996).
Green, et al., Nature Genet. 7:13-21 (1994).
Hannon, Nature, 418:244-251, (2002).
Hermentin, et al., Behring Inst. Mitt. 82:197-215 (1988).
Jones, et al., Nature 321:522-525 (1986).
Kabat, et al., Sequences of Proteins of Immunological Interest. 5$^{th}$ ed. (1991) p. 103-130, 647, 651.
Kaufman, et al., J. Mol. Biol. 159:601-21 (1982).
Khvorova, Cell 115:209-216 (2003).
Lu, et al., Int. J. Cancer 97:393-399 (2002).
McCafferty, et al., Nature 348:552-554 (1990).
Mello, et al., Nature 431:338-342, (2004).
Mendez, et al., Nature Genet 15:146-156 (1997).
Paddison, et al., Curr. Opin. Mol. Ther. 5:217-224 (2003).
Padlan, Mol. Immunol. 28:489-498 (1991).
Pedley, et al., Br. J. Cancer 68:69-73 (1993).
Riechmann, et al., Nature 332:323-327 (1988).
Sandy, et al., Br. J. Orthod. 25:269-74 (1998).
Sazani, et al., J. Clin. Invest. 112:481-486 (2003).
Shen, et al., Proceeding of the Annual Meeting of the AACR, NY, NY. 48: 1133 (Apr. 1, 2007).
Shimizu, et al., Japan J. Cancer Res. 85:567-71 (1994).
Southern, et al., J. Mol. Appl. Genet. 1:327-41 (1982).
Tijssen, Overview of Principles of Hybridization and the Strategy of Nucleic Acid Probe Assays (1993).
Wagner, et al., Eur. J. Immunol. 24:2672-2681 (1994).
Williams, Biochem. Soc. Trans. 25:509-513 (1997).
Zamecnik, et al., Proc. Natl. Acad. Sci. USA 75(1):280-284 (1978).
Heidaran, et al., Research Communications 144(9):140-145 (1995).

FIG. 16

Sequence information of 1B3:
DNA of 1B3 VH:
CAGGTGCAGCTGCAGGAGTCGGGGGGAGGCCTGGTCAAGCCTGGGGGGTCCCTGAGACTCTCCT
GTGCAGCCTCTGGATTCACCTTCAGTAGCTATAGCATGAACTGGGTCCGCCAGGCTCCAGGGAA
GGGGCTGGAGTGGGTCTCATCCATTAGTAGTAGTAGTAGTTACATATACTACGCAGACTCCGTG
AAGGGCCGGTTCACCATCTCCAGAGACAATTCCAAGAACACGCTGTATCTGCAAATGAACAGCC
TGAGAGCCGAGGACACGGCCGTGTATTACTGTGCGAAAGGGGGGCGCCCGCTCCTAGTCTTTGA
CTTCTGGGGCCAGGGAACCCTGGTCACCGTCTCAAGC

Protein of 1B3 VH:
QVQLQESGGGLVKPGGSLRLSCAASGFTFS<u>SYSMN</u>WVRQAPGKGLEWVS<u>SISSSSSYIY
YADSVKG</u>RFTISRDNSKNTLYLQMNSLRAEDTAVYYCAK<u>GGRPLLVFDF</u>WGQGTLVTVSS

DNA of 1B3 VL:
GAAATTGTGATGACACAGTCTCCAGGCACCCTGTCTTTGTCTCCAGGGGAAAGAGCCACCCTCT
CCTGCAGGGCCAGTCAGAGTGTTAGCAGCAGCTACTTAGCCTGGTACCAGCAGAAACCTGGCCA
GGCTCCCAGGCTCCTCATCTATGATGCATCCAAGAGGGCCACCGGCATCCCAGCCAGGTTCAGT
GGCAGTGGGTCTGGGACAGACTTCACTCTCACCATCAGCACCCTAGAGTCTGAAGATTCTGCAG
TTTATTACTGTCAGCAACGTGGCTACTGGCCTCCCATCACCTTCGGCCAAGGGACACGACTGGA
GATTAAACGA

Protein of 1B3 VL:
EIVMTQSPGTLSLSPGERATLSC<u>RASQSVSSSYLA</u>WYQQKPGQAPRLLIY<u>DASKRA</u>TGI
PARFSGSGSGTDFTLTISTLESEDSAVYYC<u>QQRGYWPPIT</u>FGQGTRLEIKR

FIG. 17

Sequence Information of 2C5:

DNA of 2C5 VH:
CAGGTGCAGCTGGTGCAGTCTGGGGCTGAGGTGAAGAAGCCTGGGTCCTCGGTGAAGGTCTCCTG
CAAGGCTTCTGGAGGCACCTTCAGCAGCTATGCTATCAGCTGGGTGCGACAGGCCCCTGGACAAG
GGCTTGAGTGGATGGGAAGGATCATCCCTATCCTTGGTATAGCAAACTACGCACAGAAGTTCCAG
GGCAGAGTCACGATTACCGCGGACAAATCCACGAGCACAGCCTACATGGAGCTGAGCAGCCTGAG
ATCTGAGGACACGGCCGTCTATTACTGTGCGAGAGATATGGGTTCAAGGAATTATTATTACTTCT
ACTGGGGCCAGGGAACCCTGGTCACCGTCTCAAGC

Protein of 2C5 VH:
QVQLVQSGAEVKKPGSSVKVSCKASGGTFSSYAISWVRQAPGQGLEWMG**RIIPILGIANYAQKFQ
GRVTITADKSTSTAYMELSSLRSEDTAVYYCARDMGSRNYYYFY**WGQGTLVTVSS

DNA of 2C5 VL:
GAAATTGTGCTGACTCAGTCTCCAGCCACCCTGTCTTTGTCTCCAGGGGAAAGAGCCACCCTCTC
CTGCAGGGCCAGTCAGAGTGTTGGCAGGTACTTAGCCTGGTACCAACAGAAACCTGGCCAGGCTC
CCAGGCTCCTCATCTATGGTGCATCCAACAGGGCCACTGGCATCCCAGCCAGGTTCAGTGGCAGT
GGGTCTGGGACAGACTTCACTCTCACCATCAGCAGCCTAGAGCCTGAAGATTTTGCAGTTTATTA
CTGTCAGCAGCGTAGCAACTGGCCTCTCACTTTCGGCGGAGGGACCAAGGTGGAGATCAAA

Protein of 2C5 VL:
EIVLTQSPATLSLSPGERATLSCRASQSVGRYLAWYQQKPGQAPRLLIYGASNRATGIPARFSGS
GSGTDFTLTISSLEPEDFAVYYCQQRSNWPLTFGGGTKVEIK

PDGFRβ-SPECIFIC ANTIBODIES

CROSS-REFERENCE TO RELATED APPLICATIONS

This application claims the benefit of the filing date of U.S. Provisional Patent Application No. 60/923,979, filed Apr. 17, 2007, the disclosure of which is hereby incorporated herein by reference.

FIELD OF THE INVENTION

The present invention is directed to methods and compositions for inhibiting angiogenesis and tumor growth. The invention demonstrates the effect of specific inhibition of platelet derived growth factor receptor-beta (PDGFRβ) on angiogenesis, and provides for treatment of angiogenesis using PDGFRβ specific antagonists, alone or in combination with inhibitors of a VEGF receptor. The specific inhibitors can be antibodies or antigen binding fragments thereof. Further, the inhibitors can be bispecific.

BACKGROUND

Platelet-derived growth factors (PDGFs) are a family of potent mitogens for almost all mesenchyme-derived cells. There are four PDGF isoforms, A, B, C and D, that form five different disulphide-linked dimeric proteins PDGF-AA, -BB, -AB, -CC, and -DD. These growth factors exert their cellular effects through two structurally related tyrosine kinase receptors: PDGF receptor α (PDGFRα) and PDGF receptor β (PDGFRβ). (Sandy, J. R., 1998, *Br. J. Orthod.* 25:269-74; Betsholtz, C. et al., 2001, *Bioessays* 23:494-507).

PDGFRα and PDGFRβ are structurally similar and can form heterodimers as well as homodimers. PDGF-BB and PDGF-DD are the primary activators of ββ homodimeric receptors. PDGF-AA activates only αα receptor dimers, whereas PDGF-AB, PDGF-BB, and PDGF-CC activate αα and αβ receptor dimers. The dimeric ligand molecules bind to two receptor proteins simultaneously and induce receptor dimerization, autophosphorylation of specific residues within the receptor's cytoplasmic domain, and intracellular signaling. Ultimately, the activation of PDGFRβ signaling pathway induces various cellular responses, including cell proliferation and migration.

Angiogenesis is believed to be essential for both tumor growth and metastasis. Development of a vascular system, or vasculogenesis, involves the assembly of two principal cell types, endothelial cells (EC) and pericytes/vascular smooth muscle cells (SMC), into mature blood vessels. The involvement of the PDGF-B/PDGFRβ signaling pathway in vasculogenesis is suggested by PDGF-B and PDGFRβ knockout mice. The PDGF-B and PDGFRβ knockout phenotypes are virtually identical in that mice exhibit hemorrhages due to the loss of coverage of pericytes and smooth muscle cells in vessels. The studies indicated that PDGFRβ is involved in pericyte recruitment to capillaries and development of smooth muscle cells in vessels. Pericyte recruitment to coat nascent vessels is essential for the stabilization and further establishment of the vascular network. Vessels lacking adequate pericyte coverage are more vulnerable to VEGF inhibition than well-established mature vessels.

A number of tyrosine kinase inhibitors under development as anti-tumor agents have been found to inhibit PDGFRβ. However, these compounds have multiple tyrosine kinase targets. For example, imatinib mesylate (Gleevec®/ST571) was developed as an Abelson (Abl) tyrosine kinase inhibitor, and also inhibits c-kit, PDGFRα, and PDGFRβ. Sunitinib malate (Sutent®/SU11248) is a broad-spectrum, orally available multitargeted tyrosine kinase inhibitor with activity against VEGFR, PDGFR, c-KIT, and FLT-3. CP-673,451 is an inhibitor of both PDGFRα and PDGFRβ. Since these small molecule antagonists are not specific to these receptors, it is not possible to distinguish the contribution of PDGFRβ signaling to angiogenesis, including tumor-associated angiogenesis, tumor stimulation and growth, or toxicities associated with administration of such compounds that might be due to unnecessary targeting of multiple receptors.

Accordingly, the invention provides PDGFRβ-specific antagonists, demonstrates the role of PDGFRβ in angiogenesis, including angiogenesis that supports tumor growth and survival, and provides methods of treating tumors and angiogenic diseases. The invention further demonstrates the advantage of simultaneously inhibiting signal transduction through PDGFRβ and VEGFR.

SUMMARY OF THE INVENTION

The invention provides a PDGFRβ-specific antagonist of PDGFRβ mediated signal transduction. In an embodiment of the invention, the PDGFRβ-specific antagonist is an antibody that binds specifically to platelet derived growth factor receptor-β (PDGFRβ). One such antibody has complementarity determining regions that are at least about 90% homologous or about 90% identical to SEQ ID NO:20 at CDRH1; SEQ ID NO:22 at CDRH2; SEQ ID NO:24 at CDRH3; SEQ ID NO:28 at CDRL1; SEQ ID NO:30 at CDRL2; and SEQ ID NO:32 at CDRL3. Another such antibody comprises a heavy chain variable domain amino acid sequence of SEQ ID NO:18 and a light chain variable domain amino acid sequence of SEQ ID NO:26. Another embodiment of such an antibody has complementarity determining regions that are at least about 90% homologous or about 90% identical to SEQ ID NO:4 at CDRH1; SEQ ID NO:6 at CDRH2; SEQ ID NO:8 at CDRH3; SEQ ID NO:12 at CDRL1; SEQ ID NO:14 at CDRL2; and SEQ ID NO:16 at CDRL3. Another such antibody comprises a heavy chain variable domain amino acid sequence of SEQ ID NO:2 and a light chain variable domain amino acid sequence of SEQ ID NO:10. The invention further includes a PDGFRβ-specific antibody that binds to the same or over lapping epitope as one of the abovementioned antibodies.

Antibodies of the invention may be chimeric, humanized, or human. Antibodies of the invention can also be antigen binding fragments such as, for example, single chain antibodies, Fab and F(ab')$_2$ fragments, single chain Fvs, and single domain antibodies. The antibodies also include diabodies and triabodies. Further, the antibodies can be bispecific.

The invention further provides isolated polynucleotides that encode such antibodies, expression vectors, and host cells that produce the antibodies.

The invention provides a method of modulating activity of platelet derived growth factor receptor-β (PDGFRβ) in a mammal comprising administering to the mammal an effective amount of a PDGFRβ-specific antagonist. In an embodiment of the invention, an effective amount of a PDGFRβ-specific antagonist is used to inhibit angiogenesis in a mammal. In another embodiment, an effective amount of a PDGFRβ-specific antagonist is used to reduce tumor growth in a mammal. The PDGFRβ-specific antagonist can be an antibody that binds to PDGFRβ, or any other agent that binds to PDGFRβ or a PDGFRβ ligand and reduces or blocks PDGFRβ-mediated signal transduction. The treatment methods can further comprise coadministration of a VEGFR antagonist. Alternatively, the treatment methods can employ an agent that is both a PDGFRβ-specific antagonist and a VEGFR antagonist, such as a bispecific antibody.

According to the invention, treatment of tumors and angiogenic conditions can further include administration of an antineoplastic agent, such as a chemotherapeutic or radiation.

BRIEF DESCRIPTION OF THE FIGURES

FIG. 16 shows the DNA and amino acid sequences of the variable heavy and variable light chains of 1B3, with CDRs underlined.

FIG. 17 shows the DNA and amino acid sequences of the variable heavy and variable light chains of 2C5, with CDRs underlined.

DETAILED DESCRIPTION OF THE INVENTION

Figure 1A:
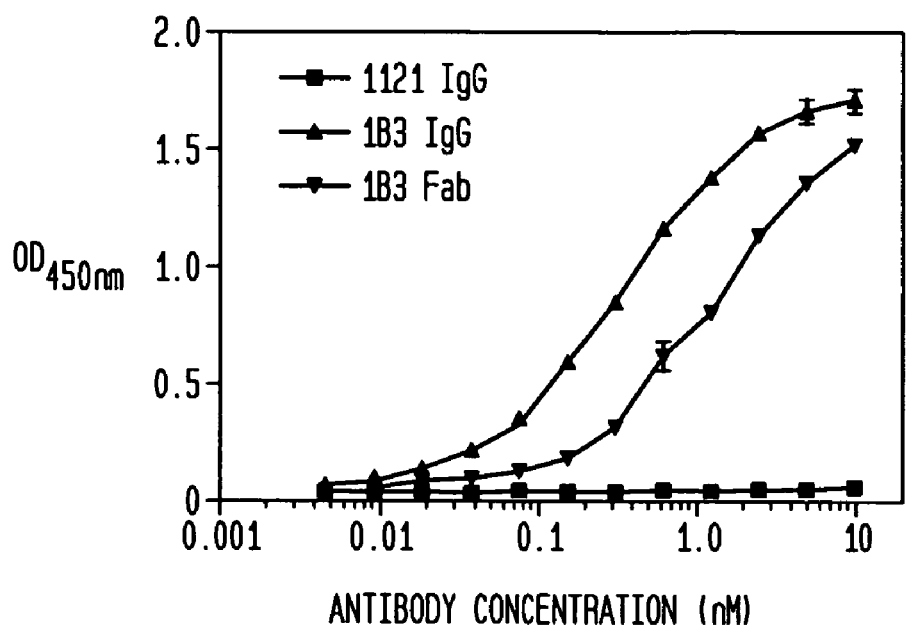
FIG. 1 depicts quantitative receptor binding and blocking assays for the anti-PDGFRβ antibody, 1B3. (A) Purified Fab fragments or full-length 1B3 IgG were added to mPDGFRβ/Fc-coated plates (1 µg/ml), and incubated at RT for 1 h. Plate-bound antibodies were detected with a goat anti-human-κ antibody-HRP. (B) 1B3 antibody or Fab were first mixed with a fixed amount of mPDGFRβ/Fc (50 ng) and incubated at RT for 30 min. The mixture was then transferred to the plates precoated with PDGF-BB (0.5 µg/ml) and incubated at RT for 1 h. Plate-bound mPDGFRβ/Fc was detected with a goat anti-human Fc antibody-HRP conjugate. IMC-1121 is an antibody directed against human VEGFR2. Data represent the mean±SD of triplicate samples.

The present invention provides antibodies, or fragments thereof, which are specific for PDGFRβ. The antibodies of the invention include those that specifically bind to domains 1 and 2 of PDGFRβ. Antibodies of the invention include 2C5 and 1B3.

The present invention also provides compositions and methods for treatment of tumors and angiogenic diseases, with the above-described antibodies, and with anti-PDGFRβ antagonists in combination with VEGFR antagonists. In particular, the invention provides for specific targeting of the PDGF-B/PDGFRβ signal transduction pathway for cancer therapy by anti-tumor and anti-angiogenesis mechanisms. Further, the invention provides for therapy of angiogenic diseases.

Accordingly, the present invention provides platelet derived growth factor receptor-β (PDGFRβ) antagonists that are specific for PDGFRβ. The PDGFRβ-specific antagonists are biological molecules that preferentially inhibit PDGFRβ mediated signal transduction. According to the invention, PDGFRβ-specific antagonists mediate inhibition of PDGFRβ mediated signal transduction that is at least 3×, or at least 5×, or at least 10× greater than inhibition of PDGFRα. One method of determining PDGFRβ-specific inhibition is to compare inhibition of PDGF-induced activation of cells engineered to express PDGFRβ, but not PDGFRα, with inhibition of PDGF-induce activation of cells engineered to express PDGFRα, but not PDGFRβ. Another way is to compare inhibition of PDGF-induced activation using a PDGF that preferentially activates PDGFRβ (e.g., PDGF-DD) and a PDGF that preferentially activates PDGFRα (e.g., PDGF-AA). In an embodiment of the invention, the PDGFRβ-specific antagonist is an antibody that binds to PDGFRβ. In another embodiment of the invention, the PDGFRβ-specific antagonist is a small molecule.

Anti-angiogenic approaches targeting VEGF receptors are gradually being accepted as effective for anti-tumor therapy. For example, an anti-VEGF antibody is approved for treatment of certain tumors. Further, an anti-mouse VEGFR2 antibody blocked VEGF/VEGFR2 interaction and inhibited VEGF-stimulated proliferation and survival of vascular endothelial cells in a murine xenograft model. However, although treatment with the anti-VEGFR2 antibody led to significant delay in growth of a variety of tumors transplanted in mice, tumor regression was infrequent. In addition, there is accumulating evidence suggesting that some tumors may become less sensitive (or even gain resistance) to VEGFR2 blockade during prolonged treatment periods.

According to the invention, PDGFRβ-specific inhibition significantly enhances both the anti-angiogenic and the anti-tumor activity of a VEGFR antagonist. Accordingly, the present invention provides improved methods of inhibiting angiogenesis and reducing or inhibiting tumor growth by administering a PDGFRβ-specific antagonist, and optionally, a VEGFR antagonist. The antagonists are molecules that block, modulate or impede the signaling mediated by a receptor tyrosine kinase (i.e., PDGFRβ or a VEGFR), and include, but are not limited to, antibodies, small molecules, proteins, polypeptides, ligand mimetics, antisense oligodeoxynucleotides, antisense RNAs, small inhibitory RNAs, triple helix forming nucleic acids, dominant negative mutants, and soluble receptor expression. Furthermore, the PDGFRβ-specific antagonists and VEGFR antagonists may be combined into a single compound, such as, but not limited to, a bispecific antibody.

PDGFRβ and the VEGF receptors are classified in the same family of kinase insert domain containing receptors. However, the VEGF receptors have seven immunoglobulin-like loops in their extracellular domains, as opposed to five in PDGFRα and PDGFRβ. Also, the VEGF receptors have longer kinase inserts. The amino acid sequences of PDGFRβ and VEGFRs from humans and other mammals and the nucleic acid sequences that encode them are well known in the art. The sequences of a non-limiting example of a human PDGFRβ are provided by GenBank accession number NM_002609. The nucleotide sequence encodes a protein having a cleavable signal sequence. The mature protein includes an extracellular portion containing about 499 amino acids, a 23 amino acid transmembrane region, and an intracellular portion of about 552 amino acids. Non-limiting examples of VEGFR sequences include NM_002019 (human VEGFR1/Flt1), NM_002253 (human VEGFR2/KDR/Flk1), and NM_182925 (human VEGFR3/Flt4). The Ig like domain structures of the extracellular domains, the locations of the transmembrane domains, and the intracellular regions, including tyrosine kinase domains, of each of these receptors is well known in the art.

The antibodies of the invention bind to PDGFRβ. As used herein, "antibody" refers to immunoglobulin (Ig) molecules and immunologically active portions or variants of immunoglobulin molecules. Antibodies contain one or more antigen binding sites that specifically binds with an antigen. Antibodies include, but are not limited to, polyclonal, monoclonal, chimeric, and humanized antibodies. Immunologically active portions include monovalent and divalent fragments such as Fv, single chain Fv (scFv), single variable domain (sVD), Fab, Fab' and F(ab')$_2$ fragments. Immunologically active portions can be incorporated into multivalent from such as diabodies, triabodies, and the like. Antibodies further include antigen binding fragments displayed on phage, and antibody conjugates.

An "isolated antibody" is an antibody that (1) has been partially, substantially, or fully purified from a mixture of components; (2) has been identified and separated and/or recovered from a component of its natural environment; (3) is monoclonal; (4) is free of other proteins from the same species; (5) is expressed by a cell from a different species; or (6) does not occur in nature. Contaminant components of its natural environment are materials which would interfere with diagnostic or therapeutic uses for the antibody, and may include enzymes, hormones, and other proteinaceous or non-proteinaceous solutes. Examples of isolated antibodies include an anti-PDGFRβ antibody that has been affinity purified using PDGFRβ, an anti-PDGFRβ antibody that has been made by a hybridoma or other cell line in vitro, a human anti-PDGFRβ isolated from a library such as a phage library, and a human anti-PDGFRβ antibody derived from a transgenic mouse.

In general, naturally occurring antibody molecules are composed of two identical heavy chains and two light chains. Each light chain is usually covalently linked to a heavy chain by an interchain disulfide bond, and the two heavy chains are further linked to one another by multiple disulfide bonds at the hinge region. The individual chains fold into domains having similar sizes (about 110-125 amino acids) and structures, but different functions. The light chain comprises one variable domain ($V_L$) and one constant domain ($C_L$). The heavy chain comprises one variable domain ($V_H$) and, depending on the class or isotype of antibody, three or four constant domains ($C_H1$, $C_H2$, $C_H3$ and $C_H4$). In mice and humans, the isotypes are IgA, IgD, IgE, IgG, and IgM, with IgA and IgG further subdivided into subclasses or subtypes. The portion of an antibody consisting of $V_L$ and $V_H$ domains is designated "Fv" and constitutes the antigen-binding site. A single chain Fv (scFv) is an engineered protein containing a $V_L$ domain and a $V_H$ domain on one polypeptide chain, wherein the N terminus of one domain and the C terminus of the other domain are joined by a flexible linker. "Fab" refers to the portion of the antibody consisting of $V_L$-$C_L$ (i.e., a light chain) and $V_H$-$C_H1$ (also designated "Fd").

Antibodies of the invention include single variable domains (sVDs) and antigen binding proteins that comprise sVDs. sVD binding sites can be obtained from antigen specific Fv regions (which comprise both $V_H$ and $V_L$ domains). Often, it can be shown that the binding affinity and specificity of an Fv region is contributed primarily by one of the variable domains. Alternatively, the scFv can be obtained directly. Direct sources of sVDs include mammals (e.g., camelids) that naturally express antibodies containing only $V_H$ domain. Further, phage display libraries can be constructed to express only a single variable domain. For example, a human domain antibody phage display library is commercially available from Domantis (Cambridge, UK).

The antibody variable domains show considerable amino acid sequence variablity from one antibody to the next, particularly at the location of the antigen binding site. Three regions, called "complementarity-determining regions" (CDRs) are found in each of $V_L$ and $V_H$. The CDRs of an antibody are often referred to as "hypervariable regions."

"Fc" is the designation for the portion of an antibody which comprises paired heavy chain constant domains. In an $IgG_1$ antibody, for example, the Fc comprises $C_H2$ and $C_H3$ domains. The Fc of an IgA or an IgM antibody further comprises a $C_H4$ domain. The Fc is associated with Fc receptor binding, activation of complement-mediated cytotoxicity and antibody-dependent cellular-cytotoxicity. For natural antibodies such as IgA and IgM, which are complexes of multiple IgG like proteins, complex formation requires Fc constant domains.

Finally, the "hinge" region separates the Fab and Fc portions of the antibody, providing for mobility of Fabs relative to each other and relative to Fc, as well as including multiple disulfide bonds for covalent linkage of the two heavy chains. Thus, antibodies of the invention include, but are not limited to, naturally occurring antibodies, bivalent fragments such as $(Fab')_2$, monovalent fragments such as Fab, single chain antibodies, single chain Fv (scFv), single domain antibodies, multivalent single chain antibodies, diabodies, triabodies, and the like that bind specifically with antigens. Antibody fragments also include polypeptides with amino acid sequences substantially similar to the amino acid sequence of the variable or hypervariable regions of the antibodies of the invention. Substantially the same amino acid sequence is defined herein as a sequence with at least 70%, at least about 80%, at least about 90%, at least about 95% or at least about 99% homology or identity to a compared amino acid sequence, as determined by the FASTA search method in accordance with Pearson and Lipman, *Proc. Natl. Acad. Sci. USA* 85:2444-2448 (1988).

The invention includes "chimeric" antibodies. Such antibodies generally comprise variable domains of one antibody and constant domains of a different antibody. Typically, to minimize host immune responses against the antibody and to enhance host responses against the antibody target by retaining antibody effector functions, the constant domains of a chimeric antibody are taken from the same species to which the chimeric antibody will be administered.

The invention also encompasses "humanized" antibodies. Humanized variable domains are constructed in which amino acid sequences which comprise one or more complementarity determining regions (CDRs) of non-human origin are grafted to human framework regions (FRs). For examples, see: Jones, P. T. et al., 1996, *Nature* 321, 522-25; Riechman, L. et al., 1988, *Nature* 332, 323-27; and U.S. Pat. No. 5,530,101 to Queen et al. A humanized construct is particularly valuable for elimination of adverse immunogenic characteristics, for example, where an antigen binding domain from a non-human source is desired to be used for treatment in a human. Variable domains have a high degree of structural homology, allowing easy identification of amino acid residues within variable domains which corresponding to CDRs and FRs. See, e.g., Kabat, E. A., et al., 1991, Sequences of Proteins of Immunological Interest. 5th ed. National Center for Biotechnology Information, National Institutes of Health, Bethesda, Md. Thus, amino acids which are likely to participate directly in antigen binding are easily identified. In addition, methods have been developed to preserve or to enhance affinity for antigen of humanized binding domains comprising grafted CDRs. One way is to include in the recipient variable domain the foreign framework residues which influence the conformation of the CDR regions. A second way is to graft the foreign CDRs onto human variable domains with the closest homology to the foreign variable region. Queen, C. et al., 1989, *Proc. Natl. Acad. Sci. USA* 86, 10029-33. CDRs are most easily grafted onto different FRs by first amplifying individual FR sequences using overlapping primers which include desired CDR sequences, and joining the resulting gene segments in subsequent amplification reactions. Grafting of a CDR onto a different variable domain can further involve the substitution of amino acid residues which are adjacent to the CDR in the amino acid sequence or packed against the CDR in the folded variable domain structure which affect the conformation of the CDR. Humanized variable domains of the invention therefore include human domains which comprise one or more non-human CDRs as well as such domains in which additional substitutions or replacements have been made to preserve or enhance binding characteristics.

An antibody of the invention may also employ variable domains which have been made less immunogenic by replacing surface-exposed residues so as to make the antibody appear as self to the immune system (Padlan, E. A., 1991, *Mol. Immunol.* 28, 489-98). Antibodies have been modified by this process with no loss of affinity (Roguska et al., 1994, *Proc. Natl. Acad. Sci. USA* 91, 969-973). Because the internal packing of amino acid residues in the vicinity of the antigen binding site remains unchanged, affinity is preserved. Substitution of surface-exposed residues according to the invention for the purpose of reduced immunogenicity does not mean substitution of CDR residues or adjacent residues which influence binding characteristics.

It is often preferable to employ variable domains that are essentially human. Human antibodies comprise human $V_H$ and $V_L$ framework regions (FWs) as well as human complementary determining regions (CDRs). Preferably, the entire $V_H$ and $V_L$ variable domains are human or derived from human sequences. The antibodies can be obtained directly from human cells, for example by creating human hybridomas.

Alternatively, human antibodies can be obtained from transgenic animals into which unrearranged human Ig gene segments have been introduced and in which the endogenous mouse Ig genes have been inactivated (reviewed in Brüggemann and Taussig, 1997, *Curr. Opin. Biotechnol.* 8, 455-58). Preferred transgenic animals contain very large contiguous Ig gene fragments that are over 1 Mb in size (Mendez et al., 1997, *Nature Genet.* 15, 146-56) but human Mabs of moderate affinity can be raised from transgenic animals containing smaller gene loci (See, e.g., Wagner et al., 1994, *Eur. J. Immunol.* 42, 2672-81; Green et al., 1994, *Nature Genet.* 7, 13-21).

Human antibodies can also be obtained from libraries of antibody $V_H$ and/or $V_L$ domains. For example, a variable domain library can be obtained from human genomic sequences, or from peripheral blood lymphocyte expressing productively rearranged variable region genes. Furthermore, the human gene library can be synthetic. In one embodiment, variable domain libraries can be created which comprise human framework regions with one or more CDRs that are synthesized to include random or partial random sequences. For example, a human $V_H$ variable domain library can be created in which members are encoded by a human $V_H$ gene segment and a synthetic sequence for the CDR3H region (i.e., a synthetic $D_H$-$J_H$ gene segment). Likewise, a human $V_L$ variable domain may be encoded by a human $V_L$ gene segment and a synthetic sequence for the CDR3L region (i.e., a synthetic $J_L$ gene segment). In another embodiment, the human frameworks may be synthetic in that they have a consensus sequence derived from known human antibody sequences or subgroups of human sequences. In another alternative, one or more CDRs is obtained by amplification from human lymphocytes expressing rearranged variable domains and then recombined into a particular human framework.

In order to screen libraries of variable domains, it is common to employ phage display libraries wherein combinations of human heavy and light chain variable domains are displayed on the surface of filamentous phage (see, e.g., McCafferty et al., 1990, Nature 348, 552-54; Aujame et al., 1997, Human Antibodies 8, 155-68). Combinations of variable domains are typically displayed on filamentous phage in the form of Fabs or scFvs. The library is screened for phage bearing combinations of variable domains having desired antigen binding characteristics. Preferred single domain and variable domain combinations display high affinity for a selected antigen and little cross-reactivity to other related antigens. By screening very large repertoires of antibody fragments, (see e.g., Griffiths et al., 1994, EMBO J. 13, 3245-60) a good diversity of high affinity binding domains are isolated, with many expected to have sub-nanomolar affinities for the desired antigen.

In a physiological immune response, mutation and selection of expressed antibody genes leads to the production of antibodies having high affinity for their target antigen. The $V_H$ and $V_L$ domains incorporated into antibodies of the invention can similarly be subject to in vitro or in vivo mutation and screening procedures in order to modify affinity and/or specificity. Thus, binding domains of the invention include those for which binding characteristics have been improved by mutating CDRs and/or FW regions by direct mutation, methods of affinity maturation, or chain shuffling. It is understood that amino acid residues that are primary determinants of binding of single domain antibodies can be within Kabat defined CDRs, but may include other residues as well. For sVDs, residues important for antigen binding can also potentially include amino acids that would otherwise be located at the interface of a $V_H$-$V_L$ heterodimer. Typically, phage display is used to screen such mutants to identify those having the desired binding characteristics (see, e.g., Yang et al., J. Mol. Biol., 254: 392-403 (1995)). Mutations can be made in a variety of ways. One way is to randomize individual residues or combinations of residues so that in a population of otherwise identical sequences, all twenty amino acids or a subset thereof are found at particular positions. Alternatively, mutations may be induced over a range of CDR residues by error prone PCR methods (see, e.g., Hawkins et al., J. Mol. Biol., 226: 889-896 (1992)). For example, phage display vectors containing heavy and light chain variable region genes may be propagated in mutator strains of E. coli (see, e.g., Low et al., J. Mol. Biol., 250: 359-368 (1996)). These methods of mutagenesis are illustrative of the many methods known to one of skill in the art.

The invention also includes antigen binding proteins engineered from non-immunoglobulin scaffolds. For example, affibodies, which are derived from an immunoglobulin-binding domain of S. aureus protein A, possess no disulfide bonds and display reversible folding. Another example is fibronectin, which has an antibody-like structure and displays CDR-like loops. In contrast to antibodies, the fibronectin domain structure does not rely on disulfide bonds, yet displays high thermodynamic stability. Binding sites can be engineered into such scaffolds by, for example, diversifying codons at specified positions and screening for binding to a desired antigen. Codons can be randomized in loops, flat surfaces, cavities, or combinations of such locations. Further, peptide sequences can be inserted, usually in loops. Target-binding variants of resulting libraries can be isolated using selection of screening techniques that are well known in the art, not limited to phage display, ribosome display, bacteria or yeast surface display, and the like.

For antigen-binding proteins intended for therapy, various strategies are available for minimizing potential immunogenicity. Human scaffolds can be employed, and immunogenicity can be minimized, for example, by PEGylation or T-cell epitope engineering (i.e., minimizing T-cell reactive sequences).

Antigen-binding proteins from non-immunoglobulin scaffolds often can be produced more economically than immunoglobulin-type proteins. For example, the absence of disulfide bonds or free cysteines allows for expression of functional molecules in the reducing environment of the bacterial cytoplasm, which usually gives higher yields than periplasmic expression, and is more convenient than refolding in vitro. Binz, H. K. et al. (Nat. Biotech. 23:1257-68, 2005) discloses a variety of such antigen-specific binding proteins and techniques for their development.

As previously mentioned, a bispecific antibody can be provided as an alternative to coadministration. A variety of bispecific antibodies exist that are designed to incorporate various desirable characteristic. For example, bispecific diabodies have minimal size. Bispecific antibodies with four antigen binding sites (two for each binding specificity) have binding avidities for each target similar to those of corresponding natural antibodies. Certain bispecific antibodies incorporate Fc regions, thus retaining effector functions (e.g., complement dependent cytoxicity (CDC) and antibody dependent cellular cytoxicity (ADCC)) of natural antibodies. WO 01/90192 describes IgG-like tetravalent antibodies. WO2006/020258 describes a tetravalent antibody that incorporates two diabodies and retains effector functions. A variety of antigen-binding antibody fragments can be employed for antigen binding sites of the bispecific antibodies. These include, but are not limited to Fvs, scFvs, and sVDs.

Another means to block PDGFRβ-mediated signal transduction is via PDGFRβ-specific small molecule inhibitors. Small molecule refers to small organic compounds, such as heterocycles, peptides, saccharides, steroids, and the like. The small molecule modulators preferably have a molecular weight of less than about 2000 Daltons, preferably less than about 1000 Daltons, and more preferably less than about 500 Daltons. The compounds may be modified to enhance efficacy, stability, pharmaceutical compatibility, and the like. The small molecule inhibitors include but are not limited to small molecules that block the ATP binding domain, substrate binding domain, or kinase domain of receptor tyrosine kinases. In another embodiment, a small molecule inhibitor binds to the ligand binding domain of PDGFRβ and blocks receptor activation by a PDGFRβ ligand. Small molecule libraries can be screened for inhibitory activity using high-throughput biochemical, enzymatic, or cell based assays. The assays can be formulated to detect the ability of a test compound to inhibit PDGFRβ, but not PDGFRα.

Antisense oligodeoxynucleotides, antisense RNAs and small inhibitory RNAs (siRNA) provide for targeted degradation of mRNA, thus preventing the translation of proteins. Accordingly, expression of PDGFRβ can be inhibited. The ability of antisense oligonucleotides to suppress gene expression was discovered more than 25 yr ago (Zamecnik and Stephenson, *Proc. Natl. Acad. Sci. USA.* 75:280-284 (1978)). Antisense oligonucleotides base pair with mRNA and pre-mRNAs and can potentially interfere with several steps of RNA processing and message translation, including splicing, polyadenylation, export, stability, and protein translation (Sazani and Kole, *J. Clin. Invest.* 112:481-486 (2003)). However, the two most powerful and widely used antisense strategies are the degradation of mRNA or pre-mRNA via RNaseH and the alteration of splicing via targeting aberrant splice junctions. RNaseH recognizes DNA/RNA heteroduplexes and cleaves the RNA approximately midway between the 5' and 3' ends of the DNA oligonucleotide.

Innate RNA-mediated mechanisms can regulate mRNA stability, message translation, and chromatin organization (Mello and Conte *Nature.* 431:338-342, 2004). Furthermore, exogenously introduced long double-stranded RNA (dsRNA) is an effective tool for gene silencing in a variety of lower organisms. However, in mammals, long dsRNAs elicit highly toxic responses that are related to the effects of viral infection and interferon production (Williams, *Biochem. Soc. Trans.* 25:509-513, 1997). To avoid this, Elbashir and colleagues (Elbashir et al., *Nature* 411:494-498, 2001) initiated the use of siRNAs composed of 19-mer duplexes with 5' phosphates and 2 base 3' overhangs on each strand, which selectively degrade targeted mRNAs upon introduction into cells.

The action of interfering dsRNA in mammals usually involves two enzymatic steps. First, Dicer, an RNase III-type enzyme, cleaves dsRNA to 21-23-mer siRNA segments. Then, RNA-induced silencing complex (RISC) unwinds the RNA duplex, pairs one strand with a complementary region in a cognate mRNA, and initiates cleavage at a site 10 nucleotides upstream of the 5' end of the siRNA strand (Hannon, *Nature.* 418:244-251, 2002). Short, chemically synthesized siRNAs in the 19-22 mer range do not require the Dicer step and can enter the RISC machinery directly. It should be noted that either strand of an RNA duplex can potentially be loaded onto the RISC complex, but the composition of the oligonucleotide can affect the choice of strands. Thus, to attain selective degradation of a particular mRNA target, the duplex should favor loading of the antisense strand component by having relatively weak base pairing at its 5' end (Khvorova, *Cell.* 115:209-216, 2003). Exogenous siRNAs can be provided as synthesized oligonucleotides or expressed from plasmid or viral vectors (Paddison and Hannon, *Curr. Opin. Mol. Ther.* 5:217-224, 2003). In the latter case, precursor molecules are usually expressed as short hairpin RNAs (shRNAs) containing loops of 4-8 nucleotides and stems of 19-30 nucleotides; these are then cleaved by Dicer to form functional siRNAs.

Other means to inhibit PDGFRβ-mediated signal transduction include, but are not limited to, PDGF mimetics that bind to but do not activate the receptor, and expression of genes or polynucleotides that reduce PDGFRβ levels or activity such as triple helix inhibitors and dominant negative PDGFRβ mutants.

RTK antagonists (i.e., PDGFRβ-specific antagonists, VEGFR antagonists) to be used according to the present invention exhibit one or more of following properties:

1) The antagonist binds to the external domain of an RTK (i.e., PDGFRβ, VEGFR) and inhibits ligand binding. Inhibition can be determined, for example, by a direct binding assay using purified or membrane bound receptor.

2) The antagonist neutralizes the receptor. Binding of a ligand to an external, extracellular domain of a receptor (e.g., PDGF-BB or PDGF-DD to PDGFRβ; VEGF or P1GF to VEGFR) stimulates autophosphorylation of the receptor and downstream signaling molecules, including MAPK, Akt, and IRS-1. Neutralization of a receptor includes inhibition, diminution, inactivation and/or disruption of one or more of these activities normally associated with signal transduction. Neutralization can be determined in vivo, ex vivo, or in vitro using, for example, tissues, cultured cell, or purified cellular components. Thus, neutralizing PDGFRβ and/or VEGFR has various effects, including inhibition, diminution, inactivation and/or disruption of growth (proliferation and differentiation), angiogenesis (blood vessel recruitment, invasion, and metastasis), and cell motility and metastasis (cell adhesion and invasiveness).

One measure of receptor neutralization is inhibition of the tyrosine kinase activity of the receptor. Tyrosine kinase inhibition can be determined using well-known methods; for example, by measuring the autophosphorylation level of recombinant kinase receptor, and/or phosphorylation of natural or synthetic substrates. Thus, phosphorylation assays are useful in determining neutralizing antibodies in the context of the present invention. Phosphorylation can be detected, for example, using an antibody specific for phosphotyrosine in an ELISA assay or on a western blot. Some assays for tyrosine kinase activity are described in Panek et al., *J. Pharmacol. Exp. Thera.* 283: 1433-44 (1997) and Batley et al., *Life Sci.* 62:143-50 (1998). Antibodies of the invention cause a decrease in tyrosine phosphorylation of PDGFRβ of at least about 30%, at least about 50%, at least about 75%, preferably at least about 85%, and more preferably at least about 90% in cells that respond to ligand.

Another measure of receptor neutralization is inhibition of phosphorylation of downstream substrates of the receptor or other signal transduction components. Accordingly, the level of phosphorylation of MAPK, Akt, IRS-1, and other cellular components can be measured. The decrease in phosphorylation is at least about 40%, and can be at least about 60%, or at least about 80%.

In addition, methods for detection of protein expression can be utilized to determine receptor neutralization, wherein the proteins being measured are regulated by the receptor tyrosine kinase activity. These methods include immunohistochemistry (IHC) for detection of protein expression, fluorescence in situ hybridization (FISH) for detection of gene amplification, competitive radioligand binding assays, solid matrix blotting techniques, such as Northern and Southern blots, reverse transcriptase polymerase chain reaction (RT-PCR) and ELISA. See, e.g., Grandis et al., *Cancer,* 78:1284-92 (1996); Shimizu et al., *Japan Cancer Res.,* 85:567-71 (1994); Sauter et al., *Am. J. Path.,* 148:1047-53 (1996); Collins, *Glia* 15:289-96 (1995); Radinsky et al., *Clin. Cancer Res.* 1:19-31 (1995); Petrides et al., *Cancer Res.* 50:3934-39 (1990); Hoffmann et al., *Anticancer Res.* 17:4419-26 (1997); Wikstrand et al., *Cancer Res.* 55:3140-48 (1995). Ex vivo assays can also be utilized to determine receptor neutralization. For example, receptor tyrosine kinase inhibition can be observed by mitogenic assays using cell lines stimulated with receptor ligand in the presence and absence of inhibitor.

Another method involves testing for inhibition of growth of RTK-expressing tumor cells or cell lines transfected to express PDGFRβ. Inhibition can also be observed using tumor models, for example, human tumor cells injected into a mouse.

The antagonists of the present invention are not limited by any particular mechanism of receptor neutralization. The antagonists of the present invention can bind externally to the cell surface receptor, block binding of ligand and subsequent signal transduction mediated via the receptor-associated tyrosine kinase, and prevent phosphorylation of the PDGFRβ and other downstream proteins in the signal transduction cascade.

3) The antagonist down modulates the receptor. The amount of RTK present on the surface of a cell depends on receptor protein production, internalization, and degradation. The amount of receptor present on the surface of a cell can be measured indirectly, by detecting internalization of the receptor or a molecule bound to the receptor. For example, receptor internalization can be measured by contacting cells that a receptor-specific labeled antibody. Membrane-bound antibody is then stripped, collected and counted. Internalized antibody is determined by lysing the cells and detecting label in the lysates.

Another way is to directly measure the amount of the receptor present on the cell following treatment with an anti-RTK antibody or other substance, for example, by fluorescence-activated cell-sorting analysis of cells stained for surface expression of the RTK. Stained cells are incubated at 37° C. and fluorescence intensity measured over time. As a control, part of the stained population can be incubated at 4° C. (conditions under which receptor internalization is halted).

Cell surface RTK can be detected and measured using a different antibody that is specific for PDGFRβ and that does not block or compete with binding of the antibody being tested. In certain embodiments, the reduction in cell surface RTK is at least about 50%, or at least about 75%, or at least about 90% in response to treatment with an RTK antagonist. A significant decrease can usually be observed in as little as four hours.

Another measure of down-modulation is reduction of the total receptor protein present in a cell, and reflects degradation of internal receptors. Accordingly, treatment of cells (particularly cancer cells) with antibodies of the invention results in a reduction in total cellular RTK. In certain embodiments, the reduction in cell surface RTK is at least about 50%, or at least about 75%, or at least about 90% in response to treatment with an RTK antagonist.

Antibody specificity refers to selective recognition of the antibody for a particular epitope of an antigen. Natural antibodies, for example, are monospecific. Bispecific antibodies (BsAbs) are antibodies which have two different antigen-binding specificities or sites. Where an antigen-binding protein has more than one specificity, the recognized epitopes may be associated with a single antigen or with more than one antigen.

Preferably, the antibodies of the present invention bind receptor at least as strongly as a natural ligand to that receptor. Affinity, represented by the equilibrium constant for the dissociation of an antigen with an antibody (Kd), measures the binding strength between an antigenic determinant and an antibody binding site. Avidity is the measure of the strength of binding between an antibody with its antigen. Avidity is related to both the affinity between an epitope with its antigen binding site on the antibody, and the valence of the antibody. Valency refers to the number of antigen binding sites which an immunoglobulin has for a particular epitope. For example, a monovalent antibody has one binding site for a particular epitope. An antigenic determinant, or epitope, is the site on an antigen at which a given antibody binds. Typical values of K are $10^5$ to $10^{11}$ liters/mol. Any K less than $10^4$ liters/mol is considered to indicate binding which is nonspecific. The reciprocal of K is designated as $K_d$. ($K_d$ also may be referred to as the dissociation constant). The lesser the value of the $K_d$, the stronger the binding strength between an antigenic determinant and the antibody binding site.

Antibodies of the invention include any antibody that binds specifically to PDGFRβ and reduces or inhibits receptor mediated signal transduction. In certain embodiments, the antibodies bind to their respective receptors with a $K_d$ that is less than about $10^{-8}$ $M^{-1}$ or less than about $10^{-9}$ $M^{-1}$ or less than about $3 \times 10^{-10}$ $M^{-1}$. Non-limiting examples particular PDGFRβ-specific antibodies are disclosed and/or exemplified herein. The nucleic acid and amino acid sequences of two particular antibodies of the invention, 1B3 and 2C5, are described in Table 1.

In a preferred embodiment, one, two, three, four, five, or all six complementarity-determining regions (CDR) of the antibody has a sequence selected from any one of the CDRs of 1B3. In an alternatively preferred embodiment, one, two, three, four, five, or all six complementarity-determining regions (CDR) of the antibody has a sequence selected from the group consisting of any one of the CDRs of 2C5.

The antibodies of the present invention, in another preferred embodiment, have a heavy chain variable region sequence substantially identical to the heavy chain variable region of 1B3 or 2C5 and/or a light chain variable region sequence substantially identical to the light chain variable region of 1B3 or 2C5. By "substantially identical" it is meant that the amino acid sequences are at least 80%, 85%, 90%, 95%, 98%, or 99% identical to the reference sequences.

In an embodiment or the invention, a PDGFRβ-specific antibody includes a heavy chain variable domain comprising the amino acid sequence of SEQ ID NO:18 and a light chain comprising the amino acid sequence of SEQ ID NO:26. In another embodiment or the invention, a PDGFRβ-specific antibody includes a heavy chain variable domain comprising the amino acid sequence of SEQ ID NO:2 and a light chain comprising the amino acid sequence of SEQ ID NO:10. PDGFRβ-specific antibodies of the invention further include those that compete with the aforementioned antibodies (i.e., that bind to the same or overlapping epitopes).

The present invention also include antibodies with amino acid sequences substantially the same as the amino acid sequence of the variable or hypervariable regions of the aforementioned antibodies. Substantially the same amino acid sequence is defined herein as a sequence with at least 80%, or at least about 90%, or at least about 95% homology or identity to another amino acid sequence, as determined by the FASTA search method in accordance with Pearson and Lipman (*Proc. Natl. Acad. Sci. USA* 85: 2444-8 (1998)). It is to be expected that a variety of substitutions can be made in framework regions, particularly in view of the frequent mutations in framework regions that are observed to result from in vivo mutation and selection. However, it is also expected that mutations at certain CDR positions will also be allowed. For example, not all CDR amino acids are in direct contact with antigen. Amino acid changes, particularly conservative changes, at non-contact CDR positions are expected to affect binding affinity, potentially for the better, rather than to abrogate binding altogether. Current technology allows one of skill in the art to easily make sequence variations by design or at random, and test their results. Conservative amino acid substitution is defined as a change in the amino acid composition by way of changing one or a few amino acids of a peptide, polypeptide or protein, or fragment thereof. The substitution is of amino acids with generally similar properties (e.g., acidic, basic, aromatic, size, positively or negatively charged, polarity, non-polarity) such that the substitutions do not substantially alter peptide, polypeptide or protein characteristics (e.g., charge, isoelectric point, affinity, avidity, conformation, solubility) or activity. Typical substitutions that may be performed for such conservative amino acid substitution may be among the groups of amino acids as follows:

- glycine (G), alanine (A), valine (V), leucine (L) and isoleucine (I);
- aspartic acid (D) and glutamic acid (E);
- alanine (A), serine (S) and threonine (T);
- histidine (H), lysine (K) and arginine (R):
- asparagine (N) and glutamine (Q);
- phenylalanine (F), tyrosine (Y) and tryptophan (W)

According to the invention, the PDGFRβ-specific antibodies can be administered alone, along with anti-VEGFR antibodies, or may be bispecific antibodies that bind to both PDGFRβ and VEGFR. Examples of VEGFR-specific antibodies are also provided. As discussed above with respect to PDGFRβ-specific antibodies, the disclosed VEGFR antibodies are non-limiting examples.

The invention also provides antibodies which bind to certain domains of PDGFRβ. Antibodies which bind to domains 1 and 2, antibodies that bind to domain 1, and antibodies which bind to domain 2 of PDGFRβ are within the scope of the invention. 2C5 is an example of an antibody which binds to domain 2, and domains 1 and 2, of PDGFRβ.

Each variable domain of the antibodies of the present invention may be a complete immunoglobulin heavy or light chain variable domain, or it may be a functional equivalent or a mutant or derivative of a naturally occurring domain, or a synthetic domain constructed, for example, in vitro using a technique such as one described in WO 93/11236 (Medical Research Council/Griffiths et al.). For instance, it is possible to incorporate domains corresponding to antibody variable domains which include amino acid substitutions, deletions, additions, amino terminal truncations and carboxy-terminal truncations such that these mutations provide for proteins or protein fragments that retain antigen-binding activity. The important characterizing feature is the ability of each variable domain to associate with a complementary variable domain to form an antigen binding site.

The antibodies and fragments of the invention may be linked or fused to additional amino acid residues. Such amino acid residues can be a peptide tag, perhaps to facilitate isolation. Other amino acid residues for homing of the antibodies to specific organs or tissues are also contemplated.

In another aspect of the invention, the antibodies or antibody fragments can be chemically or biosynthetically linked to anti-tumor agents or detectable signal-producing agents, particularly when the antibody is internalized. Anti-tumor agents linked to an antibody include any agents which destroy or damage a tumor to which the antibody has bound or in the environment of the cell to which the antibody has bound. For example, an anti-tumor agent is a toxic agent such as a chemotherapeutic agent or a radioisotope. Suitable chemotherapeutic agents are known to those skilled in the art and include anthracyclines (e.g., daunomycin and doxorubicin), methotrexate, vindesine, neocarzinostatin, cis-platinum, chlorambucil, cytosine arabinoside, 5-fluorouridine, melphalan, ricin and calicheamicin. The chemotherapeutic agents are conjugated to the antibody using conventional methods (See, e.g., Hermentin and Seiler, Behring Inst. Mitt. 82:197-215 (1988)).

Detectable signal-producing agents are useful in vivo and in vitro for diagnostic purposes. The signal producing agent produces a measurable signal which is detectable by external means, usually the measurement of electromagnetic radiation. For the most part, the signal producing agent is an enzyme or chromophore, or emits light by fluorescence, phosphorescence or chemiluminescence. Chromophores include dyes which absorb light in the ultraviolet or visible region, and can be substrates or degradation products of enzyme catalyzed reactions.

The invention further contemplates antibodies to which target or reporter moieties are linked. Target moieties are first members of binding pairs. Anti-tumor agents, for example, are conjugated to second members of such pairs and are thereby directed to the site where the antigen-binding protein is bound. A common example of such a binding pair is avidin and biotin. In a preferred embodiment, biotin is conjugated to an antigen-binding protein of the invention, and thereby provides a target for an anti-tumor agent or other moiety which is conjugated to avidin or streptavidin. Alternatively, biotin or another such moiety is linked to an antigen-binding protein of the invention and used as a reporter, for example in a diagnostic system where a detectable signal-producing agent is conjugated to avidin or streptavidin.

Suitable radioisotopes for use as anti-tumor agents are also known to those skilled in the art. For example, 131I or 211At is used. These isotopes are attached to the antibody using conventional techniques (See, e.g., Pedley et al., Br. J. Cancer 68:69-73 (1993)). Alternatively, the anti-tumor agent which is attached to the antibody is an enzyme which activates a prodrug. In this way, a prodrug is administered which remains in its inactive form until it reaches the tumor site where it is converted to its cytotoxin form once the antibody complex is administered. In practice, the antibody-enzyme conjugate is administered to the patient and allowed to localize in the region of the tissue to be treated. The prodrug is then administered to the patient so that conversion to the cytotoxic drug occurs in the region of the tissue to be treated. Alternatively, the anti-tumor agent conjugated to the antibody is a cytokine such as interleukin-2 (IL-2), interleukin-4 (IL-4) or tumor necrosis factor alpha (TNF-α). The antibody targets the cytokine to the tumor so that the cytokine mediates damage to or destruction of the tumor without affecting other tissues. The cytokine is fused to the antibody at the DNA level using conventional recombinant DNA techniques.

The present invention also provides isolated polynucleotides encoding the antibodies, or fragments thereof, described previously. The invention includes nucleic acids having sequences encoding PDGFRβ-specific antibodies and antigen-binding fragments comprising one, two, three, four, five and/or all six CDRs as set forth in Table 1.

Accordingly, the invention provides nucleic acids that specifically hybridize (or specifically bind) under stringent hybridization conditions to SEQ ID NO:1, SEQ ID NO:9, SEQ ID NO:17, and SEQ ID NO:25. Also contemplated are nucleic acids that would specifically bind to the aforementioned sequences but for the degeneracy of the nucleic acid code. The nucleic acids can be of sufficient length to encode a complete protein (e.g., a complete $V_H$ or $V_L$) or a fragment thereof.

Hybridization under stringent conditions refers to conditions under which a probe will hybridize preferentially to its target subsequence, and to a lesser extent to, or not at all to, other sequences. It also will be understood that stringent hybridization and stringent hybridization wash conditions in the context of nucleic acid hybridization experiments such as southern and northern hybridizations are sequence dependent, and are different under different environmental parameters. It is well known in the art to adjust hybridization and wash solution contents and temperatures such that stringent hybridization conditions are obtained. Stringency depends on such parameters as the size and nucleotide content of the probe being utilized. See Sambrook et al., 1989, Molecular Cloning—A Laboratory Manual (2nd ed.) Vol. 1-3, Cold Spring Harbor Laboratory, Cold Spring Harbor Press, NY, and other sources for general descriptions and examples. Another guide to the hybridization of nucleic acids is found in Tijssen, 1993, Laboratory Techniques in Biochemistry and Molecular Biology—Hybridization with Nucleic Acid Probes, part I, chapter 2, Overview of principles of hybridization and the strategy of nucleic acid probe assays, Elsevier, N.Y.

Preferred stringent conditions are those that allow a probe to hybridize to a sequence that is more than about 90% complementary to the probe and not to a sequence that is less than about 70% complementary. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2 times SSC wash at 65° C. for 15 minutes (see, Sambrook et al., 1989). Often, a high stringency wash is preceded by a low stringency wash to remove background probe signal. An example of a medium stringency wash for a duplex of, e.g., more than 100 nucleotides, is 1 times SSC at 45° C. for 15 minutes. An example of a low stringency wash for a duplex of, e.g., more than 100 nucleotides, is 4-6 times SSC at 40° C. for 15 minutes. In general, a signal to noise ratio that is two times (or higher) that observed for an unrelated probe in the particular hybridization assay indicates detection of a specific hybridization.

Nucleic acids which do not hybridize to each other under stringent conditions are still substantially identical if the polypeptides which they encode are substantially identical. This occurs, e.g., when a nucleic acid is created using the maximum codon degeneracy permitted by the genetic code. Accordingly, nucleotide sequences of the invention include sequences of nucleotides that are at least about 70%, preferably at least about 80%, and more preferably at least about 90% identical to SEQ ID NO:1, SEQ ID NO:9, SEQ ID NO:17, or SEQ ID NO:25. The present invention also provides recombinant vectors containing a nucleic acid of the invention. The vector may be an expression vector, wherein the nucleic acid is operably linked to a control sequence such as a promoter and optionally an enhancer sequence. A variety of expression vectors have been developed for the efficient synthesis of antibody polypeptides in prokaryotic and eukaryotic systems, including but not limited to yeast and mammalian cell culture systems.

Any suitable expression vector can be used. The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters of SV40, and other sequences known to control the expression of genes of prokaryotic or eukaryotic cells and their viruses or combinations thereof.

A selectable marker is a gene which encodes a protein necessary for the survival or growth of transformed host cells grown in a selective culture medium. Typical selectable markers encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for Bacilli. A particularly useful selectable marker confers resistance to methotrexate. For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin (1980) *Proc. Natl. Acad. Sci. USA* 77, 4216. The transformed cells are then exposed to increased levels of methotrexate. This leads to the synthesis of multiple copies of the DHFR gene, and, concomitantly, multiple copies of other DNA comprising the expression vectors, such as the DNA encoding the antibody or antibody fragment.

Where it is desired to express a gene construct in yeast, an example of a suitable selection gene for use in yeast is the trp1 gene present in the yeast plasmid, YRp7. Stinchcomb et al. (1979) *Nature,* 282, 39; Kingsman et al. (1979) *Gene* 7, 141. The trp1 gene provides a selection marker for a mutant strain of yeast lacking the ability to grow in tryptophan, for example, ATCC No. 44076 or PEP4-1. Jones (1977) *Genetics* 85, 12. The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene. An example of a vector useful in yeast is the 2μ plasmid.

Examples of prokaryotic cloning vectors include plasmids from *E. coli*, such as colE1, pCR1, pBR322, pMB9, pUC, pKSM, and RP4. Prokaryotic vectors also include derivatives of phage DNA such as M13 and other filamentous single-stranded DNA phages. Ceratin antibodies are conveniently produced in *E. coli* using DNA constructs which comprise bacterial secretion signal sequences at the start of each polypeptide chain. A variety of bacterial signal sequences are known in the art. A preferred signal sequence is from the pelB gene of *Erwinia carotovora*.

Suitable vectors for expression in mammalian cells include well-known derivatives of SV40, adenovirus, retrovirus-derived DNA sequences and shuttle vectors derived from combination of functional mammalian vectors, such as those described above, and functional plasmids and phage DNA. The DNA fragments coding for the antibodies can be cloned, e.g., into vectors employing human cytomegalovirus (HCMV) promoters and enhancers for high level expression in mammalian cells. (See, e.g., Bendig, et al., U.S. Pat. No. 5,840,299; Maeda, et al. (1991) *Hum. Antibod. Hybridomas*

2, 124-34; P. J. Southern and P. Berg, *J. Mol. Appl. Genet.* 1: 327-41 (1982); Subramani et al., *Mol. Cell. Biol.* 1: 854-64 (1981); Kaufmann and Sharp, "Amplification And Expression of Sequences Cotransfected with a Modular Dihydrofolate Reductase Complementary DNA Gene," *J. Mol. Biol.* 159: 601-21 (1982); Kaufmann and Sharp, *Mol. Cell. Biol.* 159: 601-64 (1982); Scahill et al., "Expression And Characterization Of The Product Of A Human Immune Interferon DNA Gene In Chinese Hamster Ovary Cells," *Proc. Nat'l Acad. Sci. USA* 80, 4654-59 (1983); Urlaub and Chasin, *Proc. Nat'l Acad. Sci. USA* 77: 4216-20, (1980).

The present invention also provides recombinant host cells containing the recombinant or expression vectors previously described. Cell lines of particular preference are selected based on high level of expression, constitutive expression of protein of interest and minimal contamination from host proteins. Useful prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRCl, *Pseudomonas, Bacillus*, such as *Bacillus subtilis*, and *Streptomyces*. Mammalian cell lines available as hosts for expression are well known in the art and include many immortalized cell lines, such as but not limited to, COS-7 cells, Chinese Hamster Ovary (CHO) cells, Baby Hamster Kidney (BHK) cells, PER.C6 cells, and many others including cell lines of lymphoid origin such as lymphoma, myeloma, or hybridoma cells. Suitable additional eukaryotic cells include yeast and other fungi.

Transformed host cells are cultured by methods known in the art in a liquid medium containing assimilable sources of carbon, e.g. carbohydrates such as glucose or lactose, nitrogen, e.g. amino acids, peptides, proteins or their degradation products such as peptones, ammonium salts or the like, and inorganic salts, e.g. sulfates, phosphates and/or carbonates of sodium, potassium, magnesium and calcium. The medium furthermore contains, for example, growth-promoting substances, such as trace elements, for example iron, zinc, manganese and the like.

The invention also provides a method of producing an antibody comprising culturing the above host cells under conditions permitting expression of the antibody. Following expression in a host cell maintained in a suitable medium, the antibodies may be isolated from the medium, and purified by methods known in the art.

This invention further provides a pharmaceutical composition comprising the antibody, nucleic acid, vector or host cell of this invention and a pharmaceutically acceptable carrier.

The present invention also relates to methods for treating or inhibiting growth of a tumors, for treating or controlling an angiogenesis-dependent condition in a mammal (such as, for example, tumor growth), or for treating an angiogenic disease, which comprise administering a PDGFRβ-specific antagonist. In one embodiment, the antagonist blocks PDGFRβ-mediated stimulation of tumor cells. In another embodiment, the antagonist functions to inhibit or prevent angiogenesis, thereby treating or controlling an angiogenesis-dependent condition. Typically, vascular endothelium is stimulated in a paracrine fashion by growth factors from other sources (e.g., tumor cells). Accordingly, the PDGFRβ antagonists are effective for treating subjects with vascularized tumors or neoplasms.

"Treating" a disease includes: (1) preventing the disease from occurring in a mammal which may be predisposed to the disease but does not yet experience or display symptoms of the disease; e.g., prevention of the outbreak of the clinical symptoms; (2) inhibiting the disease, e.g., arresting or retarding its development; or (3) relieving the disease, e.g., causing regression of the symptoms of the disease.

Tumors which may be treated include primary tumors and metastatic tumors, as well as refractory tumors. Refractory tumors include tumors that fail to respond or are resistant to treatment with chemotherapeutic agents alone, antibodies alone, radiation alone or combinations thereof. Refractory tumors also encompass tumors that appear to be inhibited by treatment with such agents, but recur up to five years, sometimes up to ten years or longer after treatment is discontinued.

PDGFRβ-specific antagonists are administered in dosages and dose frequencies sufficient to substantially saturate the target receptor or its ligand. Substantial saturation is at least about 50%, or at least about 80%, or at least about 95% saturation of targeted receptors. The PDGFRβ-specific antagonist is administered at frequency sufficient to maintain substantial saturation for at least about 50%, or at least about 70%, or at least about 90% of the interval between doses. In an embodiment of the invention, the PDGFRβ-specific antagonist is an antibody. For therapy, a dose regimen is from about 5 mg/m$^2$ to about 700 mg/m$^2$. In another embodiment, the dose regimen is from about 10 mg/m$^2$ to about 250 mg/m$^2$. The appropriate dose and schedule can be determined readily by one of skill in the art, for example, using concentrations required to achieve receptor saturation or neutralization in vitro, or by analysis of serum concentration of the antagonist.

In an embodiment of the invention, a PDGFRβ-specific antagonist is administered with a chemotherapeutic agent. The chemotherapeutic agents known in the art or being evaluated can be grouped in to classes based on their target or mode of action. For example, alkylating agents include, but are not limited to, cisplatin, cyclophosphamide, melphalan, and dacarbazine. Examples of anti-metabolites include, but not limited to, doxorubicin, daunorubicin, and paclitaxel, gemcitabine, and topoisomerase inhibitors irinotecan (CPT-11), aminocamptothecin, camptothecin, DX-8951f, and topotecan (topoisomerase I) and etoposide (VP-16) and teniposide (VM-26) (topoisomerase II). Other suitable chemotherapeutic agents are known to those skilled in the art and include, methotrexate, vindesine, neocarzinostatin, chlorambucil, cytosine arabinoside, 5-fluorouridine, melphalan, ricin and calicheamicin. The PDGFRβ antagonist and chemotherapeutic agent are administered to a patient in amounts effective to inhibit angiogenesis and/or reduce tumor growth. The PDGFRβ antagonist can also to be administered in combination with other treatment regimes, for example, with treatments such as radiation therapy. For radiation, the source can be either external (external beam radiation therapy—EBRT) or internal (brachytherapy—BT) to the patient being treated.

The dose of anti-neoplastic agent administered depends on numerous factors, including, for example, the type of agent, the type and severity tumor being treated and the route of administration of the agent. It should be emphasized, however, that the present invention is not limited to any particular dose.

In an embodiment of the invention, a PDGFRβ-specific antagonist is administered in combination with a VEGFR antagonist. Examples of VEGFR antagonists include antibodies that bind to VEGFR2/KDR, such as IMC-2C6 (nucleotide and amino acids sequences of $V_H$: SEQ ID NOS:33 and 34; nucleotide and amino acid sequences of $V_L$: SEQ ID NOS:35 and 36) (see, WO 03/075840) and IMC-1121 (nucleotide and amino acids sequences of $V_H$: SEQ ID NOS:33 and 34; nucleotide and amino acid sequences of $V_L$: SEQ ID NOS:37 and 38) (see, WO 03/075840). Examples of antibodies that bind to VEGFR1/Flt-1 include 6.12 (nucleotide and amino acids sequences of $V_H$: SEQ ID NOS:39 and 40; nucleotide and amino acid sequences of $V_L$: SEQ ID NOS:41 and 42) and IMC-18F1 (nucleotide and amino acids sequences of $V_H$: SEQ ID NOS:43 and 44; nucleotide and amino acid sequences of $V_L$: SEQ ID NOS:45 and 46). An example of an antibody specific for VEGF is Avastin®.

As disclosed above for PDGFRβ-specific antibodies, a VEGFR antagonist reduces or inhibits signal transduction mediated by a VEGF receptor. Mechanisms of inhibition include, but are not limited to, ligand blocking, receptor dimer or multimer formation, receptor internalization, inhibition of enzymatic activity (e.g., autophosphorylation, modification of receptor substrates), and the like.

In certain embodiments, antibodies of the instant invention have dual specificity and are capable of binding to two different antigens simultaneously. The different antigens can be located on different cells or on the same cell. Cross-linking of antigen can be confirmed in vitro, for example by providing a solid support to which a first antigen has been bound, adding a bispecific antibody specific for the first antigen, adding a second antigen for which the binding protein is also specific, and detecting the presence of bound second antigen.

Preferred antibodies of the invention are capable of blocking the interaction between two receptors and their respective ligands. For example, an antibody specific for PDGFRβ and KDR inhibits PDGF-BB induced cell activation as well as VEGF or P1GF induced cell migration. Compared to antibodies that are monospecific, bispecific antibodies can be more potent inhibitors of cellular function.

In an aspect of the invention, a PDGFRβ antagonist is coadministered with a VEGFR antagonist. The method is effective for treating a solid or non-solid tumor, including one that is not vascularized, or is not yet substantially vascularized.

Tumors and neoplasms that can be treated with a PDGFRβ antagonist alone or in combination with a VEGFR antagonist include, for example, malignant tumors and neoplasms, such as blastomas, carcinomas or sarcomas, and highly vascular tumors and neoplasms. Cancers that may be treated by the methods of the present invention include, for example, cancers of the brain, genitourinary tract, lymphatic system, stomach, renal, colon, larynx and lung and bone. Non-limiting examples further include epidermoid tumors, squamous tumors, such as head and neck tumors, colorectal tumors, prostate tumors, breast tumors, lung tumors, including lung adenocarcinoma and small cell and non-small cell lung tumors, pancreatic tumors, thyroid tumors, ovarian tumors, and liver tumors. The compositions are also used for treatment of vascularized skin cancers, including squamous cell carcinoma, basal cell carcinoma, and skin cancers that can be treated by suppressing the growth of malignant keratinocytes, such as human malignant keratinocytes. Other cancers that can be treated include Kaposi's sarcoma, CNS neoplasms (neuroblastomas, capillary hemangioblastomas, meningiomas and cerebral metastases), melanoma, gastrointestinal and renal carcinomas and sarcomas, rhabdomyosarcoma, glioblastoma, including glioblastoma multiforme, and leiomyosarcoma.

Examples of non-solid tumors include leukemia, multiple myeloma and lymphoma. Some examples of leukemias include acute myelogenous leukemia (AML), chronic myelogenous leukemia (CML), acute lymphocytic leukemia (ALL), chronic lymphocytic leukemia (CLL), erythrocytic leukemia or monocytic leukemia. Some examples of lymphomas include Hodgkin's and non-Hodgkin's lymphoma.

The compositions of the present invention can also be used to treat or prevent pathologic conditions characterized by excessive angiogenesis, involving, for example, vascularization and/or inflammation, such as atherosclerosis, rheumatoid arthritis (RA), neovascular glaucoma, proliferative retinopathy including proliferative diabetic retinopathy, macular degeneration, hemangiomas, angiofibromas, and psoriasis. Other non-limiting examples of non-neoplastic angiogenic disease are retinopathy of prematurity (retrolental fibroplastic), corneal graft rejection, insulin-dependent diabetes mellitus, multiple sclerosis, myasthenia gravis, Chron's disease, autoimmune nephritis, primary biliary cirrhosis, acute pancreatitis, allograph rejection, allergic inflammation, contact dermatitis and delayed hypersensitivity reactions, inflammatory bowel disease, septic shock, osteoporosis, osteoarthritis, cognition defects induced by neuronal inflammation, Osler-Weber syndrome, restinosis, and fungal, parasitic and viral infections, including cytomegaloviral infections.

The identification of such disease is well within the ability and knowledge of one skilled in the art. For example, human individuals who are either suffering from a clinically significant neoplastic or angiogenic disease or who are at risk of developing clinically significant symptoms are suitable for administration of a PDGFRβ antagonist, optionally in combination with a VEGFR antagonist. A clinician skilled in the art can readily determine, for example, by the use of clinical tests, physical examination and medical/family history, if an individual is a candidate for such treatment.

The present antagonist compositions can be administered for therapeutic treatments to a patient suffering from a tumor or angiogenesis associated pathologic condition in an amount sufficient to prevent, inhibit, or reduce the progression of the tumor or pathologic condition. Progression includes, e.g, the growth, invasiveness, metastases and/or recurrence of the tumor or pathologic condition. An amount adequate to accomplish this is defined as a therapeutically effective dose. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition. It should be noted, however, that the present invention is not limited to any particular dose.

Methods of administration to a mammal include, for example, oral, intravenous, intraperitoneal, subcutaneous, or intramuscular administration.

The PDGFRβ-specific and VEGFR-specific antibodies can be chemically or biosynthetically conjugated to other agents such as antineoplastic or anti-angiogenic agents for treatment of disease. Anti-tumor agents linked to an antibody include any agents which destroy or damage a tumor to which the antibody has bound or in the environment of the cell to which the antibody has bound. For example, an anti-tumor agent is a toxic agent such as a chemotherapeutic agent or a radioisotope. The chemotherapeutic agents are conjugated to the antibody using conventional methods (See, e.g., Hermentin and Seiler (1988) *Behring Inst. Mitt.* 82, 197-215), including by peptide and non-peptide linkers.

The PDGFRβ-specific antibodies of the invention can also be linked to detectable signal-producing agents useful in vivo and in vitro for diagnostic purposes. The signal producing agent produces a measurable signal which is detectable by external means, usually the measurement of electromagnetic radiation. For the most part, the signal producing agent is an enzyme or chromophore, or emits light by fluorescence, phosphorescence or chemiluminescence. Chromophores include dyes which absorb light in the ultraviolet or visible region, and can be substrates or degradation products of enzyme catalyzed reactions.

The invention further contemplates the use of such antibodies with treatment or diagnostic agents incorporated into secondary reagents. For example, one member of a binding pair is linked to the antibody of the invention. Anti-neoplastic agents, for example, are conjugated to second members of such pairs and are thereby directed to the site where the antibody is bound. In a preferred embodiment, biotin is conjugated to an antibody of the invention, and thereby provides a target for an anti-neoplastic agent or other moiety which is conjugated to avidin or streptavidin. Alternatively, biotin or another such moiety is linked to an antibody of the invention and used as a reporter, for example in a diagnostic system where a detectable signal-producing agent is conjugated to avidin or streptavidin.

A PDGFRβ antagonist of the invention, optionally combined with a VEGFR antagonist, can be administered in combination with one or more suitable adjuvants, such as, for example, cytokines (IL-10 and IL-13, for example) or other immune stimulators, such as, but not limited to, chemokine, tumor-associated antigens, and peptides. It should be appreciated, however, that administration of an antibody alone is sufficient to prevent, inhibit, or reduce the progression of the tumor in a therapeutically effective manner.

In certain embodiments, it can be desirable to administer an antibody of the invention that binds to an RTK and blocks ligand binding in combination with another antigen-binding protein that binds to ligand. Ligand binding antibodies are well known in the art, and include, e.g., anti-VEGF (Avastin®; bevacizumab).

According to the invention, coadministration of a PDGFRβ-specific antagonist and a VEGFR antagonist can be accompanied by administration of an anti-neoplastic agent such as a chemotherapeutic agent or a radioisotope. Examples of useful anti-neoplastic agents included those described above for coadministration with PDGFRβ-specific antagonists.

In a combination therapy, the PDGFRβ antagonist and the VEGFR antagonist can be coadministered on the same of different schedule, separately or together. Optionally, the antagonists can be combined into a single dosage. Optionally, the antagonists can be combined into a single active entity (e.g., a bispecific antibody). The PDGFRβ antagonist/VEGFR antagonist therapy is administered before, during, or after commencing therapy with another agent, as well as any combination thereof, i.e., before and during, before and after, during and after, or before, during and after commencing therapy with an anti-neoplastic agent. For example, for treatment of a tumor or neoplastic disease, PDGFRβ antagonist/VEGFR antagonist therapy can be administered between 1 and 30 days, preferably 3 and 20 days, more preferably between 5 and 12 days before commencing radiation therapy. According to the invention, chemotherapy or radiotherapy is administered concurrently with, prior to, or subsequent to the PDGFRβ antagonist/VEGFR antagonist therapy.

In the present invention, any suitable method or route can be used to administer antibodies of the invention, and optionally, to co-administer anti-neoplastic agents, receptor antagonists, or other pharmaceutical composition. For example, anti-neoplastic agent regimens utilized according to the invention include any regimen believed to be optimally suitable for the treatment of a patient's neoplastic condition. Different malignancies can require use of specific anti-tumor antibodies and specific anti-neoplastic agents, which will be determined on a patient to patient basis. Routes of administration include, for example, oral, intravenous, intraperitoneal, subcutaneous, or intramuscular administration. The dose of anti-neoplastic agent administered depends on numerous factors, including, for example, the type of neoplastic agent, the type and severity tumor being treated and the route of administration of the antineoplastic agent. It should be emphasized, however, that the present invention is not limited to any particular method or route of administration.

It is understood that antibodies of the invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers can further comprise minor amounts of auxiliary substances such as wetting or emulsifying agents, preservatives or buffers, which enhance the shelf life or effectiveness of the binding proteins. The compositions of the injection can, as is well known in the art, be formulated so as to provide quick, sustained or delayed release of the active ingredient after administration to the mammal.

The present invention also includes kits for inhibiting tumor growth and/or angiogenesis, comprising a therapeutically effective amount of a PDGFRβ-specific antagonist of the invention. In an embodiment of the invention, a kit further includes a VEGFR antagonist (e.g. an antagonist of VEGF, PlGF, VEGFR-1/Flt-1, VEGFR-2/Flk-1/KDR, or VEGFR3/Flt-4). The VEGF antagonists can be, for example, small molecules, ligand-binding receptor fragments, or antibodies. When the antagonist administered to a human is an antibody, human, humanized, or chimeric antibodies are preferred. The kits can further contain any suitable antagonist of, for example, another growth factor receptor involved in tumorigenesis or angiogenesis (e.g., EGFR, IGFR, NGFR, FGFR, etc, as described above). Alternatively, or in addition, the kits of the present invention can further comprise an anti-neoplastic agent. Examples of suitable anti-neoplastic agents in the context of the present invention have been described herein. The kits of the present invention can further comprise an adjuvant; examples have also been described above.

Also included within the scope of the present invention is use of the present antibodies in vivo and in vitro for investigative or diagnostic methods, which are well known in the art. The diagnostic methods include kits which contain antibodies of the present invention.

Accordingly, the present receptor binding antibodies thus can be used in vivo and in vitro for investigative, diagnostic, prophylactic, or treatment methods, which are well known in the art. Of course, it is to be understood and expected that variations in the principles of invention herein disclosed can be made by one skilled in the art and it is intended that such modifications are to be included within the scope of the present invention.

All references mentioned herein are incorporated by reference in their entirety.

EXAMPLES

The following examples further illustrate the invention, but should not be construed to limit the scope of the invention in any way. Detailed descriptions of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publications, including Sambrook, J. et al., (1989) Molecular Cloning: A Laboratory Manual, 2$^{nd}$ ed., Cold Spring Harbor Laboratory Press; and Coligan, J. et al. (1994) Current Protocols in Immunology, Wiley & Sons, Incorporated.

Phage display library. A human Fab phage display library containing 3.7×10¹⁰ clones (de Haard, H. J. et al., 1999, *J. Biol. Chem.* 274:18218-30) was used to screen for anti-mPDGFRβ antibodies following a previously described procedure (Lu, D. et al., 2002, *Int. J. Cancer* 97:393-9; Zhu, Z. et al., 1998, Cancer Res. 58:3209-14), using immobilized mPDGFRβ-Fc. Individual phage clones recovered after the 2$^{nd}$ and the 3$^{rd}$ rounds of selections were examined for binding to immobilized mPDGFRβ-Fc by ELISA. To produce soluble Fab, plasmids of individual binders were used to transform a nonsuppressor *Escherichia coli* host HB2151. The soluble Fab proteins were purified from periplasmic extracts by affinity chromatography using a Protein G column (Amersham Pharmacia Biotech, Piscataway, N.J.) following the manufacturer's protocol.

Quantitative receptor binding and blocking assays. In the binding assay, various amounts of 1B3 IgG or Fab were added to mPDGFRβ-coated plates (50 μl at 1 μg/ml), and incubated at RT for 1 h, after which the plates were washed 3 times with PBST. The plates were then incubated at RT for an additional 1 h with a goat anti-human-κ antibody-horse radish peroxidase (HRP) conjugate (Jackson ImmunoResearch, West Grove, Pa.). The plates were washed and developed as previously described (Lu, D. et al., 2002; Zhu, Z. et al., 1998). In the blocking assay, various amounts of purified antibodies were first mixed with a fixed amount of mPDGFRβ (50 ng at 0.5 μg/ml) and incubated at RT for 30 min. The mixture was then transferred to 96-well plates precoated with PDGF-BB (0.5 μg/ml) and incubated at RT for 1 h. After washing 3 times with PBST, the plates were incubated with a goat anti-human Fc antibody-HRP conjugate (Jackson ImmunoResearch) for 1 h, and developed as described (Lu, D. et al., 2002; Zhu, Z. et al., 1998; Loizos, N. et al., 2005). IC50, the antibody concentration that yielded 50% blockade of mPDGFRβ from binding to its ligand, was determined.

Antibody affinity determination. The binding kinetics of various Fab and IgG to mPDGFRβ were measured using a BIAcore 3000 biosensor (BIACORE, Inc., Uppsala, Sweden). Briefly, mPDGFRβ was immobilized onto a sensor chip and soluble antibodies were injected at concentrations ranging from 1.5 nM to 100 nM. Sensorgrams were obtained at each concentration and were evaluated using the program, BIA Evaluation 2.0. The affinity constant, Kd, was calculated from the ratio of dissociation rate (koff)/association rate (kon) (Lu, D. et al., 2002; Zhu, Z. et al., 1998; Loizos, N. et al., 2005).

Selection of human anti-mPDGFRβ antibodies. A total of 190 clones from the second round and 95 from the third round were randomly picked and tested for mPDGFRβ binding and blocking activities by both phage ELISA and soluble Fab ELISA. More than 72% clones from the second round, and 98% from the third round were found to bind specifically to mPDGFRβ, suggesting a high efficiency of the selection process. Ligand blocking assays revealed that about 2.5% of binders also blocked mPDGFRβ from binding to its ligand PDGF-BB.

Figure 1B:
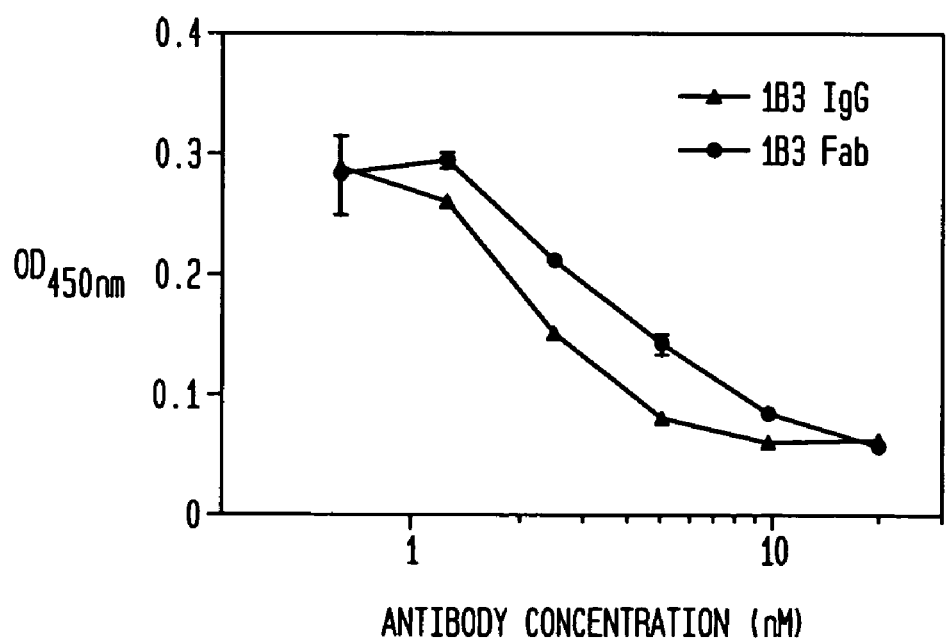

All seven Fab fragments bound specifically to mPDGFRβ and blocked mPDGFRβ from binding to its ligand, PDGF-BB, with varying potency. The IC50 values (i.e., the antibody concentration required to block 50% of PDGFRβ/PDGF-BB interaction) ranged from about 4 nM to >33 nM (FIG. 1B). The clone with the best receptor binding efficiency and receptor/ligand blocking potency, clone 1B3 (Table 1), was selected for further studies.

TABLE 1

SEQ ID NOS for Antibody Variable Domains and CDRs (nucleotide/amino acid)

| Antibody Name | VH | CDRH1 | CDRH2 | CDRH3 | VL | CDRL1 | CDRL2 | CDRL3 |
|---|---|---|---|---|---|---|---|---|
| 1B3 | 1/2 | 3/4 | 5/6 | 7/8 | 9/10 | 11/12 | 13/14 | 15/16 |
| 2C5 | 17/18 | 19/20 | 21/22 | 23/24 | 25/26 | 27/28 | 29/30 | 32/32 |

Full-length IgG antibody cloning and expression. The DNA sequences encoding the heavy and light chain genes for the leading clone, 1B3, were amplified by PCR and cloned into an expression vector containing human κ light-chain constant region and human γ1 heavy-chain constant region. The expression vector was transfected into NS0 myeloma cells and stable clones of 1B3-expressing cells were selected. The cells were grown in serum-free media and the full-length 1B3 IgG was purified from the cell culture supernatant by protein A affinity chromatography (Poros A, Applied Biosystems, Foster City, Calif.).

As expected, 1B3 IgG showed a much better binding efficiency to immobilized mPDGFRβ than its Fab fragment. The $IC_{50}$ values were 0.34 nM for 1B3 IgG and 1.3 nM for 1B3 Fab (FIG. 1A). Binding kinetic analysis by surface plasmon resonance on a BIAcore instrument revealed that the affinity of 1B3 for binding to mPDGFRβ was increased approximately 57 times over its Fab form (5.1 nM for Fab and 0.09 nM for IgG). No cross-reactivity was observed when 1B3 antibody was tested for binding to human PDGFRβ, either as soluble recombinant protein or cell-surface-expressed receptor on human tumor cell lines. Further, 1B3 did not bind to both human and mouse PDGFRα (data not shown). In a blocking assay, 1B3 inhibited mPDGFRβ from binding to its ligand PDGF-BB with an IC50 of 1.2 nM, whereas its Fab has an IC50 of 4.1 nM (FIG. 1B).

Figure 2A:
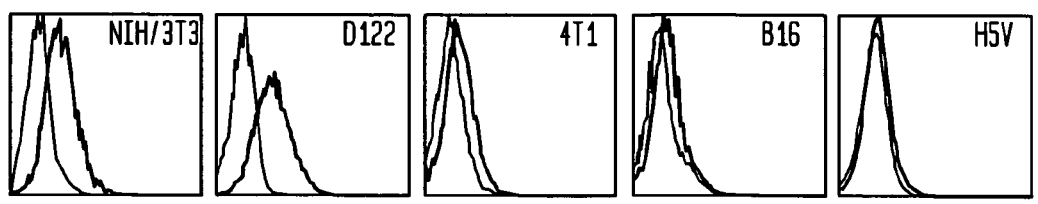
FIG. 2 depicts inhibition of PDGF-BB-induced receptor phosphorylation and downstream signaling molecules, MAPK and Akt resulting from binding of antibody 1B3 to cell surface PDGFRβ. (A) FACS analysis of NIH/3T3 (fibroblasts), D122 (Lewis lung carcinoma), 4T1 (Breast cancer), B16 (Melanoma) and H5V (PmT-transformed endothelial cells) cells, incubated with anti-PDGFRβ antibody 1B3 and anti-human Fc antibody-FITC conjugate. (B) Inhibition of PDGF-BB-induced receptor phosphorylation in NIH-3T3 cells. (C) Inhibition of PDGF-BB-induced receptor phosphorylation in D122 cells. (D) Inhibition of PDGF-BB-stimulate phosphorylation of AKT and p44/42 MAP kinase in D122 cells.

1B3 inhibits PDGF-BB-stimulated receptor phosphorylation and downstream signaling in a cell-based assay. Several mouse cell lines, including NIH/3T3 (fibroblasts), D122 (Lewis lung carcinoma), 4T1 (breast cancer), B16 (melanoma) and H5V (PmT-transformed endothelial cells), were tested for PDGFRβ expression by FACS analysis using 1B3 as the testing agent. The cells were aliquoted into wells of a 96-well plate at ~1×10⁶ per well, incubated with 1B3 (10 μg/ml) at 4° C. for 1 h, followed by incubation with an anti-human Fc antibody-FITC conjugate (Jackson ImmunoResearch) for an additional hour at 4° C. After several washes with cold PBS, the cells were analyzed using a FACSyantage SE flow cytometer (BD Biosciences, San Jose, Calif.). Anti-mPDGFRβ antibody from R&D was used as a positive control (data not shown). The FACS results (FIG. 2A) showed that NIH/3T3 and D122 express PDGFRβ at moderate level, 4T1 and B16 express the receptor at low level, and H5V did not yield any staining.

Receptor phosphorylation was determined for NIH/3T3 and D122 cells. The cells were plated onto 6 cm dishes and grown to 70-80% confluence, after which the cells were washed twice in PBS and cultured overnight in serum free medium. The cells were first incubated with various antibodies at RT for 30 min, followed by stimulation with PDGF-BB at 37° C. for 15 min. The cells were lysed in lysis buffer (50 mM Tris-HCl, pH 7.4, 150 mM NaCl, 1% TritonX-100, 1 mM EDTA, 1 mM phenylmethylsulfonyl fluoride, 0.5 mM $Na_3VO_4$ 1 µg/ml leupeptin, 1 µg/ml pepstatin, and 1 µg/ml aprotinin) for 1 h, followed by centrifugation of the lysate at 12,000 rpm for 10 min at 4° C. The receptors were immunoprecipitated from the cell lysate supernatant by an anti-mPDGFRβ antibody (R&D Systems Inc), followed by the addition of 20 µl of ProA/G-sepharose beads. The precipitated receptor proteins were resolved on a 4-12% NuPAGE Bis-Tris gel and transferred to a polyvinylidene difluoride membrane. Phospho-mPDGFRβ protein was detected on the blot using an anti-phospho-tyrosine antibody-HRP conjugate (Santa Cruz Biotech, Santa Cruz, Calif.). Total receptor proteins loaded on the gel were assayed with an antibody to mPDGFRβ.

To study the downstream signaling, the cell lysate from the above treatment were resolved by a 4-12% NuPAGE Bis-Tris gel. Phosphorylated Akt and p44/42 mitogen-activated protein kinase (MAPK) were detected using an anti-phospho-Akt and an anti-phospho-p44/p42 MAPK and p44/p42 MAPK, respectively (eBioscience, San Diego, Calif.).

Figure 2B:
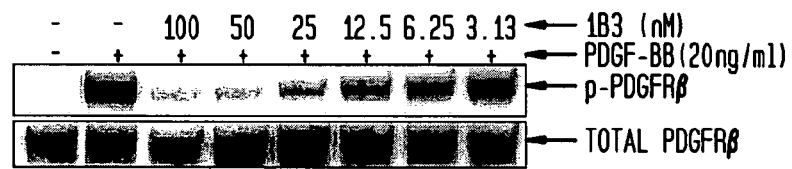
Figure 2C:
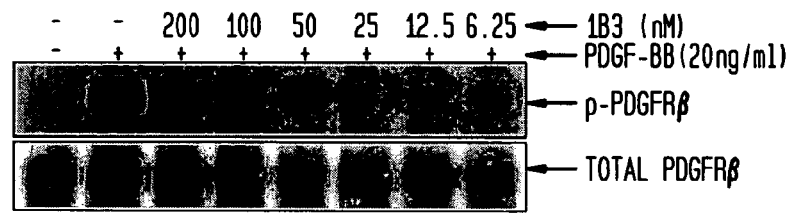
Figure 2D:
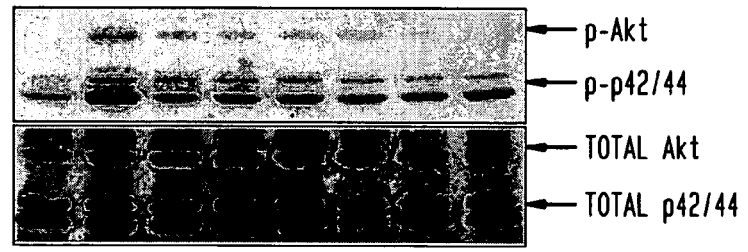

1B3 inhibited PDGF-BB-stimulated receptor phosphorylation in both NIH/3T3 and D122 cells in a dose dependent manner (FIGS. 2B and 2C). The antibodies also potently inhibited PDGF-BB-stimulated phosphorylation of both Akt and p44/42 MAP kinase in D122 cells (FIG. 2D).

Antitumor activity of anti-mPDGFRβ antibody in tumor xenograft models. Six human xenograft tumor models, including three ovarian carcinoma (SK-OV-3, OV-CAR-5 and OV-CAR-8), one pancreatic carcinoma (BxPC3), one lung carcinoma (NCI-H460), and one kidney carcinoma (Caki-1), were used to assess the antitumor activity of 1B3 in vivo. Athymic (nu/nu) mice (female, 7-8 weeks of age) were housed for 7-10 days before xenograft implantation. Each mouse was injected subcutaneously with $3-10\times10^6$ cells of SK-OV-3, OVCAR-5, OVCAR-8, Caki-1, BxPC3 or NCI-H460 tumor cells. When tumors reached approximately 250-300 $mm^3$, mice were randomized into groups of 10 to 12 animals each and treated by intraperitoneal injection, 2 to 3 times per week, with 1B3, DC101, or 1B3 in combination with DC101. Human IgG and/or USP saline were used as control groups. Tumor sizes and mouse body weight were measured twice a week. Tumor volume was calculated using the formula: $\pi/6\times(\text{length}\times\text{width}^2)$, where length=longest diameter and width=diameter perpendicular to length. The ratio of average tumor volume in the treatment group versus that in the control group (T/C %) was calculated. Statistic analysis was performed by Student's t-test.

Figure 3A:
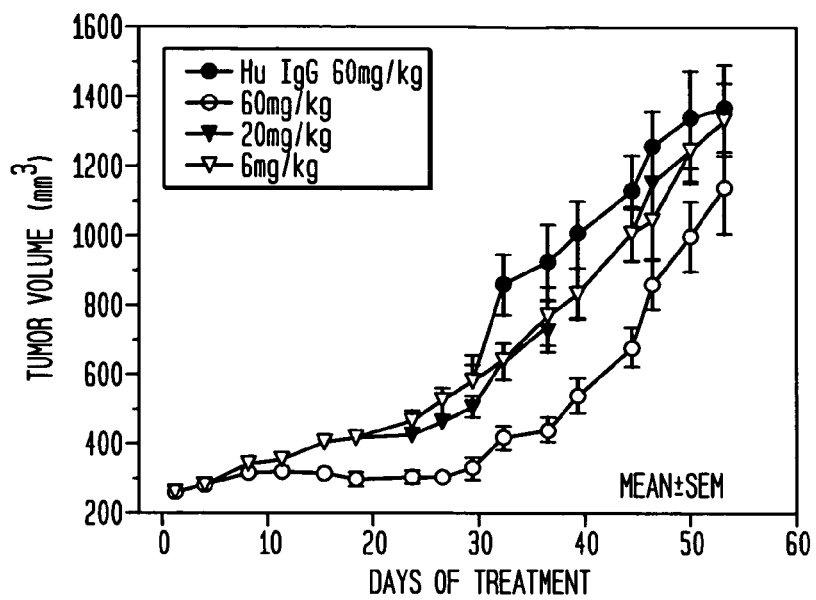
FIG. 3 shows the effect of treatment with anti-mPDGFRβ antibody, 1B3, on the growth of human xenograft tumors in vivo. Six xenograft models, SK-OV-3, OV-CAR-8, BxPC-3, OV-CAR-5, Caki-1 and NCI-H460 (A to F, respectively) were used to examine the effects of 1B3 on xenograft tumors in athymic nude mice. Mice with established tumors (~250-300 mm$^3$) were randomly grouped and treated with 1B3, normal human IgG, or saline by intraperitoneal injection twice weekly (except for BxPC-3 model where the mice were treated three times a week) at the dose indicated. Tumor volumes were measured twice a week and are presented as mean±SEM. *1 indicates the loss of one mouse due to severe illness. 1B3 binds to mouse, but not human, PDGFRβ. Accordingly, the observed responses to treatment result from inhibition of stimulation of host cells.
Figure 3B:
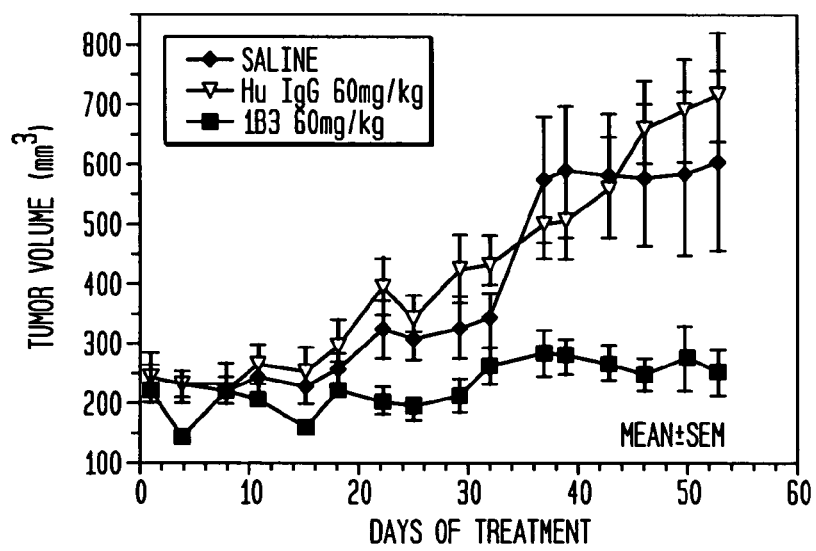
Figure 3C:
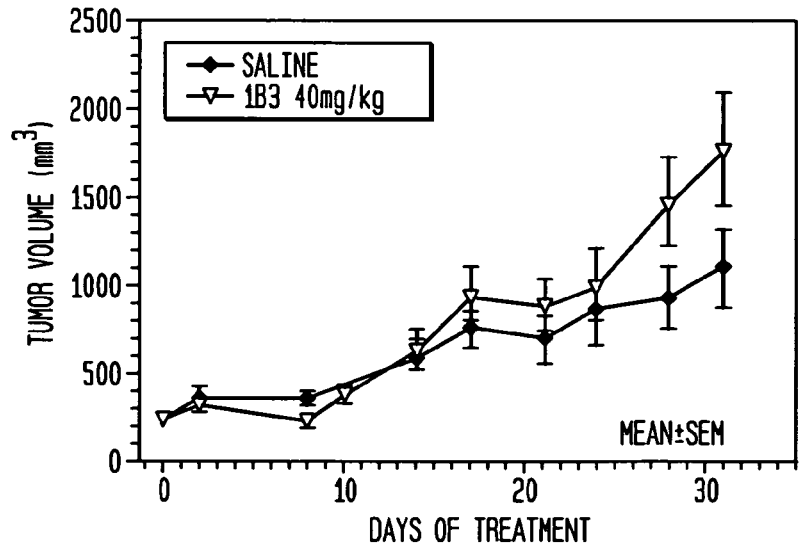
Figure 3D:
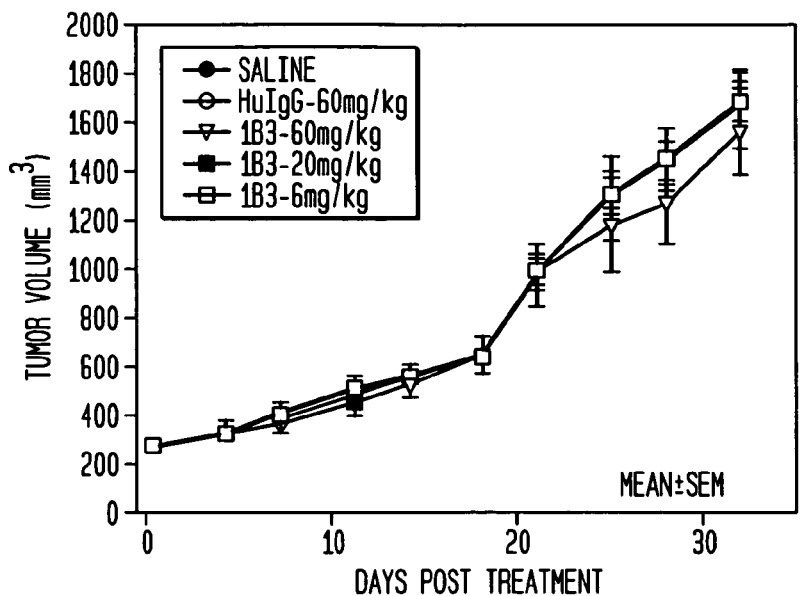
Figure 3E:
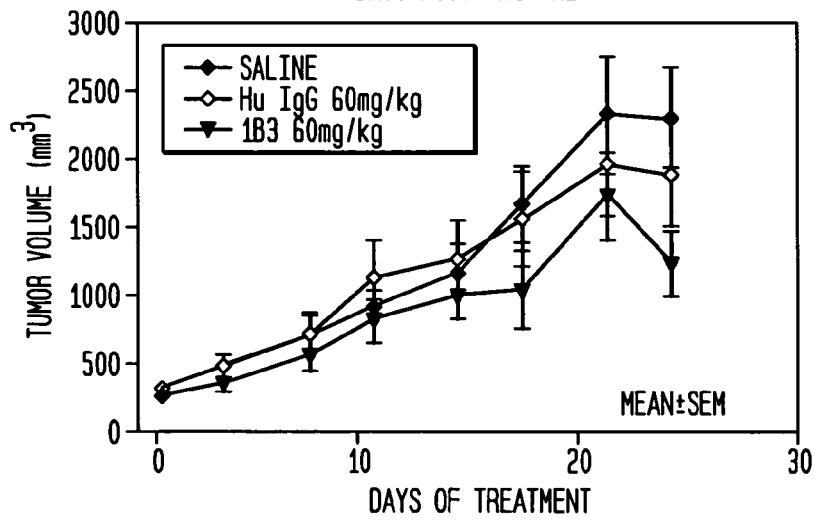
Figure 3F:
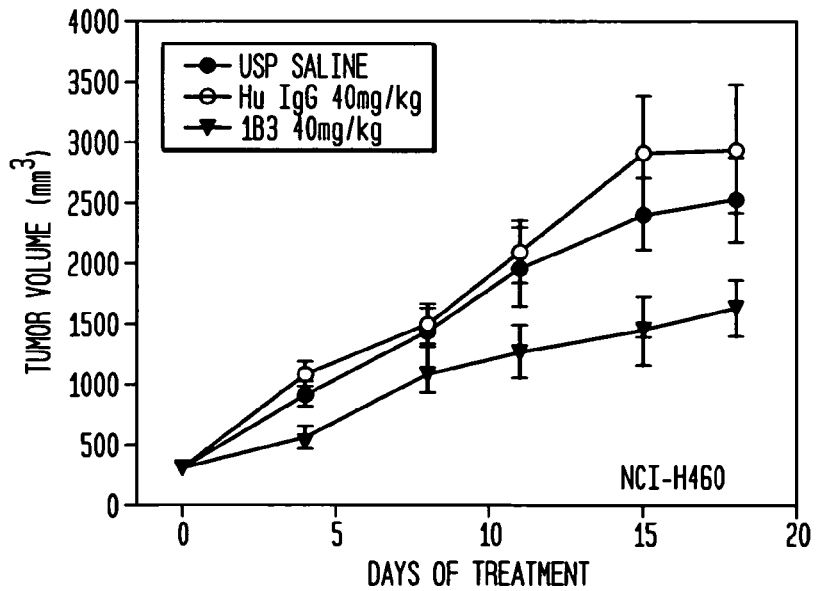

To study the antitumor effects of monotherapy with an anti-PDGFRβ antibody, mice were treated with 1B3, normal human IgG, or saline twice weekly by intraperitoneal injections. In SK-OV-3 model, tumor-bearing mice were given 1B3 at 6, 20, or 60 mg/kg dose. No tumor growth inhibition was observed in mice treated with the two lower doses of 1B3 (FIG. 3A). At 60 mg/kg, 1B3 completely blocked the tumor growth for up to 29 days post the initiation of the treatment (P=0.0028), after which the tumors started to grow rapidly at a rate similar to that in the human IgG-treated control group, despite the continuous antibody treatment (FIG. 3A). 1B3 (at 60 mg/kg dose) also demonstrated significant antitumor activity in both OV-CAR-8 and NCI-H460 xenograft models: it almost completely blocked the growth of OV-CAR-8 tumors during the course of treatment (FIG. 3B) (P=0.0022), and significantly slowed the growth of NCI-H460 tumors (FIG. 3F) (P<0.05). On the other hand, 1B3 (at 40 mg/kg three times per week or 60 mg/kg twice weekly) failed to show any antitumor activity in BxPC3, OV-CAR-5 and Caki-1 xenograft models (FIGS. 3C, 3D and 3E). 1B3 treatment did not cause any overt toxicity, including changes in body weight and animal behavior, in all six models examined.

Figure 4A:
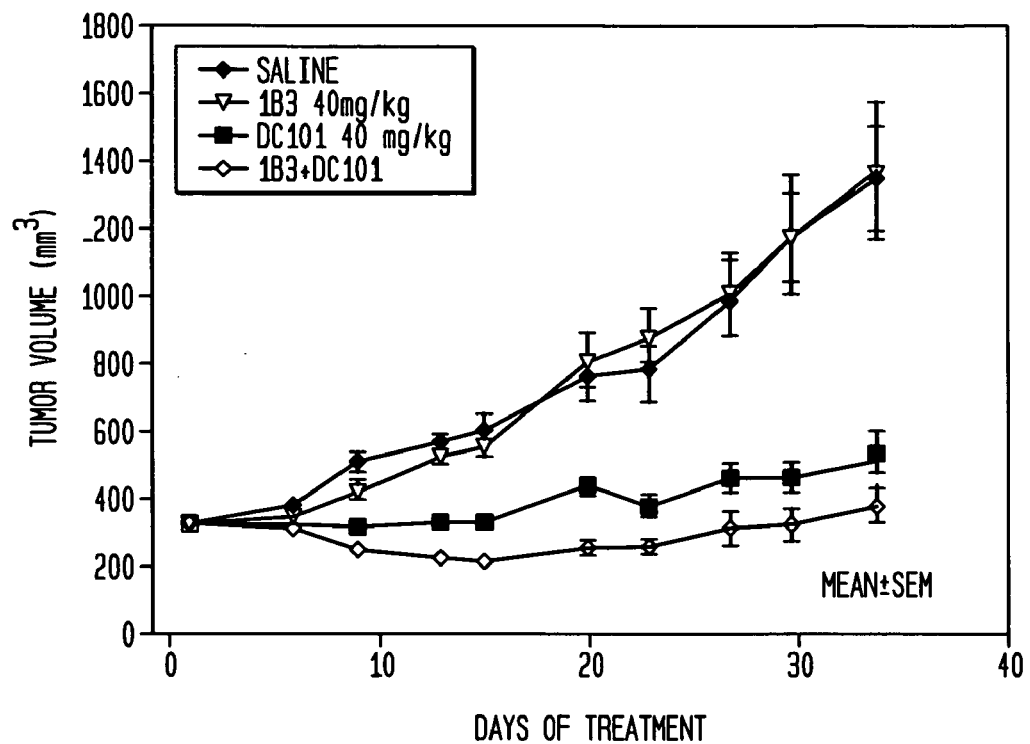
FIG. 4 shows the effect of combined treatment with anti-mPDGFRβ antibody, 1B3, and anti-mVEGFR2 antibody, DC101, on the growth of human xenograft tumors in vivo. Subcutaneous xenografts of BxPC-3 (A) or 5×10$^6$ NCI-H460 (B) were established in female athymic (nu/nu) mice. When tumors reached ~300-350 mm$^3$, mice were randomized and divided into four groups (n=12), and treated with USP saline, 40 mg/kg of 1B3, 40 mg/kg of DC101 or 40 mg/kg 1B3 plus 40 mg/kg DC101, three times a week. Tumor volumes were measured twice a week and are presented as mean±SEM. *1 indicates the loss of one mouse due to severe illness. 1B3 binds to mouse, but not human, PDGFRβ. DC101 binds to mouse, but not human, VEGFR2. Accordingly, the observed responses to treatment result from inhibition of stimulation of host cells.
Figure 4B:
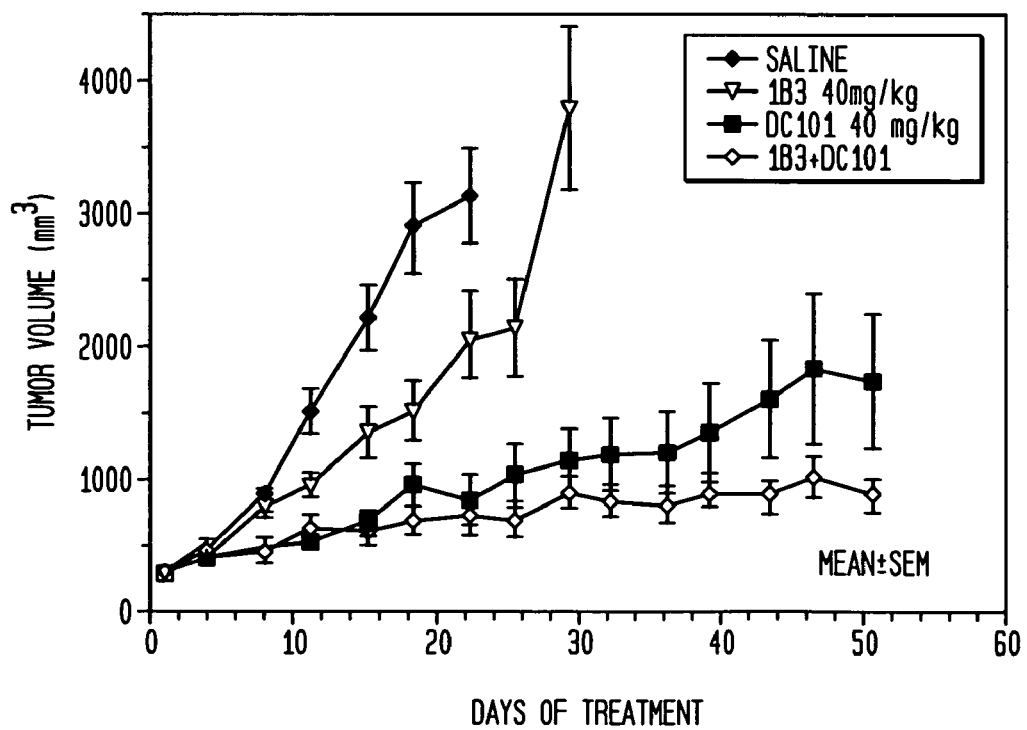

Enhancement of antitumor and anti-angiogenic activity of an anti-VEGFR2 antibody, DC101, by 1B3 in tumor xenograft models. The antitumor and anti-angiogenic activities of anti-VEGFR2 antibodies have been demonstrated in multiple animal models (Prewett, M. et al., 1999, Cancer Res. 59:5209-18). Here we demonstrate that 1B3 is capable of enhancing the antitumor and anti-angiogenic activities of DC101 using two xenograft models, BxPC-3 (pancreatic carcinoma) and NCI-H460 (non-small cell lung carcinoma). Athymic nude mice bearing xenografted tumors of 300-350 $mm^3$ size were randomized and divided into four treatment groups (n=12/group), and were treated by intraperitoneal injections three times a week with saline, 1B3 (40 mg/kg), DC101 (40 mg/kg), or 1B3 (40 mg/kg) plus DC101 (40 mg/kg). As expected, treatment with DC101 significantly inhibited the growth of both BxPC3 and NCI-H460 xenografts (P=0.0001 and <0.0001, respectively) (FIGS. 4A and 4B). Monotherapy with 1B3 demonstrated modest antitumor activity in the NCI-H460 model (T/C %=66% on day 22 post treatment, P=0.0062), but failed to show any antitumor activity in BxPC3 xenografts. Combination of 1B3 and DC101 led to significantly enhanced tumor inhibition in BxPC3 model: T/C % at the end of therapy was 27.3% in mice that received antibody combination, compared to that of 38.7% in mice treated with DC101 alone (P=0.0346). Further, tumor regression was observed in 7 out 12 mice (58.3%) in the antibody combination group, compared to that in 2 out 11 mice (18.2%) in the DC101 alone group, and no regressions in mice received 1B3 alone. In the NCI-H460 model, 1B3 plus DC101 also yielded much more potent tumor inhibitory activity than either 1B3 or DC101 alone: on day 22 post treatment, T/C % was 22% in the 1B3 plus DC101 group, compared to that of 66% in the 1B3 group (P<0.0001); at the end of the study (day 50 post treatment), the mean tumor volume in the antibody combination group was twice as small as that in the DC101 alone group (813.9±127.8 $mm^3$ versus 1660.9±554.4 $mm^3$) (P=0.025). While there were no deaths in the antibody combination group, two out of 12 mice in the DC101 group dead during the experiment (one on day 22 and the other on day 43).

Immunohistochemistry of Tumor Sections. Tumor xenografts from antibody-treated mice were examined by immunohistochemistry staining for both vessel density and pericyte coverage on the vessels. On Day 34 (BxPC3 model) or day 50 (NCI-H460 model) post treatment, six mice each from DC101 monotherapy and DC101/1B3 combination therapy groups were euthanized. Tumors were removed, fixed in 10% neutral buffered formalin at 4° C. for over night, and paraffin embedded. Fixed tumors were sectioned to 6 µm in thickness with Leica RM2135 microtome, following by double staining for both blood vessels and pericyte/SMC coverage.

Tumor sections were stained with both an anti-CD31 antibody (for blood vessel staining) and an anti-α-smooth muscle actin (α-SMA) antibody (for pericyte staining). Sections were first incubated with a rat anti-mouse PECAM-1 (anti-CD31 antibody, Pharmingen, San Diego, Calif.) at 4° C. for over night, followed by incubation with a biotin-SP-labeled donkey anti-rat IgG antibody, then a streptavidin-Cy3 conjugate (both from Jackson ImmunoResearch). The sections were further stained with an anti α-SMA antibody-FITC conjugate (Sigma). Finally, the sections were counterstained with ToPro (Molecular Probe, Leiden, Netherlands) at RT for 5 minutes.

Immunofluorescence images (at 200× magnification) were acquired using EZ-C1 2.20 software through a digital camera connected to a confocal microscope (Nikon Eclipse TE2000U). Computer assisted morphologic quantification was performed using Image Pro Plus software (MediaCybernatics, Silver Spring, Md.) and analyzed from each section.

Five digital images of tumor periphery and tumor core from each section were counted for total $CD31^+$ vessels, α-$SMA^+$ vessels, mature vessels (dual $CD31^+$ and α-$SMA^+$), and the percentage of dual $CD31^+$/α-$SMA^+$ vessels over total $CD31^+$ vessels. Two different quantitation methods were used to measure the degree of vascularity of individual tumor sections: vessel density (numbers of vessels/$mm^3$) and percentage of vessel area (% vessel area over total tumor area). Computer assisted morphologic quantification was performed using Image Pro Plus software. For statistical analysis, two-way ANOVA followed by Fisher's LSD method was used for multiple comparisons (Sigma Stat 3.1 Systat Software, Inc., Point Richmond, Calif.).

Figure 5A:
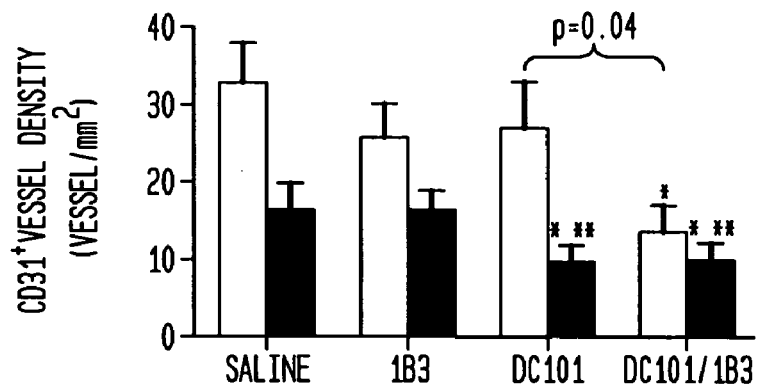
FIG. 5 represents results of immunohistochemical analysis of human xenografts after treatment with 1B3, DC101, or DC101 plus 1B3. On Day 34 (BxPC3 model, panel A to C) or 50 (NCI-H460 model, panel D to F) post treatment, six mice from each group were sacrificed and tumors were processed for IHC analysis. Tumors were sectioned and double staining for both blood vessels (anti-CD31) and pericyte/SMC coverage (α-SMA, panel B and E). Five digital immunofluorescence images of tumor periphery and tumor core from each section were acquired and quantified for total CD31$^+$ vessels (panel A and D), α-SMA$^+$ vessels (panel B and E), and the percentage of dual CD31$^+$/α-SMA$^+$ over total CD31$^+$ vessels (panel C and F). Two different quantitation methods were used to measure the degree of vascularity of individual tumor sections: vessel density (numbers of vessels/mm$^3$) and percentage of vessel area (% vessel area over total tumor area). For statistic analysis, two-way ANOVA followed by Fisher's LSD method was used for multiple comparisons (Sigma Stat 3.1 Systat Software, Inc., Point Richmond, Calif.). *P<0.05 compared to the saline group. Open bars, tumor periphery; solid bars, tumor core.
Figure 5B:
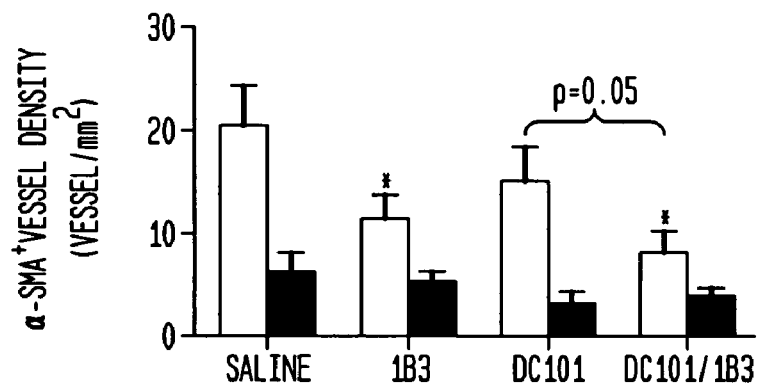
Figure 5C:
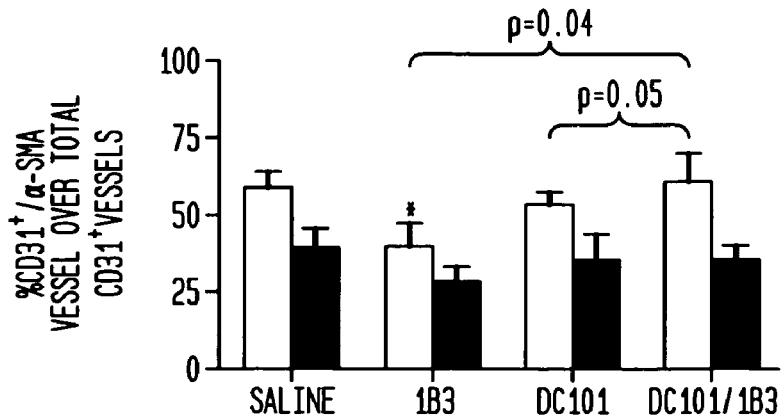
Figure 5D:
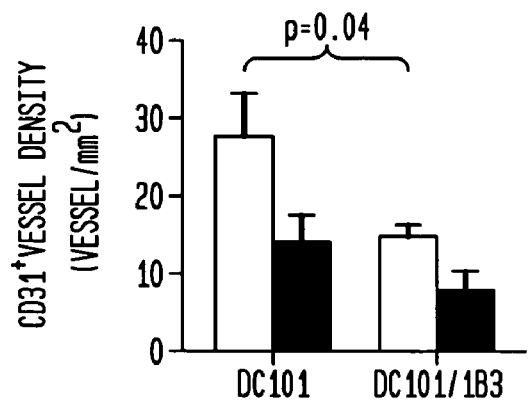
Figure 5E:
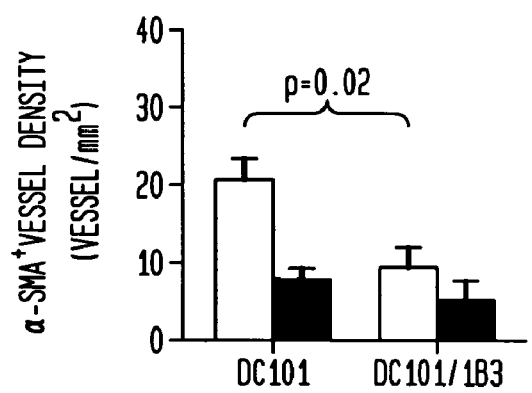
Figure 5F:
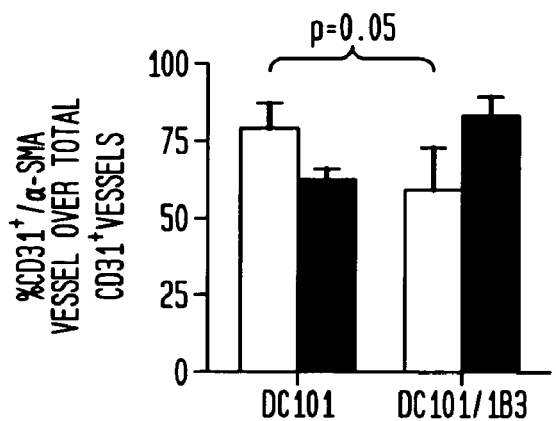

DC101 treatment significantly reduced the $CD31^+$ vessel density in BxPC3 tumor xenografts, mainly within the tumor core (FIG. 5A), but only showed weak effect on α-$SMA^+$ vessel density (FIG. 5B). The addition of 1B3 to DC101, while failing to further decrease the vascularity in the tumor core, led to significantly increased reduction of vessel density in the periphery of the tumors (FIG. 5A). 1B3 alone showed no significant effect on overall tumor vessel density (FIG. 5A), but reduced the α-SMA staining in tumor periphery (FIG. 5B), resulting in a reduced percentage of CD31/α-SMA double positive (mature) vessel (FIG. 5C). This indicates that PDGFRβ-positive pericytes in tumors were selectively inhibited. Interestingly, in both DC101 alone and DC101 plus 1B3 treated tumors, the degree of reduction of $CD31^+$ vessels correlates directly with the reduction of α-$SMA^+$ pericyte coverage in both tumor core and periphery (FIGS. 5A and B). As a consequence, the percentage of mature vessels in both tumor periphery and core, i.e., proportion of dual $CD31^+$/α-$SMA^+$ vessels over total $CD31^+$ vessels, did not appear to be significantly different between tumors from mice treated with saline, DC101 alone, or DC101 plus 1B3 (FIG. 5C). Similar phenomena were also observed in NCI-H460 tumor xenografts (FIG. 5D-F). Finally, almost identical observations in both tumor xenografts were obtained when the degree of tumor vascularity was determined using an alternative scoring method which measures the percentage of vessel area over total tumor area (not shown).

Selection of human anti-hPDGFRβ antibodies. The phage display library described above was screened for phage-Fab that bind to human PDGFRβ. As described above for 1B3, the DNA sequences encoding the heavy and light chain genes for the leading hPDGFRβ-binding clone, 2C5 (Table 1), were amplified by PCR and cloned into an expression vector containing human κ light-chain constant region and human γ1 heavy-chain constant region. The expression vector was transfected into NS0 myeloma cells and stable clones expressing 2C5 antibody were selected.

Figure 6:
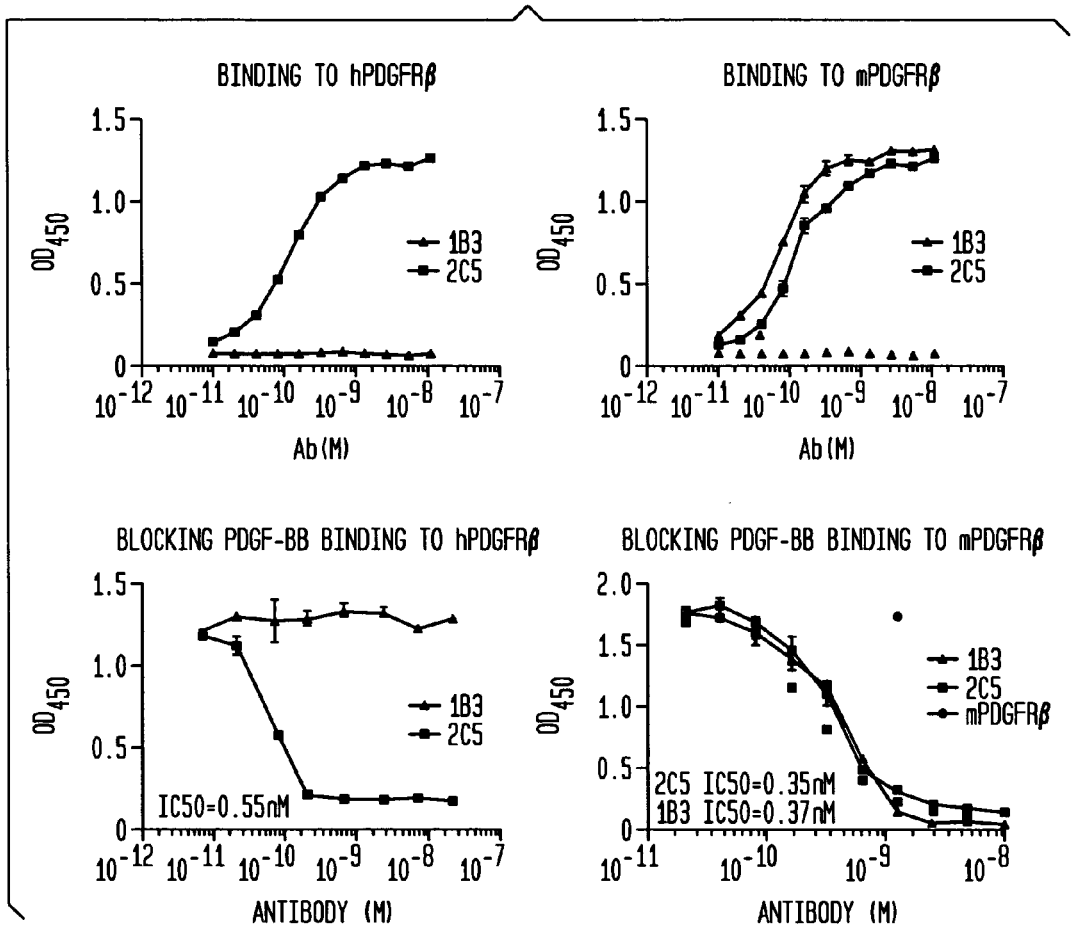
FIG. 6 depicts receptor binding and ligand (PDGF-BB) blocking by PDGFRβ-specific human antibody 2C5 to human PDGFRβ and murine PDGFRβ. Binding and ligand blocking are compared to PDGFRβ-specific antibody 1B3, which binds only to murine PDGFRβ.

As determined by BIAcore analysis, 2C5 binds to hPDGFRβ with similar binding characteristics as 1B3 binds to mPDGFRβ. Like 1B3, 2C5 is specific for PDGFRβ and does not bind to hPDGFRα. However, whereas 1B3 binds to murine PDGFRβ but not human PDGFRβ, 2C5 binds to both proteins. (FIG. 6). In one experiment, Kd values for 2C5, determined by surface plasmon resonance, were $1.36 \times 10^{-11}$ M for hPDGFRβ and $6.05 \times 10^{-11}$ M for mPDGFRβ. The Kd for 1B3 binding to hPDGFRβ was $4.17 \times 10^{-11}$ M.

2C5 also blocks binding of PDGF-BB to both human and mouse PDGFRβ, as shown in FIG. 6. The IC50 values were 0.55 nM for hPDGFRβ and 0.35 nM for mPDGFRβ.

Figure 7:
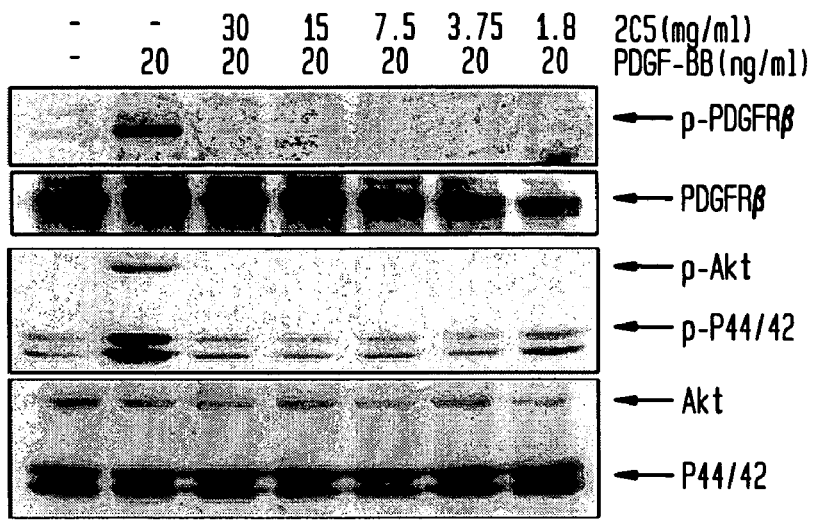
FIG. 7 is a Western blot demonstrating inhibition of ligand (PDGF-BB) induced phosphorylation of PDGFRβ in human Caki-1 tumor cells by anti-PDGFRβ antibody 2C5. The antibody also inhibits phosphorylation of Akt and P44/42.
Figure 8:
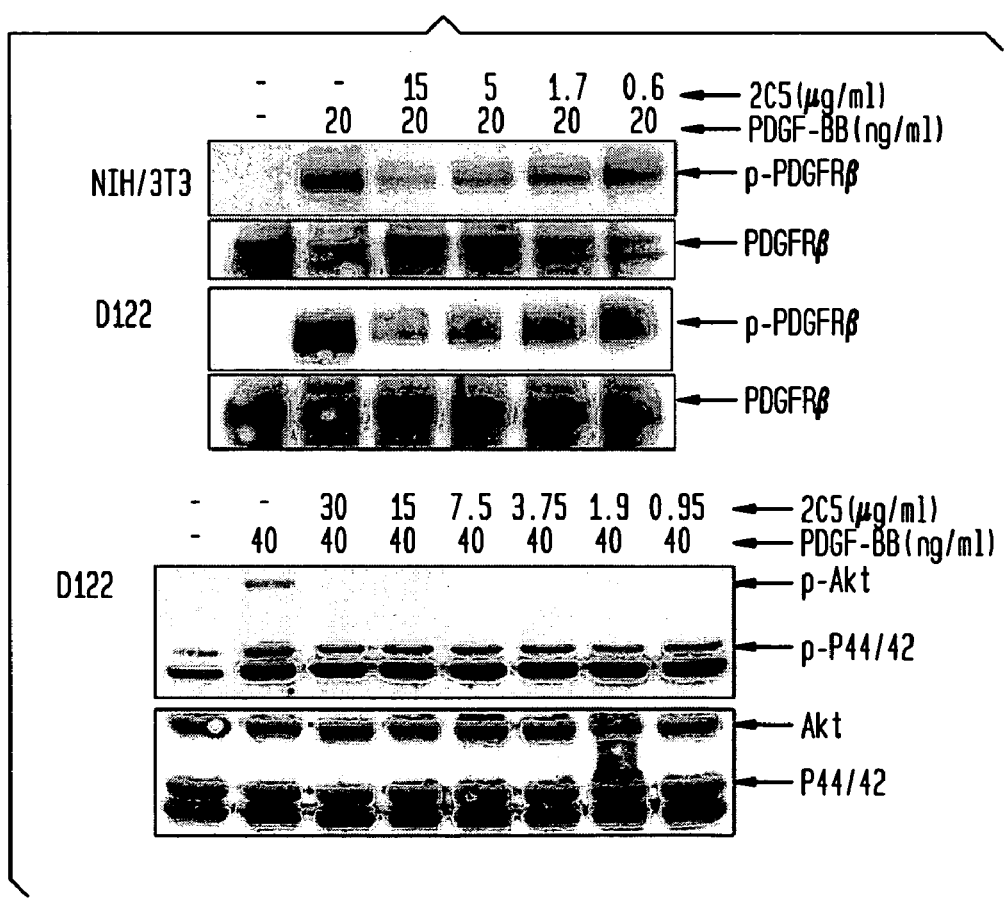
FIG. 8 shows Western blots demonstrating inhibition of ligand (PDGF-BB) induced phosphorylation of PDGFRβ in mouse NIH-3T3 and D122 cell lines by anti-PDGFRβ antibody 2C5.
Figure 9A:
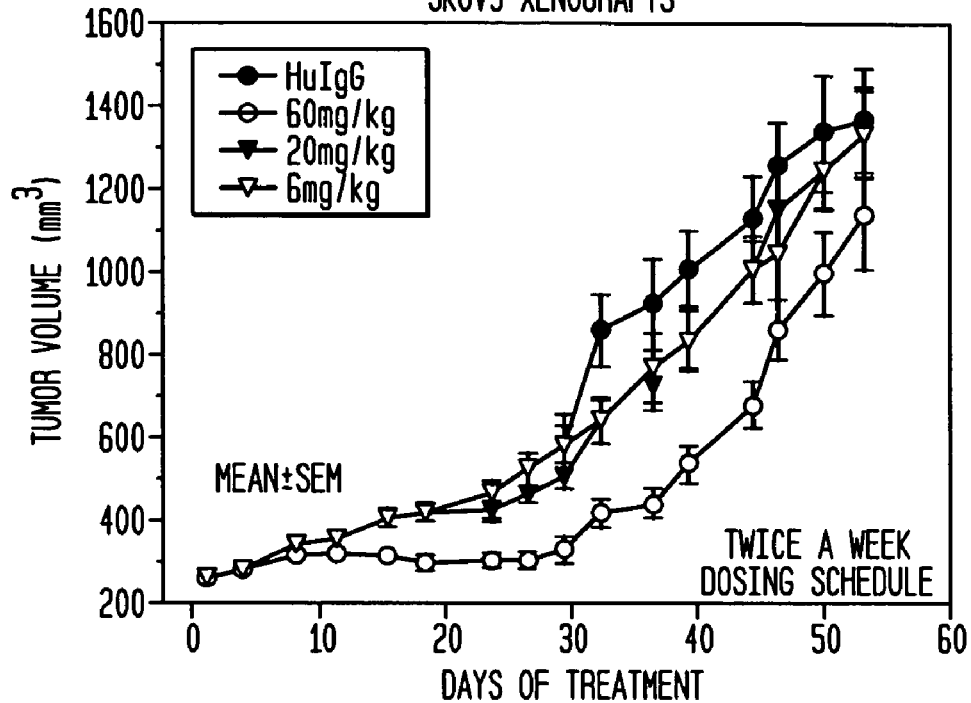
FIG. 9 depicts growth of six subcutaneous human xenograft tumors in nude mice treated with anti-PDGFRβ antibody 1B3 (specific for murine PDGFRβ) and/or 2C5 (which binds both to human and murine PDGFRβ).
Figure 9B:
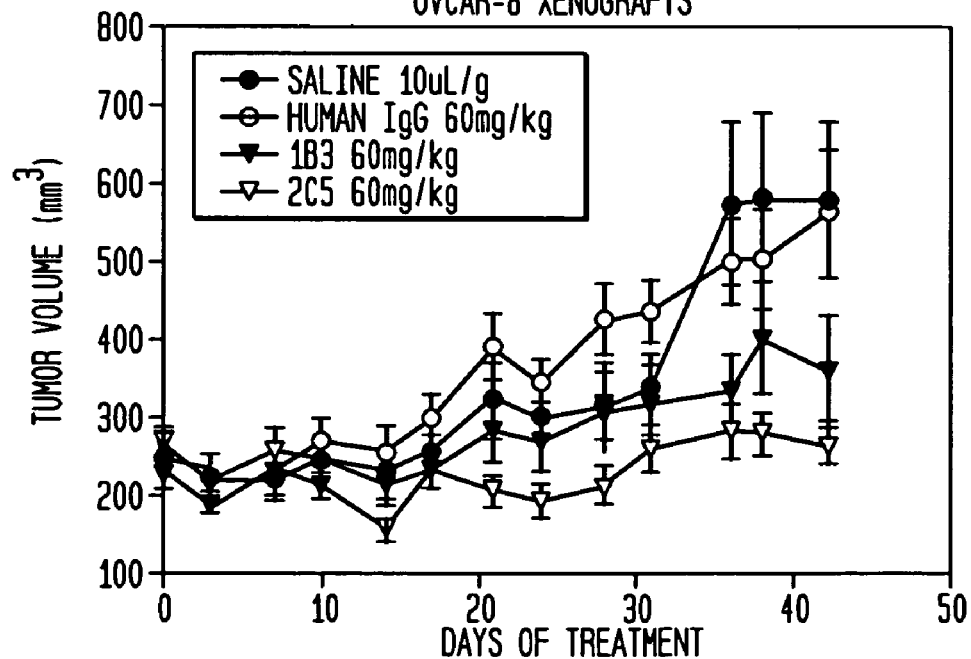
Figure 9C:
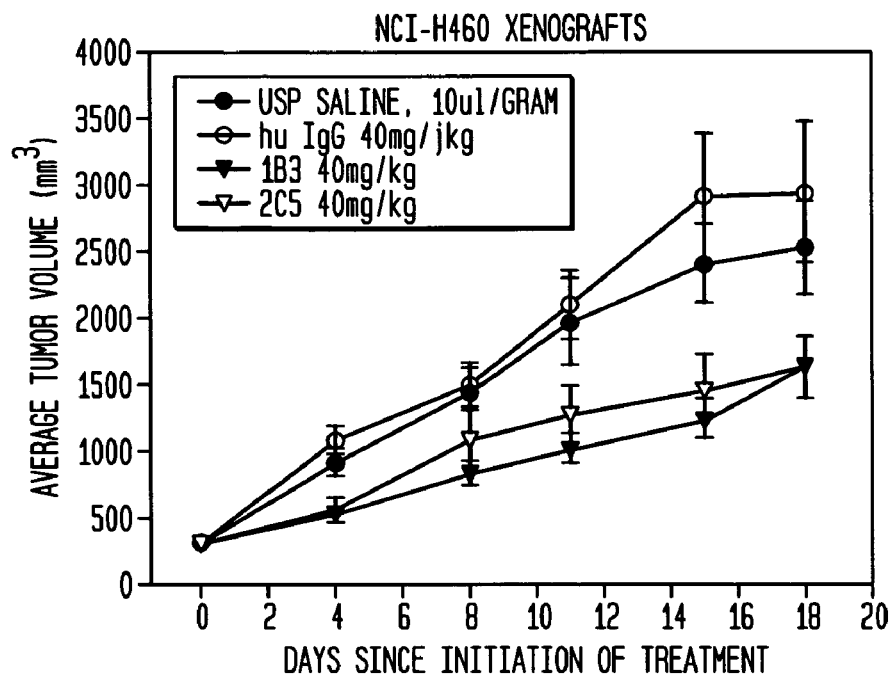
Figure 9D:
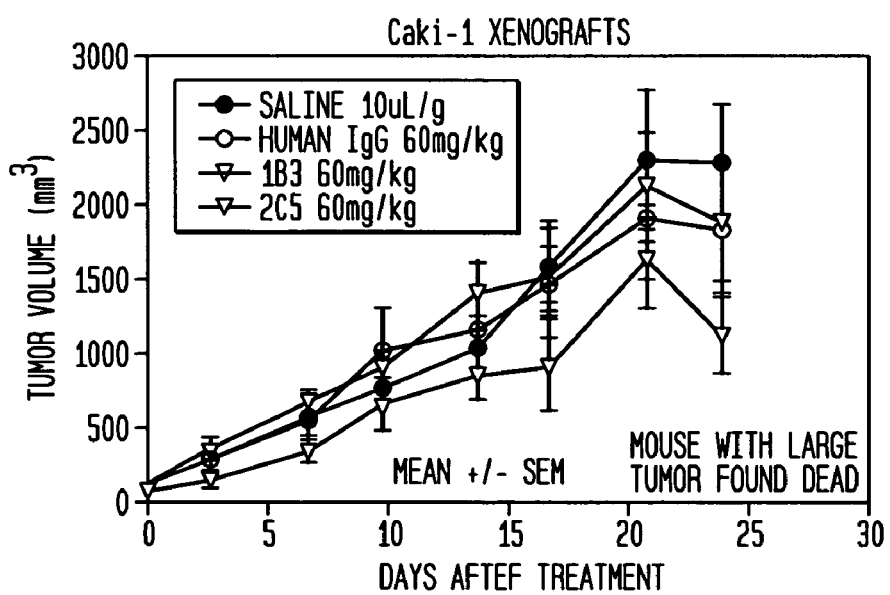
Figure 9E:
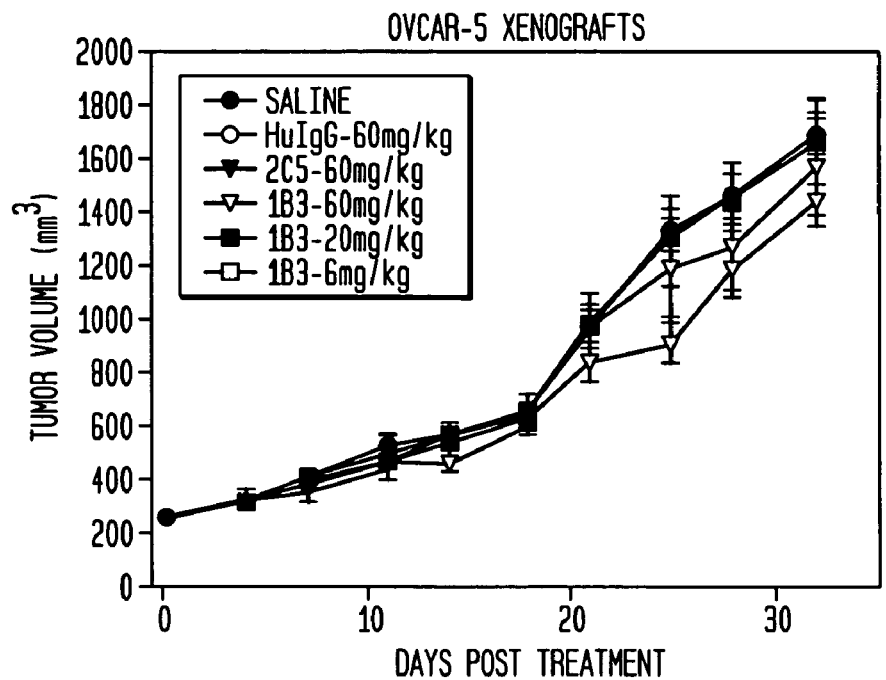
Figure 9F:
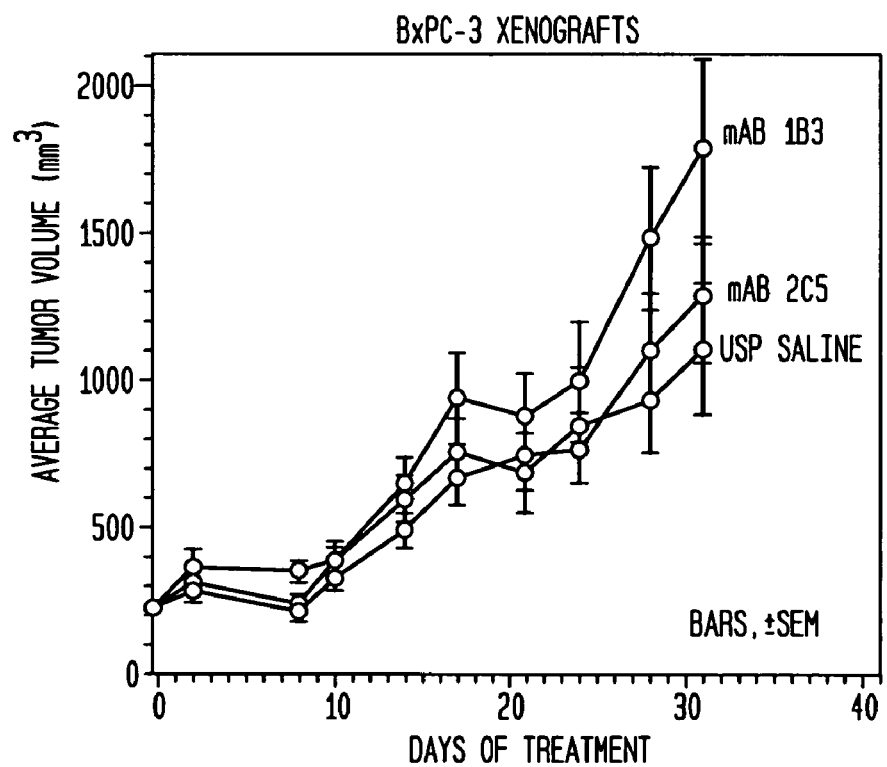

2C5 inhibits PDGF-BB-stimulated receptor phosphorylation and downstream signaling in a cell-based assay. The ability of 2C5 to block PDGFRβ phosphorylation was determined for human Caki-1 tumor cells (FIG. 7) and mouse NIH/3T3 and D122 cells lines (FIG. 8). 2C5 blocked receptor phosphorylation even at low concentrations that were tested (IC50 <<1.8 μg/ml). 2C5 also potently inhibited PDGF-BB-stimulated phosphorylation of both Akt and p44/42 MAP kinase in Caki-1 cells (FIG. 7) and D122 cells (FIG. 8).

Antitumor activity of anti-PDGFRβ antibody in tumor xenograft models. The five human xenograft tumor models described above (OVCAR-5 and OVCAR-8, BxPC3, NCI-H460, and Caki-1) were used to assess the antitumor activity of 2C5 in vivo. 2C5 which binds to and inhibits human PDGFRβ receptors of the tumor and mouse receptors of the vasculature was compared to 1B3 which bound only to mouse vasculature. Moderate reductions in tumor growth were observed in SKOV-3, OVCAR-8, and NCI-H460 models, but not in OVCAR-5, BxPC3 and Caki-1 models. (FIG. 9; Table 2).

TABLE 2

Anti-PDGFRβ Antibody Monotherapy

| Xenograft | Tumor Volume | | | | MFI (FACS) |
|---|---|---|---|---|---|
| | 1B3 | | 2C5 | | |
| | T/C % | P value | T/C % | P value | |
| SKOV-3 (Day 29) | 57 | 0.0028 | — | — | 2 |
| BxPC3 | 100 | >0.05 | 100 | >0.05 | 1 |
| OVCAR-5 | 92 | 0.7 | 84 | 0.06 | 1 |
| Caki-1 | 65 | 0.1004 | 91 | 0.6303 | 10 |
| | | | 49 | 0.0733 | |
| OVCAR-8 | 43 | 0.0022 | 39 | 0.0014 | 5 |
| NCI-H460 | 60 | 0.0235 | 60 | 0.0115 | 2 |

Figure 10A:
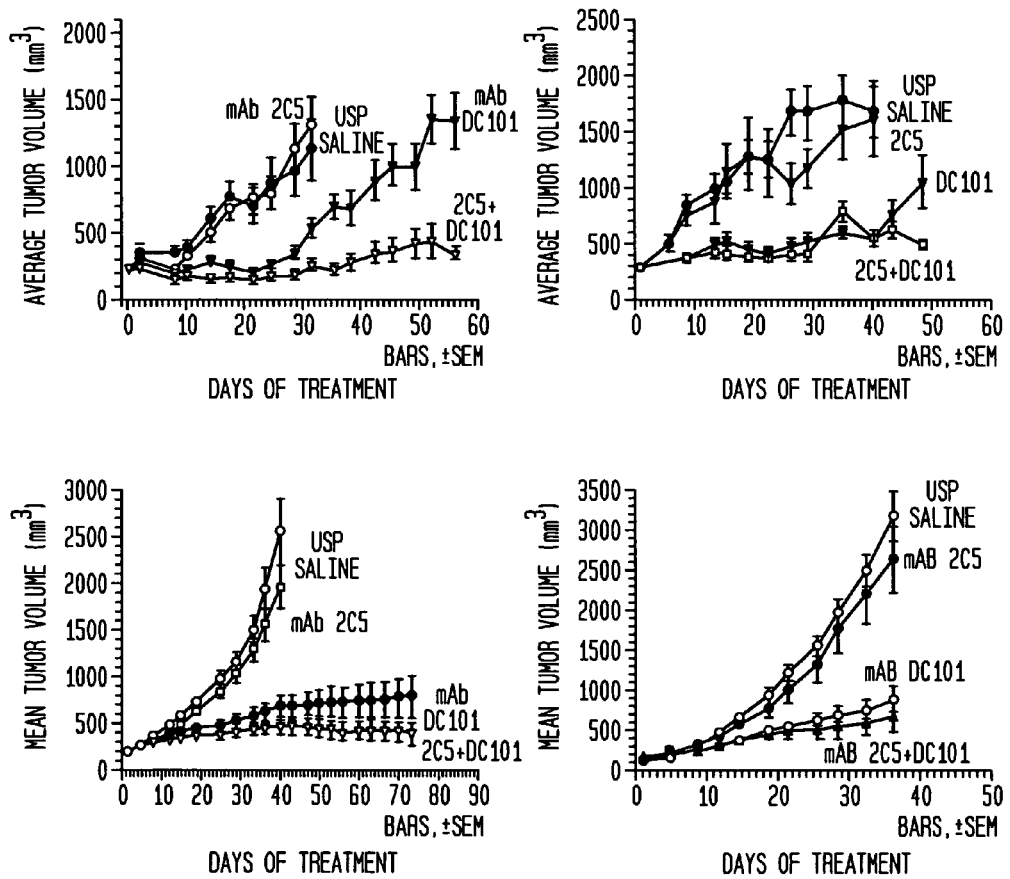
FIG. 10 depicts growth of six subcutaneous human xenograft tumors in nude mice treated with anti-PDGFRβ antibody 2C5 (which binds both to human and murine PDGFRβ) and a murine VEGFR-2 specific antibody (DC101).
Figure 10B:
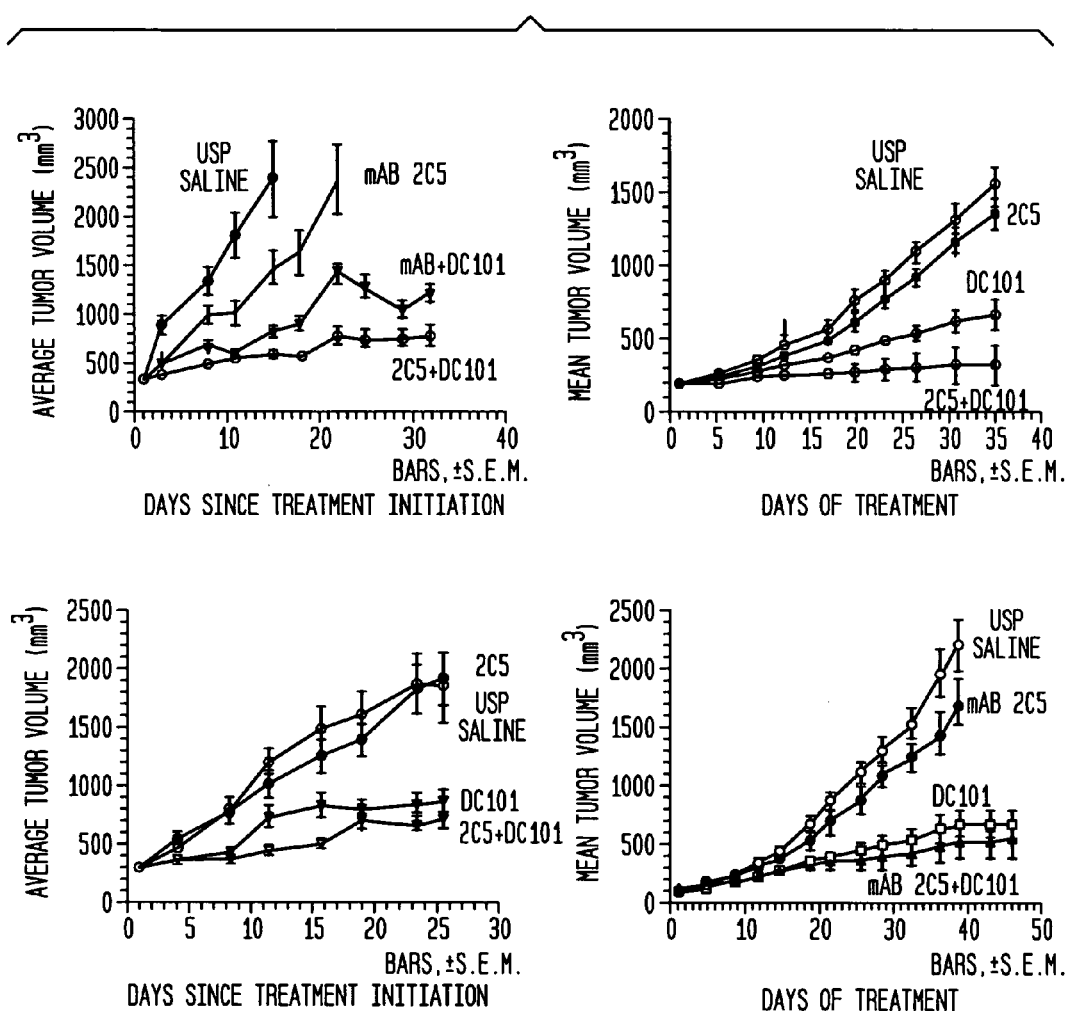

Antitumor activity of anti-PDGFRβ (2C5)/anti-mVEGFR 2 (DC101) antibody combination in tumor xenograft models. 2C5 which binds to human and mouse PDGFRβ receptors (i.e., PDGFRβ receptors on both tumor and vasculature of human xenografts in a murine host) was also tested for inhibition of tumor growth in combination with an antibody (DC101) specific for mouse VEGFR2. The xenograft cell lines were BxPC-3, MIA-PaCa-2, Detroit-562, HCT-8, NCI-H460, NCI-H292, and HCT-116. Coadministration of 2C5 and DC101 resulted in significantly greater inhibition of tumor growth than either of the antibodies alone. (FIG. 10 and Table 3).

TABLE 3

Anti-PDGFRβ Antibody in Combination with Anti-VEGFR2 Antibody

| Antibody | Xenograft | Tumor Model | Tumor Volume (Combo/DC101%) | P value |
|---|---|---|---|---|
| 1B3 + DC101 | BxPC-3 | Pancreatic | 65 | 0.0346 |
| | NCI-H460 | NSCLC | 48 | 0.1088 |

TABLE 3-continued

Anti-PDGFRβ Antibody in Combination with Anti-VEGFR2 Antibody

| Antibody | Xenograft | Tumor Model | Tumor Volume (Combo/DC101%) | P value |
|---|---|---|---|---|
| 2C5 + DC101 | Detriot562 | Squamous | 65 (Day 40) | 0.1146 |
| | | | 40 (Day 74) | |
| | BxPC-3 | Pancreatic | 31 | <0.0001 |
| | MIA-PaCa2 | Pancreatic | 49 | 0.1078 |
| | MIA-PaCa2 | Pancreatic | 75 | 0.4164 |
| | MIA-PaCa LP (orthotopic) | Pancreatic | 200 (weight) | 0.1975 |
| | HCT-8 | Colon | 48 (Day 30) | — |
| | | | 121 (Day 41) | 0.001 |
| | | | 36 (Day 49) | — |
| | HCT-116 | Colon | 80 | 0.001 |
| | NCI-H460 | NSCLC | 61 | <0.0001 |
| | NCI-H292 | NSCLC | 73 | 0.3832 |

Figure 11:
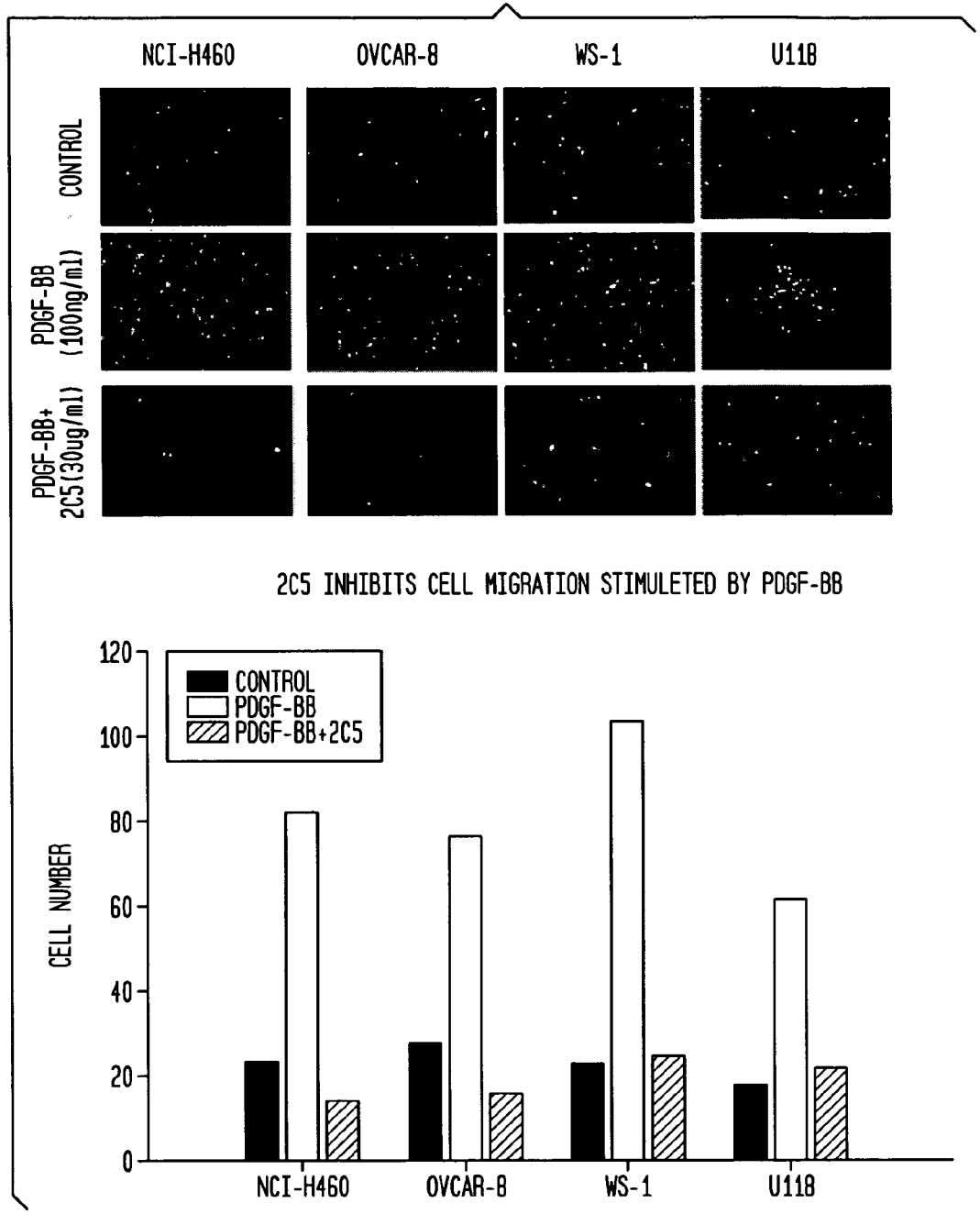
FIG. 11 shows the results of a cell-based migration assay, demonstrating that 2C5 inhibits PDGF-BB-stimulated cell migration.

2C5 inhibits PDGF-BB-stimulated cell migration in a cell-based migration assay. Two-chamber technique was used to determine the inhibitory ability of 2C5 in cell migration with NCI-H460, OVCAR8, WS-1 and U-118 cell lines. Collagen (100 μg/ml) was added to the up chamber (100 μl) and the lower chamber (150 μl) and incubated at 37° C. for 1 hour. After washing the chambers twice with PBS, 100 μl of starved cells (estimated 0.5-10×10$^6$/ml in serum-free medium) were added to the up chamber and 150 μl of serum-free medium was added to the lower chamber and then incubated at 37° C. for 4 hours. For PDGF-BB stimulation, PDGF-BB was added to the lower chamber to a final concentration of 100 ng/ml. In 2C5 wells, 2C5 were added into the up chamber at a final concentration of 30 μg/ml. Non-migrated cells in the up chamber were scraped from the membrane. After washing three times with PBS, migrated cells on the membrane of the lower chamber side were fixed with 4% formalin and stained with Hoechst (4 μg/ml). The results were captured and cells were counted under fluorescence microscopy. At a concentration of 30 μg/ml, 2C5 inhibited PDGF-BB-stimulated cell migration completely in all four cell lines used in the assay (FIG. 11).

Figure 12:
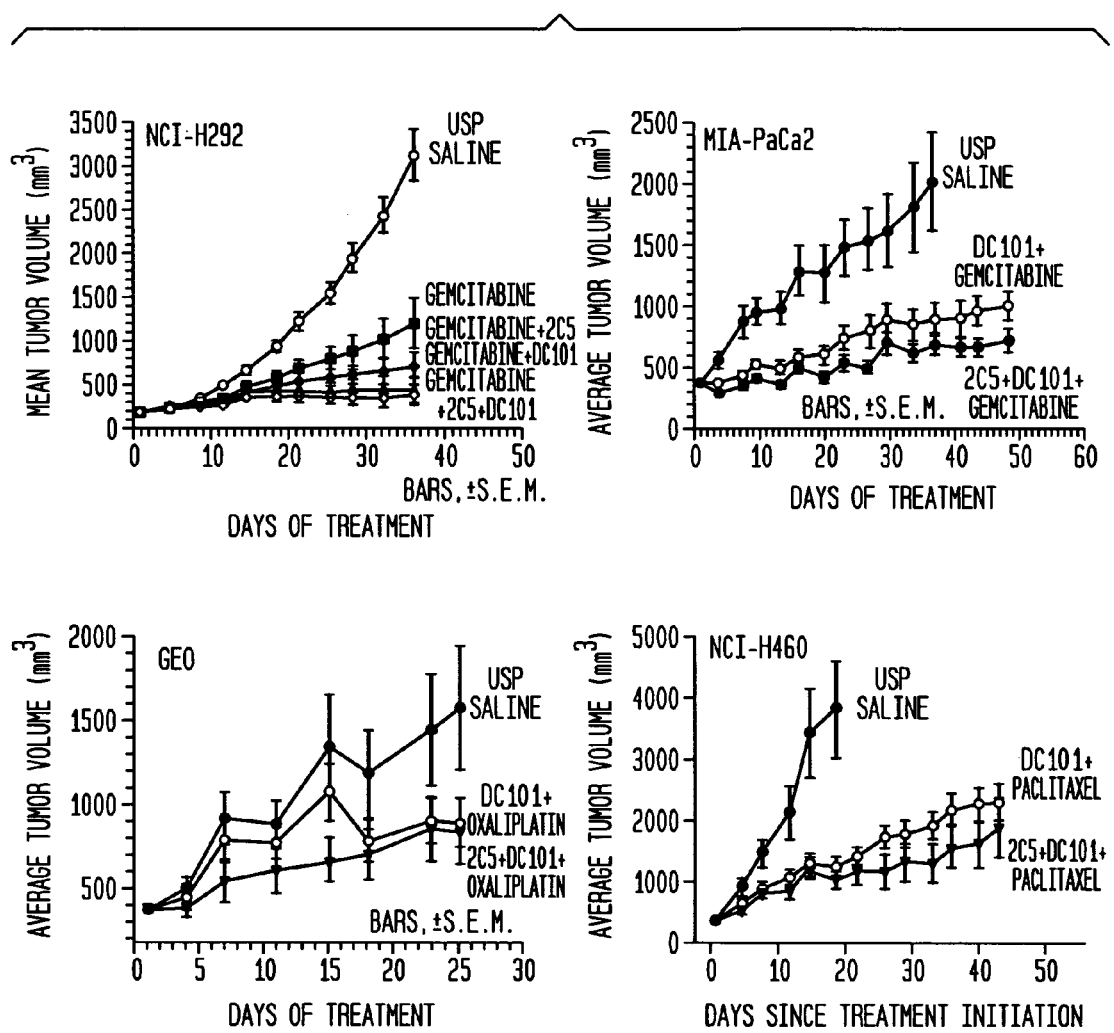
FIG. 12 shows the antitumor activity of 2C5/chemotherapy combination and 2C5/chemotherapy/DC101 therapy in tumor xenograft models.

Antitumor activity of anti-PDGFRβ (2C5)/chemo or anti-PDGFRβ (2C5)/chemo/anti-mVEGFR 2 (DC101) antibody combination in tumor xenograft models. Anti-PDGFRβ antibody 2C5 was also tested for inhibition of tumor growth in combination with chemotherapy (gemcitabine) or chemotherapy (gemcitabine, paclitaxel or oxaliplatin) plus an anti-VEGFR2 antibody (DC101). The xenograft cell lines were NCI-H292, MIA-PaCa-2, NCI-H460, and GEO. Coadministration of 2C5 and gemcitabine resulted in greater inhibition of tumor growth than either 2C5 or gemcitabine alone. Coadministration of 2C5, chemo and DC101 resulted in greater inhibition of tumor growth than the combination of chemo/DC101. (FIG. 12 and Table 4).

TABLE 4

Anti-PDGFRβ Antibody in Combination with Chemo and DC101/Chemo

| Combination (ref-ctl) | Xenograft | Tumor Model | Tumor Volume (Combo/ref-ctl %) | P value |
|---|---|---|---|---|
| Gemcitabine | NCI-H292 | NSCLC | 63 | 0.1753 |
| DC101 + Gemcitabine | NCI-H292 | NSCLC | 90 | 0.5976 |
| DC101 + Oxaliplatin | GEO | Colon | 90 | 0.1759 |
| DC101 + Paclitaxel | NCI-H460 | NSCLC | 78 | 0.2692 |
| DC101 + Gemcitabine | MIA-PaCa2 | Pancreatic | 52 | 0.2399 |

Figure 13:
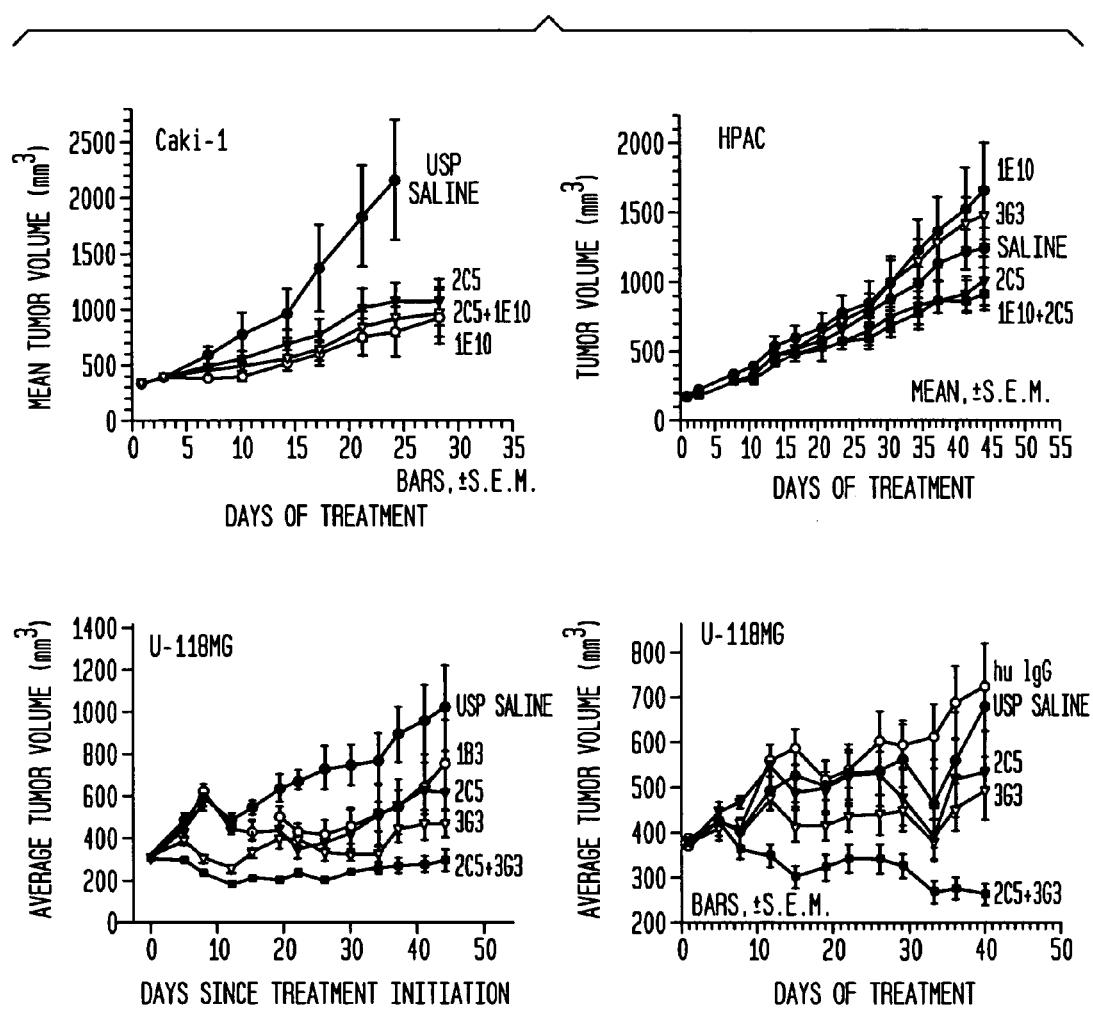
FIG. 13 shows the antitumor activity of 2C5/3G3 and 2C5/1E10 combination therapy in tumor xenograft models.

Antitumor activity of anti-PDGFRβ (2C5)/anti-PDGFRα (3G3 specific to hPDGFRα, or 1E10 specific to mPDGFRα) antibody combination in tumor xenograft models. Anti-PDGFRβ antibody 2C5 was also tested for inhibition of tumor growth in combination with an anti-PDGFRα antibody. The xenograft cell lines were Caki-1, HPAC and U-118MG. Coadministration of 2C5 and 3G3 resulted in significantly greater inhibition of tumor growth than either of the antibodies alone. (FIG. 13 and Table 5).

TABLE 5

Anti-PDGFRβ Antibody in Combination with Anti-PDGFRα Antibody

| Combination (ref-ctl) | Xenograft | Tumor Model | Tumor Volume (Combo/ref-ctl %) | P value |
|---|---|---|---|---|
| 1E10 (anti-mPDGFRα) | Caki-1 | Renal | 104 | 0.9037 |
| | HPAC | Pancreatic | 56 | 0.0052 |
| 3G3 (anti-hPDGFRα) | U-118MG | Glioblastoma | 45 | 0.0024 |
| | U-118MG | Glioblastoma | 61 | 0.1346 |

Figure 14A:
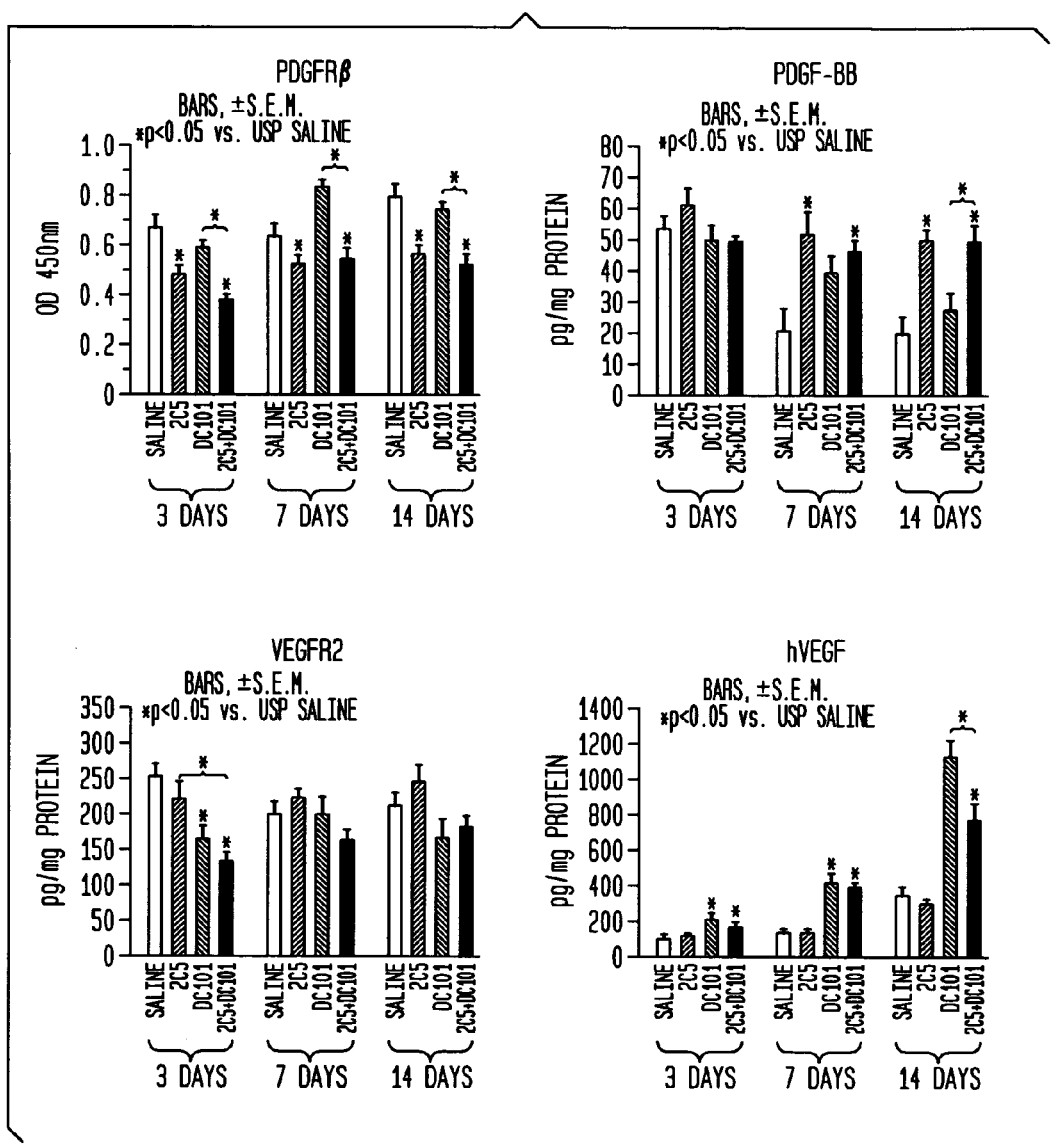
FIG. 14 shows the effects of 2C5 on PDGFRβ, PDGF-BB, VEGF and FGF expression.
Figure 14B:
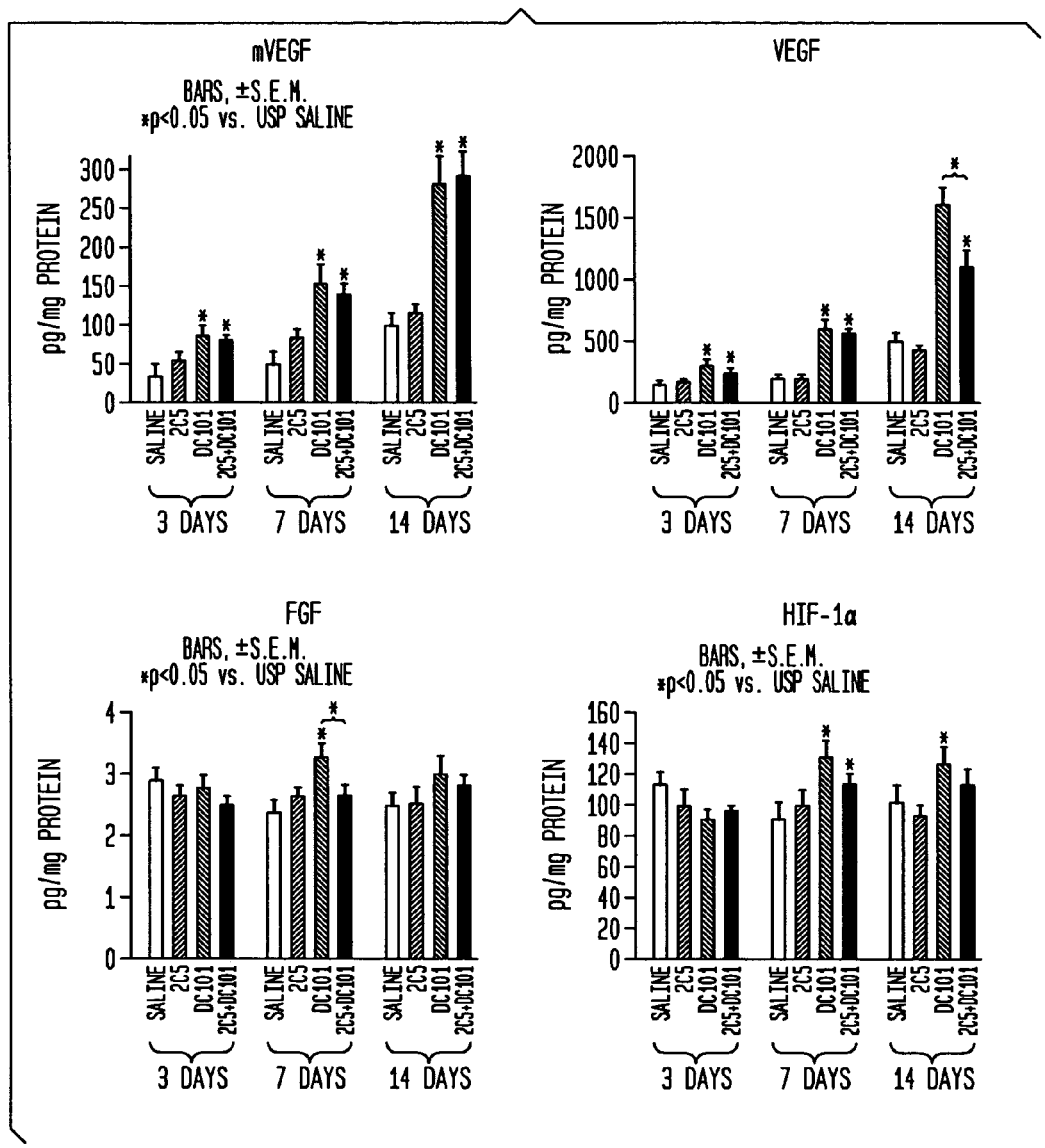

Effects of 2C5 antibody on PDGFRα, PDGF-BB and VEGF expression. NCI-H460 cell suspension (5×10$^5$ cells/mouse), was injected s.c. into female athymic mice. When tumors reached ~250 mm$^3$ the mice were randomized and divided into four treatment groups (n=35 each for USP saline, 2C5, DC101 and 2C5+DC101). At the day 3, day 7 and day 14, six animals from each group were sacrificed and their tumors were harvested. ELISA analysis was performed with tumor lysates to evaluate the level of PDGFRβ, PDGF-BB, mVEGFR2, mVEGF, hVEGF, FGF and HIF-1α (FIG. 14).

Figure 15A:
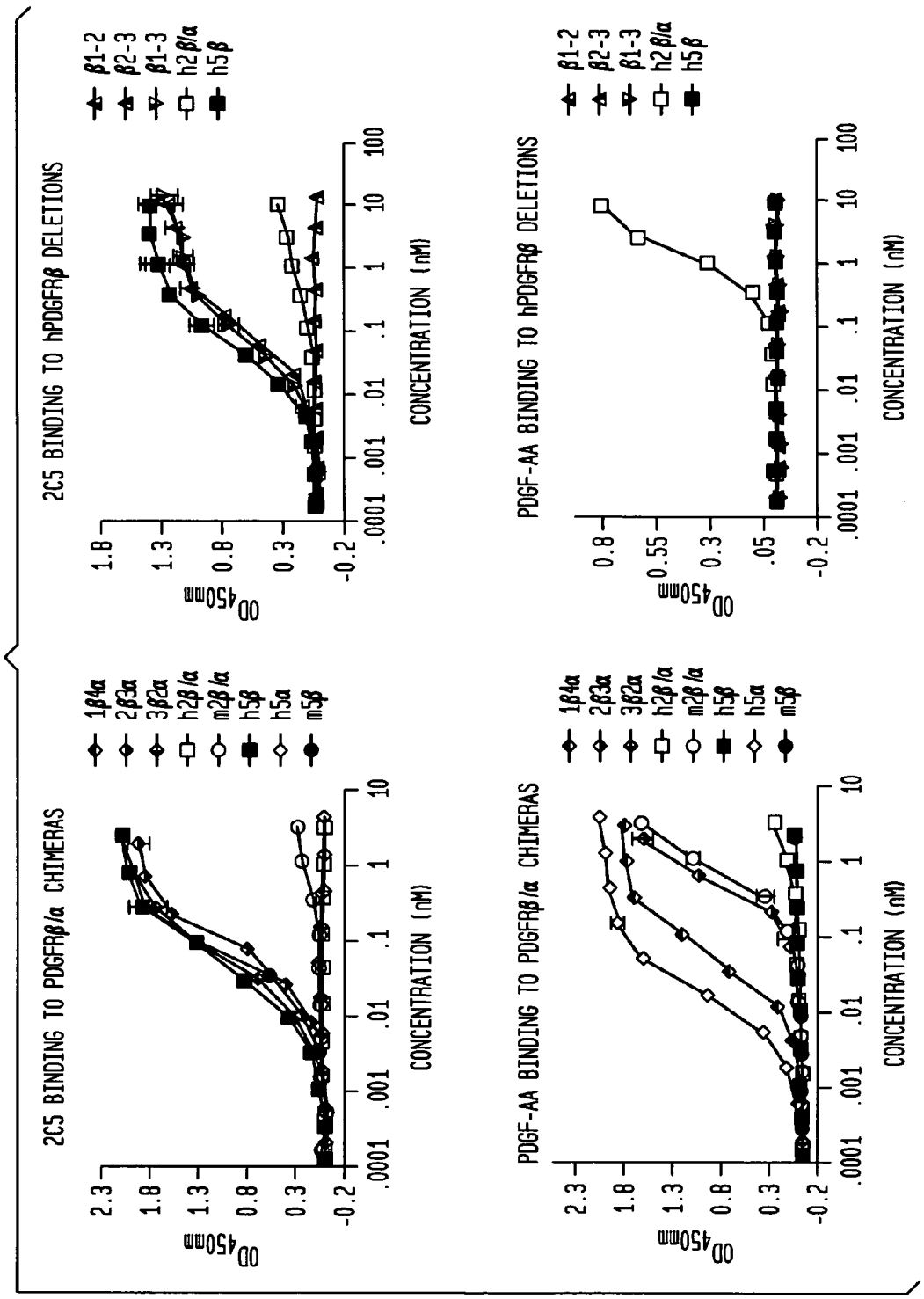
FIG. 15 shows the binding of 2C5 to PDGFRβ domains.
Figure 15B:
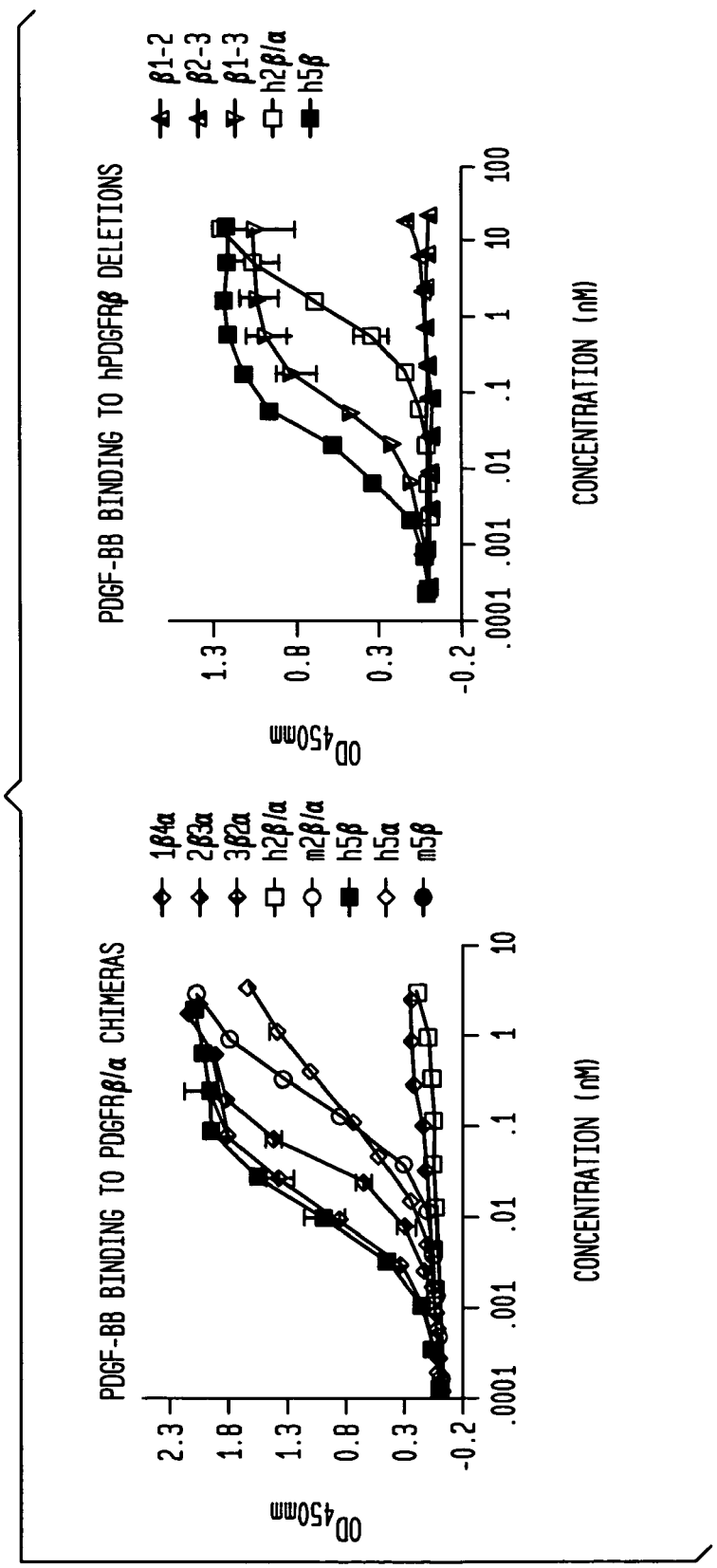

2C5 binds to domain 1 (D1) and domain 2 (D2) of PDGFRβ. Various chimeric constructs of PDGFRβ and PDGFRα were first made by domain swapping, starting from N-terminus to C-terminus with PDGFRβ domain(s) replacing PDGFRα domain(s). The PDGFRβ/α chimera were tested for the ability of 2C5 binding. Shorter versions of PDGFRβ, including D1D2, D2D3 and D1D2D3, were then made to confirm the 2C5 binding domains on PDGFRβ. The results indicated that 2C5 binds to PDGFRβ via both D1 and D2 of the receptor (FIG. 15 and Table 6).

TABLE 6

| | 1β4α | 2β3α | 3β2α | 4β1α | h5β | m5β | h5α | h2β/a | m2β/α | β1-2 | β1-3 | β2-3 |
|---|---|---|---|---|---|---|---|---|---|---|---|---|
| 2C5 | X | ✓ | ✓ | ✓ | ✓ | ✓ | X | X | X | ✓ | ✓ | X |
| PDGF-AA | ✓ | ✓ (weak) | X | X | X | X | ✓ | ✓ (weak) | ✓ (weak) | X | X | X |
| PDGF-BB | X | ✓ | ✓ | ✓ | ✓ | ✓ | ✓ | ✓ (weak) | ✓ (weak) | X | ✓ | X |

What is claimed is:

1. An antibody or fragment thereof that binds human PDGFRβ, comprising SYAIS (SEQ ID NO:20) at CDRH1; RIIPILGIANYAQKFQG (SEQ ID NO:22) at CDRH2; DMGSRNYYYFY (SEQ ID NO:24) at CDRH3; RASQSVGRYLA (SEQ ID NO:28) at CDRL1; GASNRAT (SEQ ID NO:30) at CDRL2; and QQRSNWPLT (SEQ ID NO:32) at CDRL3.

2. The antibody of claim 1, comprising a heavy chain variable domain amino acid sequence of SEQ ID NO:18 and a light chain variable domain amino acid sequence of SEQ ID NO:26.

3. The antibody or fragment thereof, of claim 2 comprising a human γ1 heavy-chain constant region and a human κ light-chain constant region.

4. The antibody of claim 1, which is selected from the group consisting of a single chain antibody, an Fab, a single chain Fv antibody.

5. An antibody or fragment thereof, of claim 1 comprising a VL comprising the amino acid sequence:
EIVLTQSPATLSLSPGERATLSCRASQSVGRYLAWYQQKPGQAPRLLIYGASNRATGIPARFSGSGSGTDFTLTISSLEPEDFAVYYCQQRSNWPLTFGGGTKVEIK (SEQ ID NO:26),
or a VH comprising the amino acid sequence: QVQLVQSGAEVKKPGSSVKVSCKASGGTFSSYAISWVRQAPGQGLEWMGRIIPILGIANYAQKFQGRVTITADKSTSTAYMELSSLRSEDTAVYYCARDMGSRNYYYFYWGQGTLVTVSS (SEQ ID NO:18).

6. A pharmaceutical composition comprising an antibody or fragment thereof, of claim 1 and a pharmaceutically acceptable carrier.

* * * * *

UNITED STATES PATENT AND TRADEMARK OFFICE
CERTIFICATE OF CORRECTION

| | |
|---|---|
| PATENT NO. | : 7,740,850 B2 |
| APPLICATION NO. | : 12/148482 |
| DATED | : June 22, 2010 |
| INVENTOR(S) | : Zhenping Zhu et al. |

It is certified that error appears in the above-identified patent and that said Letters Patent is hereby corrected as shown below:

| Issued Patent | | |
|---|---|---|
| Column | Line | Description of Error |
| First Page Col. 1 (Other Publications) | 1 | Delete "Batelyet" and insert -- Batley et --, therefor. |
| First Page Col. 2 (Other Publications) | 41 | Delete "Rearch" and insert -- Research --, therefor. |

Signed and Sealed this

Twenty-first Day of December, 2010

David J. Kappos
*Director of the United States Patent and Trademark Office*

SEQUENCE LISTING

<160> NUMBER OF SEQ ID NOS: 46

<210> SEQ ID NO 1
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 1

```
cag gtg cag ctg cag gag tcg ggg gga ggc ctg gtc aag cct ggg ggg      48
Gln Val Gln Leu Gln Glu Ser Gly Gly Gly Leu Val Lys Pro Gly Gly
1               5                   10                  15 tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
            20                  25                  30 agc atg aac tgg gtc cgc cag gct cca ggg aag ggg ctg gag tgg gtc     144
Ser Met Asn Trp Val Arg Gln Ala Pro Gly Lys Gly Leu Glu Trp Val
        35                  40                  45 tca tcc att agt agt agt agt agt tac ata tac tac gca gac tcc gtg     192
Ser Ser Ile Ser Ser Ser Ser Ser Tyr Ile Tyr Tyr Ala Asp Ser Val
    50                  55                  60 aag ggc cgg ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gtg tat tac tgt     288
Leu Gln Met Asn Ser Leu Arg Ala Glu Asp Thr Ala Val Tyr Tyr Cys
                85                  90                  95 gcg aaa ggg ggg cgc ccg ctc cta gtc ttt gac ttc tgg ggc cag gga     336
Ala Lys Gly Gly Arg Pro Leu Leu Val Phe Asp Phe Trp Gly Gln Gly
            100                 105                 110 acc ctg gtc acc gtc tca                                              354
Thr Leu Val Thr Val Ser
        115
```

<210> SEQ ID NO 2
<211> LENGTH: 118
<212> TYPE: PRT
<213> ORGANISM: Homo sapiens

<400> SEQUENCE: 2

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45
```

```
Ser Ser Ile Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Arg Pro Leu Leu Val Phe Asp Phe Trp Gly Gln Gly
            100                 105                 110

Thr Leu Val Thr Val Ser
        115

<210> SEQ ID NO 3
<211> LENGTH: 15
<212> TYPE: DNA
<213> ORGANISM: Homo sapiens
<220> FEATURE:
<221> NAME/KEY: CDS
<222> LOCATION: (1)..(15)

<400> SEQUENCE: 3 agc tat agc atg aac                                              15
Ser Tyr Ser Met Asn
1               5

<210> SEQ ID NO 4
<211> LENGTH: 5
<212> TYPE: PRT
<213> ORGANISM: Homo sapiens

<400> SEQUENCE: 4

Ser Tyr Ser Met Asn
1               5

<210> SEQ ID NO 5
<211> LENGTH: 51
<212> TYPE: DNA
<213> ORGANISM: Homo sapiens
<220> FEATURE:
<221> NAME/KEY: CDS
<222> LOCATION: (1)..(51)

<400> SEQUENCE: 5 tcc att agt agt agt agt agt tac ata tac tac gca gac tcc gtg aag    48
Ser Ile Ser Ser Ser Ser Ser Tyr Ile Tyr Tyr Ala Asp Ser Val Lys
1               5                   10                  15 ggc                                                              51
Gly

<210> SEQ ID NO 6
<211> LENGTH: 17
<212> TYPE: PRT
<213> ORGANISM: Homo sapiens

<400> SEQUENCE: 6

Ser Ile Ser Ser Ser Ser Ser Tyr Ile Tyr Tyr Ala Asp Ser Val Lys
1               5                   10                  15

Gly

<210> SEQ ID NO 7
<211> LENGTH: 30
<212> TYPE: DNA
<213> ORGANISM: Homo sapiens
<220> FEATURE:
<221> NAME/KEY: CDS
```

<210> SEQ ID NO 7 (continued)
<222> LOCATION: (1)..(30)

<400> SEQUENCE: 7

```
ggg ggg cgc ccg ctc cta gtc ttt gac ttc                              30
Gly Gly Arg Pro Leu Leu Val Phe Asp Phe
1               5                   10
```

<210> SEQ ID NO 8
<211> LENGTH: 10
<212> TYPE: PRT
<213> ORGANISM: Homo sapiens

<400> SEQUENCE: 8

```
Gly Gly Arg Pro Leu Leu Val Phe Asp Phe
1               5                   10
```

<210> SEQ ID NO 9
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 9

```
gaa att gtg atg aca cag tct cca ggc acc ctg tct ttg tct cca ggg      48
Glu Ile Val Met Thr Gln Ser Pro Gly Thr Leu Ser Leu Ser Pro Gly
1               5                   10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
            20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
        35                  40                  45 atc tat gat gca tcc aag agg gcc act ggc atc cca gcc agg ttc agt     192
Ile Tyr Asp Ala Ser Lys Arg Ala Thr Gly Ile Pro Ala Arg Phe Ser
    50                  55                  60 ggc agt ggg tct ggg aca gac ttc act ctc acc atc agc acc cta gag     240
Gly Ser Gly Ser Gly Thr Asp Phe Thr Leu Thr Ile Ser Thr Leu Glu
65                  70                  75                  80 tct gaa gat tct gca gtt tat tac tgt cag caa cgt ggc tac tgg cct     288
Ser Glu Asp Ser Ala Val Tyr Tyr Cys Gln Gln Arg Gly Tyr Trp Pro
                85                  90                  95 ccc atc acc ttc ggc caa ggg aca cga ctg gag att aaa cga             330
Pro Ile Thr Phe Gly Gln Gly Thr Arg Leu Glu Ile Lys Arg
            100                 105                 110
```

<210> SEQ ID NO 10
<211> LENGTH: 110
<212> TYPE: PRT
<213> ORGANISM: Homo sapiens

<400> SEQUENCE: 10

```
Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Lys Arg Ala Thr Gly Ile Pro Ala Arg Phe Ser
    50                  55                  60

Gly Ser Gly Ser Gly Thr Asp Phe Thr Leu Thr Ile Ser Thr Leu Glu
```

```
                65                  70                  75                  80
            Ser Glu Asp Ser Ala Val Tyr Tyr Cys Gln Gln Arg Gly Tyr Trp Pro
                                85                  90                  95

Pro Ile Thr Phe Gly Gln Gly Thr Arg Leu Glu Ile Lys Arg
                            100                 105                 110

<210> SEQ ID NO 11
<211> LENGTH: 36
<212> TYPE: DNA
<213> ORGANISM: Homo sapiens
<220> FEATURE:
<221> NAME/KEY: CDS
<222> LOCATION: (1)..(36)

<400> SEQUENCE: 11 agg gcc agt cag agt gtt agc agc agc tac tta gcc                              36
Arg Ala Ser Gln Ser Val Ser Ser Ser Tyr Leu Ala
1               5                   10

<210> SEQ ID NO 12
<211> LENGTH: 12
<212> TYPE: PRT
<213> ORGANISM: Homo sapiens

<400> SEQUENCE: 12

Arg Ala Ser Gln Ser Val Ser Ser Ser Tyr Leu Ala
1               5                   10

<210> SEQ ID NO 13
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 13 gat gca tcc aag agg gcc acc                                                  21
Asp Ala Ser Lys Arg Ala Thr
1               5

<210> SEQ ID NO 14
<211> LENGTH: 7
<212> TYPE: PRT
<213> ORGANISM: Homo sapiens

<400> SEQUENCE: 14

Asp Ala Ser Lys Arg Ala Thr
1               5

<210> SEQ ID NO 15
<211> LENGTH: 30
<212> TYPE: DNA
<213> ORGANISM: Homo sapiens
<220> FEATURE:
<221> NAME/KEY: CDS
<222> LOCATION: (1)..(30)

<400> SEQUENCE: 15 cag caa cgt ggc tac tgg cct ccc atc acc                                      30
Gln Gln Arg Gly Tyr Trp Pro Pro Ile Thr
1               5                   10

<210> SEQ ID NO 16
<211> LENGTH: 10
<212> TYPE: PRT
```

<213> ORGANISM: Homo sapiens

<400> SEQUENCE: 16

Gln Gln Arg Gly Tyr Trp Pro Pro Ile Thr
1               5                   10

<210> SEQ ID NO 17
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 17

```
cag gtg cag ctg gtg cag tct ggg gct gag gtg aag aag cct ggg tcc      48
Gln Val Gln Leu Val Gln Ser Gly Ala Glu Val Lys Lys Pro Gly Ser
1               5                   10                  15 tcg gtg aag gtc tcc tgc aag gct tct gga ggc acc ttc agc agc tat      96
Ser Val Lys Val Ser Cys Lys Ala Ser Gly Gly Thr Phe Ser Ser Tyr
            20                  25                  30 gct atc agc tgg gtg cga cag gcc cct gga caa ggg ctt gag tgg atg     144
Ala Ile Ser Trp Val Arg Gln Ala Pro Gly Gln Gly Leu Glu Trp Met
        35                  40                  45 gga agg atc atc cct atc ctt ggt ata gca aac tac gca cag aag ttc     192
Gly Arg Ile Ile Pro Ile Leu Gly Ile Ala Asn Tyr Ala Gln Lys Phe
    50                  55                  60 cag ggc aga gtc acg att acc gcg gac aaa tcc acg agc aca gcc tac     240
Gln Gly Arg Val Thr Ile Thr Ala Asp Lys Ser Thr Ser Thr Ala Tyr
65                  70                  75                  80 atg gag ctg agc agc ctg aga tct gag gac acg gcc gtc tat tac tgt     288
Met Glu Leu Ser Ser Leu Arg Ser Glu Asp Thr Ala Val Tyr Tyr Cys
                85                  90                  95 gcg aga gat atg ggt tca agg aat tat tat tac ttc tac tgg ggc cag     336
Ala Arg Asp Met Gly Ser Arg Asn Tyr Tyr Tyr Phe Tyr Trp Gly Gln
            100                 105                 110 gga acc ctg gtc acc gtc tca agc                                     360
Gly Thr Leu Val Thr Val Ser Ser
        115                 120
```

<210> SEQ ID NO 18
<211> LENGTH: 120
<212> TYPE: PRT
<213> ORGANISM: Homo sapiens

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Met Gly Ser Arg Asn Tyr Tyr Tyr Phe Tyr Trp Gly Gln
            100                 105                 110

-continued

Gly Thr Leu Val Thr Val Ser Ser
        115             120

<210> SEQ ID NO 19
<211> LENGTH: 15
<212> TYPE: DNA
<213> ORGANISM: Homo sapiens
<220> FEATURE:
<221> NAME/KEY: CDS
<222> LOCATION: (1)..(15)

<400> SEQUENCE: 19 agc tat gct atc agc                                           15
Ser Tyr Ala Ile Ser
1               5

<210> SEQ ID NO 20
<211> LENGTH: 5
<212> TYPE: PRT
<213> ORGANISM: Homo sapiens

<400> SEQUENCE: 20

Ser Tyr Ala Ile Ser
1               5

<210> SEQ ID NO 21
<211> LENGTH: 51
<212> TYPE: DNA
<213> ORGANISM: Homo sapiens
<220> FEATURE:
<221> NAME/KEY: CDS
<222> LOCATION: (1)..(51)

<400> SEQUENCE: 21 agg atc atc cct atc ctt ggt ata gca aac tac gca cag aag ttc cag    48
Arg Ile Ile Pro Ile Leu Gly Ile Ala Asn Tyr Ala Gln Lys Phe Gln
1               5                   10                  15
ggc                                                           51
Gly <210> SEQ ID NO 22
<211> LENGTH: 17
<212> TYPE: PRT
<213> ORGANISM: Homo sapiens

<400> SEQUENCE: 22

Arg Ile Ile Pro Ile Leu Gly Ile Ala Asn Tyr Ala Gln Lys Phe Gln
1               5                   10                  15
Gly

<210> SEQ ID NO 23
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 23 gat atg ggt tca agg aat tat tat tac ttc tac                   33
Asp Met Gly Ser Arg Asn Tyr Tyr Tyr Phe Tyr
1               5                   10

<210> SEQ ID NO 24
<211> LENGTH: 11
<212> TYPE: PRT

<213> ORGANISM: Homo sapiens

<400> SEQUENCE: 24

Asp Met Gly Ser Arg Asn Tyr Tyr Tyr Phe Tyr
1               5                   10

<210> SEQ ID NO 25
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 25

```
gaa att gtg ctg act cag tct cca gcc acc ctg tct ttg tct cca ggg      48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt ggc agg tac      96
Glu Arg Ala Thr Leu Ser Cys Arg Ala Ser Gln Ser Val Gly Arg Tyr
                20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
            35                  40                  45 tat ggt gca tcc aac agg gcc act ggc atc cca gcc agg ttc agt ggc     192
Tyr Gly Ala Ser Asn Arg Ala Thr Gly Ile Pro Ala Arg Phe Ser Gly
        50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg cct ctc     288
Glu Asp Phe Ala Val Tyr Tyr Cys Gln Gln Arg Ser Asn Trp Pro Leu
                85                  90                  95 act ttc ggc gga ggg acc aag gtg gag atc aaa                         321
Thr Phe Gly Gly Gly Thr Lys Val Glu Ile Lys
            100                 105
```

<210> SEQ ID NO 26
<211> LENGTH: 107
<212> TYPE: PRT
<213> ORGANISM: Homo sapiens

<400> SEQUENCE: 26

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Arg Tyr
                20                  25                  30

Leu Ala Trp Tyr Gln Gln Lys Pro Gly Gln Ala Pro Arg Leu Leu Ile
            35                  40                  45

Tyr Gly Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 27
<211> LENGTH: 33
<212> TYPE: DNA

```
<213> ORGANISM: Homo sapiens
<220> FEATURE:
<221> NAME/KEY: CDS
<222> LOCATION: (1)..(33)

<400> SEQUENCE: 27 agg gcc agt cag agt gtt ggc agg tac tta gcc         33
Arg Ala Ser Gln Ser Val Gly Arg Tyr Leu Ala
1               5                   10

<210> SEQ ID NO 28
<211> LENGTH: 11
<212> TYPE: PRT
<213> ORGANISM: Homo sapiens

<400> SEQUENCE: 28

Arg Ala Ser Gln Ser Val Gly Arg Tyr Leu Ala
1               5                   10

<210> SEQ ID NO 29
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 29 ggt gca tcc aac agg gcc act                         21
Gly Ala Ser Asn Arg Ala Thr
1               5

<210> SEQ ID NO 30
<211> LENGTH: 7
<212> TYPE: PRT
<213> ORGANISM: Homo sapiens

<400> SEQUENCE: 30

Gly Ala Ser Asn Arg Ala Thr
1               5

<210> SEQ ID NO 31
<211> LENGTH: 27
<212> TYPE: DNA
<213> ORGANISM: Homo sapiens
<220> FEATURE:
<221> NAME/KEY: CDS
<222> LOCATION: (1)..(27)

<400> SEQUENCE: 31 cag cag cgt agc aac tgg cct ctc act                 27
Gln Gln Arg Ser Asn Trp Pro Leu Thr
1               5

<210> SEQ ID NO 32
<211> LENGTH: 9
<212> TYPE: PRT
<213> ORGANISM: Homo sapiens

<400> SEQUENCE: 32

Gln Gln Arg Ser Asn Trp Pro Leu Thr
1               5

<210> SEQ ID NO 33
<211> LENGTH: 348
<212> TYPE: DNA
<213> ORGANISM: Homo sapiens
```

<220> FEATURE:
<221> NAME/KEY: CDS
<222> LOCATION: (1)..(348)

<400> SEQUENCE: 33

| gag | gtg | cag | ctg | gtg | cag | tct | ggg | gga | ggc | ctg | gtc | aag | cct | ggg | ggg | 48 |
| Glu | Val | Gln | Leu | Val | Gln | Ser | Gly | Gly | Gly | Leu | Val | Lys | Pro | Gly | Gly | |
| 1 | | | | 5 | | | | | 10 | | | | | 15 | | |

| tcc | ctg | aga | ctc | tcc | tgt | gca | gcc | tct | gga | ttc | acc | ttc | agt | agc | tat | 96 |
| Ser | Leu | Arg | Leu | Ser | Cys | Ala | Ala | Ser | Gly | Phe | Thr | Phe | Ser | Ser | Tyr | |
| | | | 20 | | | | | 25 | | | | | 30 | | | |

| agc | atg | aac | tgg | gtc | cgc | cag | gct | cca | ggg | aag | ggg | ctg | gag | tgg | gtc | 144 |
| Ser | Met | Asn | Trp | Val | Arg | Gln | Ala | Pro | Gly | Lys | Gly | Leu | Glu | Trp | Val | |
| | | 35 | | | | | 40 | | | | | 45 | | | | |

| tca | tcc | att | agt | agt | agt | agt | agt | tac | ata | tac | tac | gca | gac | tca | gtg | 192 |
| Ser | Ser | Ile | Ser | Ser | Ser | Ser | Ser | Tyr | Ile | Tyr | Tyr | Ala | Asp | Ser | Val | |
| 50 | | | | | 55 | | | | | 60 | | | | | | |

| aag | ggc | cga | ttc | acc | atc | tcc | aga | gac | aac | gcc | aag | aac | tca | ctg | tat | 240 |
| Lys | Gly | Arg | Phe | Thr | Ile | Ser | Arg | Asp | Asn | Ala | Lys | Asn | Ser | Leu | Tyr | |
| 65 | | | | 70 | | | | | 75 | | | | | 80 | | |

| ctg | caa | atg | aac | agc | ctg | aga | gcc | gag | gac | acg | gct | gtg | tat | tac | tgt | 288 |
| Leu | Gln | Met | Asn | Ser | Leu | Arg | Ala | Glu | Asp | Thr | Ala | Val | Tyr | Tyr | Cys | |
| | | | 85 | | | | | 90 | | | | | 95 | | | |

| gcg | aga | gtc | aca | gat | gct | ttt | gat | atc | tgg | ggc | caa | ggg | aca | atg | gtc | 336 |
| Ala | Arg | Val | Thr | Asp | Ala | Phe | Asp | Ile | Trp | Gly | Gln | Gly | Thr | Met | Val | |
| | | | 100 | | | | | 105 | | | | | 110 | | | |

| acc | gtc | tca | agc | | | | | | | | | | | | | 348 |
| Thr | Val | Ser | Ser | | | | | | | | | | | | | |
| | | 115 | | | | | | | | | | | | | | |

<210> SEQ ID NO 34
<211> LENGTH: 116
<212> TYPE: PRT
<213> ORGANISM: Homo sapiens

<400> SEQUENCE: 34

| Glu | Val | Gln | Leu | Val | Gln | Ser | Gly | Gly | Gly | Leu | Val | Lys | Pro | Gly | Gly |
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |

| Ser | Met | Asn | Trp | Val | Arg | Gln | Ala | Pro | Gly | Lys | Gly | Leu | Glu | Trp | Val |
| | | 35 | | | | | 40 | | | | | 45 | | | |

| Ser | Ser | Ile | Ser | Ser | Ser | Ser | Ser | Tyr | Ile | Tyr | Tyr | Ala | Asp | Ser | Val |
| 50 | | | | | 55 | | | | | 60 | | | | | |

| Lys | Gly | Arg | Phe | Thr | Ile | Ser | Arg | Asp | Asn | Ala | Lys | Asn | Ser | Leu | Tyr |
| 65 | | | | 70 | | | | | 75 | | | | | 80 | |

| Leu | Gln | Met | Asn | Ser | Leu | Arg | Ala | Glu | Asp | Thr | Ala | Val | Tyr | Tyr | Cys |
| | | | 85 | | | | | 90 | | | | | 95 | | |

| Ala | Arg | Val | Thr | Asp | Ala | Phe | Asp | Ile | Trp | Gly | Gln | Gly | Thr | Met | Val |
| | | | 100 | | | | | 105 | | | | | 110 | | |

| Thr | Val | Ser | Ser |
| | | 115 | |

<210> SEQ ID NO 35
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 35

```
gaa att gtg atg aca cag tct cca gcc acc ctg tct ttg tct cca ggg        48
Glu Ile Val Met Thr Gln Ser Pro Ala Thr Leu Ser Leu Ser Pro Gly
1               5                   10                  15 gaa aga gcc acc ctc tcc tgc agg gcc agt cag agt gtt agc agc tac        96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc       144
Leu Ala Trp Tyr Gln Gln Lys Pro Gly Gln Ala Pro Arg Leu Leu Ile
        35                  40                  45 tat gat tca tcc aac agg gcc act ggc atc cca gcc aga ttc agt ggc       192
Tyr Asp Ser Ser Asn Arg Ala Thr Gly Ile Pro Ala Arg Phe Ser Gly
    50                  55                  60 agt ggg tct ggg aca gac ttc act ctc acc atc agc agc cta gag cct       240
Ser Gly Ser Gly Thr Asp Phe Thr Leu Thr Ile Ser Ser Leu Glu Pro
65                  70                  75                  80 gaa gat ttt gca act tat tac tgt cta cag cat aac act ttt cct ccg       288
Glu Asp Phe Ala Thr Tyr Tyr Cys Leu Gln His Asn Thr Phe Pro Pro
                85                  90                  95 acg ttc ggc caa ggg acc aag gtg gaa atc aaa                           321
Thr Phe Gly Gln Gly Thr Lys Val Glu Ile Lys
            100                 105
```

<210> SEQ ID NO 36
<211> LENGTH: 107
<212> TYPE: PRT
<213> ORGANISM: Homo sapiens

<400> SEQUENCE: 36

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Leu Gln His Asn Thr Phe Pro Pro
                85                  90                  95

Thr Phe Gly Gln Gly Thr Lys Val Glu Ile Lys
            100                 105
```

<210> SEQ ID NO 37
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 37

```
gac atc cag atg acc cag tct cca tct tcc gtg tct gca tct ata gga        48
Asp Ile Gln Met Thr Gln Ser Pro Ser Ser Val Ser Ala Ser Ile Gly
1               5                   10                  15 gac aga gtc acc atc act tgt cgg gcg agt cag ggt att gac aac tgg        96
Asp Arg Val Thr Ile Thr Cys Arg Ala Ser Gln Gly Ile Asp Asn Trp
            20                  25                  30 tta ggc tgg tat cag cag aaa cct ggg aaa gcc cct aaa ctc ctg atc       144
```

```
Leu Gly Trp Tyr Gln Gln Lys Pro Gly Lys Ala Pro Lys Leu Leu Ile
        35                  40                  45 tac gat gca tcc aat ttg gac aca ggg gtc cca tca agg ttc agt gga     192
Tyr Asp Ala Ser Asn Leu Asp Thr Gly Val Pro Ser Arg Phe Ser Gly
 50                  55                  60 agt gga tct ggg aca tat ttt act ctc acc atc agt agc ctg caa gct     240
Ser Gly Ser Gly Thr Tyr Phe Thr Leu Thr Ile Ser Ser Leu Gln Ala
 65                  70                  75                  80 gaa gat ttt gca gtt tat ttc tgt caa cag gct aaa gct ttt cct ccc     288
Glu Asp Phe Ala Val Tyr Phe Cys Gln Gln Ala Lys Ala Phe Pro Pro
                 85                  90                  95 act ttc ggc gga ggg acc aag gtg gac atc aaa                         321
Thr Phe Gly Gly Gly Thr Lys Val Asp Ile Lys
                100                 105

<210> SEQ ID NO 38
<211> LENGTH: 107
<212> TYPE: PRT
<213> ORGANISM: Homo sapiens

<400> SEQUENCE: 38

Asp Ile Gln Met Thr Gln Ser Pro Ser Ser Val Ser Ala Ser Ile Gly
 1               5                  10                  15

Asp Arg Val Thr Ile Thr Cys Arg Ala Ser Gln Gly Ile Asp Asn Trp
             20                  25                  30

Leu Gly Trp Tyr Gln Gln Lys Pro Gly Lys Ala Pro Lys Leu Leu Ile
        35                  40                  45

Tyr Asp Ala Ser Asn Leu Asp Thr Gly Val Pro Ser Arg Phe Ser Gly
 50                  55                  60

Ser Gly Ser Gly Thr Tyr Phe Thr Leu Thr Ile Ser Ser Leu Gln Ala
 65                  70                  75                  80

Glu Asp Phe Ala Val Tyr Phe Cys Gln Gln Ala Lys Ala Phe Pro Pro
                 85                  90                  95

Thr Phe Gly Gly Gly Thr Lys Val Asp Ile Lys
                100                 105

<210> SEQ ID NO 39
<211> LENGTH: 348
<212> TYPE: DNA
<213> ORGANISM: Mus musculus
<220> FEATURE:
<221> NAME/KEY: CDS
<222> LOCATION: (1)..(348)

<400> SEQUENCE: 39 cag gtc aaa ctg cag cag tct ggg gca gag ctt gtc aag cca ggg gcc     48
Gln Val Lys Leu Gln Gln Ser Gly Ala Glu Leu Val Lys Pro Gly Ala
 1               5                  10                  15 tca gtc aag ttg tcc tgc aca gct tct ggc ttc aac att aaa gac acc     96
Ser Val Lys Leu Ser Cys Thr Ala Ser Gly Phe Asn Ile Lys Asp Thr
             20                  25                  30 tat ata cac tgg gtg aag cag agc cct gaa cag ggc ctg gag tgg att     144
Tyr Ile His Trp Val Lys Gln Ser Pro Glu Gln Gly Leu Glu Trp Ile
        35                  40                  45 gga agg atc gat cct ccg aat gat aat act aaa tat gac ccg aag ttc     192
Gly Arg Ile Asp Pro Pro Asn Asp Asn Thr Lys Tyr Asp Pro Lys Phe
 50                  55                  60 cag ggc aag gcc act ata aca gca gac aca tcc tcc aat aca gcc tac     240
Gln Gly Lys Ala Thr Ile Thr Ala Asp Thr Ser Ser Asn Thr Ala Tyr
 65                  70                  75                  80
```

```
atg cag ctc cgc agc ctg aca tct gag gac act gcc gtc tat tac tgt      288
Met Gln Leu Arg Ser Leu Thr Ser Glu Asp Thr Ala Val Tyr Tyr Cys
            85                  90                  95 gcc ctc cca ccg ttc tac ttt gac tac tgg ggc cat ggc acc acg gtc      336
Ala Leu Pro Pro Phe Tyr Phe Asp Tyr Trp Gly His Gly Thr Thr Val
        100                 105                 110 acc gtc tcc tca                                                      348
Thr Val Ser Ser
        115

<210> SEQ ID NO 40
<211> LENGTH: 116
<212> TYPE: PRT
<213> ORGANISM: Mus musculus

<400> SEQUENCE: 40

Gln Val Lys Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Ser Pro Glu Gln Gly Leu Glu Trp Ile
        35                  40                  45

Gly Arg Ile Asp Pro Asn Asp Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Met Gln Leu Arg Ser Leu Thr Ser Glu Asp Thr Ala Val Tyr Tyr Cys
            85                  90                  95

Ala Leu Pro Pro Phe Tyr Phe Asp Tyr Trp Gly His Gly Thr Thr Val
        100                 105                 110

Thr Val Ser Ser
        115

<210> SEQ ID NO 41
<211> LENGTH: 327
<212> TYPE: DNA
<213> ORGANISM: Mus musculus
<220> FEATURE:
<221> NAME/KEY: CDS
<222> LOCATION: (1)..(327)

<400> SEQUENCE: 41 gac atc gag ctc act cag tct cca aaa ttc atg tcc aca tca gta gga      48
Asp Ile Glu Leu Thr Gln Ser Pro Lys Phe Met Ser Thr Ser Val Gly
1               5                   10                  15 gac agg gtc agc gtc acc tgc aag gcc agt cag aat gtg gat act aat      96
Asp Arg Val Ser Val Thr Cys Lys Ala Ser Gln Asn Val Asp Thr Asn
            20                  25                  30 gta gcc tgg tat caa cag aaa cca ggg caa tct cct aaa gca ctg att      144
Val Ala Trp Tyr Gln Gln Lys Pro Gly Gln Ser Pro Lys Ala Leu Ile
        35                  40                  45 tac tcg gca tcc tac cgg tac agt gga gtc cct gat cgc ttc aca ggc      192
Tyr Ser Ala Ser Tyr Arg Tyr Ser Gly Val Pro Asp Arg Phe Thr Gly
    50                  55                  60 agt gga tct ggg aca gat ttc act ctc acc atc agc aat gtg cag tct      240
Ser Gly Ser Gly Thr Asp Phe Thr Leu Thr Ile Ser Asn Val Gln Ser
65                  70                  75                  80 gaa gac ttg gca gag tat ttc tgt cag caa tat aac agc ttt cct tac      288
Glu Asp Leu Ala Glu Tyr Phe Cys Gln Gln Tyr Asn Ser Phe Pro Tyr
            85                  90                  95
```

```
acg ttc gga ggg ggg acc aag ctg gaa ata aaa cgg gcg        327
Thr Phe Gly Gly Gly Thr Lys Leu Glu Ile Lys Arg Ala
            100                 105
```

<210> SEQ ID NO 42
<211> LENGTH: 109
<212> TYPE: PRT
<213> ORGANISM: Mus musculus

<400> SEQUENCE: 42

```
Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Phe Pro Tyr
                85                  90                  95

Thr Phe Gly Gly Gly Thr Lys Leu Glu Ile Lys Arg Ala
            100                 105
```

<210> SEQ ID NO 43
<211> LENGTH: 378
<212> TYPE: DNA
<213> ORGANISM: Homo sapiens
<220> FEATURE:
<221> NAME/KEY: CDS
<222> LOCATION: (1)..(378)

<400> SEQUENCE: 43

```
cag gcg cag gtg gtg gag tct ggg gga ggc gtg gtc cag tct ggg agg        48
Gln Ala Gln Val Val Glu Ser Gly Gly Gly Val Val Gln Ser Gly Arg
1               5                   10                  15 tcc ctg aga ctc tcc tgt gca gcg tct gga ttc gcc ttc agt agc tac        96
Ser Leu Arg Leu Ser Cys Ala Ala Ser Gly Phe Ala Phe Ser Ser Tyr
            20                  25                  30 ggc atg cac tgg gtc cgc cag gct cca ggc aag ggg ctg gag tgg gtg       144
Gly Met His Trp Val Arg Gln Ala Pro Gly Lys Gly Leu Glu Trp Val
        35                  40                  45 gca gtt ata tgg tat gat gga agt aat aaa tac tat gca gac tcc gtg       192
Ala Val Ile Trp Tyr Asp Gly Ser Asn Lys Tyr Tyr Ala Asp Ser Val
    50                  55                  60 agg ggc cga ttc acc atc tcc aga gac aat tcc gag aac acg ctg tat       240
Arg Gly Arg Phe Thr Ile Ser Arg Asp Asn Ser Glu Asn Thr Leu Tyr
65                  70                  75                  80 ctg caa atg aac agc ctg aga gcc gag gac acc gct gtg tat tac tgt       288
Leu Gln Met Asn Ser Leu Arg Ala Glu Asp Thr Ala Val Tyr Tyr Cys
                85                  90                  95 gcc aga gat cac tat ggt tcg ggg gtg cac cac tat ttc tac tac ggt       336
Ala Arg Asp His Tyr Gly Ser Gly Val His His Tyr Phe Tyr Tyr Gly
            100                 105                 110 ctg gac gtc tgg ggc caa ggg acc acg gtc acc gtc tcc tca              378
Leu Asp Val Trp Gly Gln Gly Thr Thr Val Thr Val Ser Ser
        115                 120                 125
```

<210> SEQ ID NO 44
<211> LENGTH: 126

```
<212> TYPE: PRT
<213> ORGANISM: Homo sapiens

<400> SEQUENCE: 44

Gln Ala Gln Val Val Glu Ser Gly Gly Val Val Gln Ser Gly Arg
1               5                   10                  15

Ser Leu Arg Leu Ser Cys Ala Ala Ser Gly Phe Ala Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Ala Asp Ser Val
50                  55                  60

Arg Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Tyr Gly Ser Gly Val His His Tyr Phe Tyr Tyr Gly
                100                 105                 110

Leu Asp Val Trp Gly Gln Gly Thr Thr Val Thr Val Ser Ser
            115                 120                 125

<210> SEQ ID NO 45
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 45 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
            20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca ccg     288
Pro Glu Asp Phe Ala Val Tyr Tyr Cys Gln Gln Tyr Gly Ser Ser Pro
                85                  90                  95 ctc act ttc ggc gga ggg acc aag gtg gag atc aaa                     324
Leu Thr Phe Gly Gly Gly Thr Lys Val Glu Ile Lys
                100                 105

<210> SEQ ID NO 46
<211> LENGTH: 108
<212> TYPE: PRT
<213> ORGANISM: Homo sapiens

<400> SEQUENCE: 46

Glu Ile Val Leu Thr Gln Ser Pro Gly Thr Leu Ser Leu Ser Pro Gly
1               5                   10                  15
```

-continued

```
Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                 70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105
```